US011077178B2

(12) United States Patent
Perera et al.

(10) Patent No.: US 11,077,178 B2
(45) Date of Patent: Aug. 3, 2021

(54) CHIMERIC ANTIGEN RECEPTOR (CAR) THAT TARGETS CHEMOKINE RECEPTOR CCR4 AND ITS USE

(71) Applicants: THE UNITED STATES OF AMERICA, as represented by the Secretary, Department of Health and Human Services, Bethesda, MD (US); The United States Government as represented by the Department of Veterans Affairs, Washington, DC (US)

(72) Inventors: Liyanage Parakrama Perera, Bethesda, MD (US); Thomas Alexander Waldmann, Bethesda, MD (US); Kevin Charles Conlon, Bethesda, MD (US); Pin-Yu Perera, Washington, DC (US)

(73) Assignees: The United States of America, as represented by the Secretary, Department of Health and Human Services, Bethesda, MD (US); The United States Government as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/334,724

(22) PCT Filed: Sep. 20, 2017

(86) PCT No.: PCT/US2017/052437
§ 371 (c)(1),
(2) Date: Mar. 19, 2019

(87) PCT Pub. No.: WO2018/057585
PCT Pub. Date: Mar. 29, 2018

(65) Prior Publication Data
US 2019/0233526 A1 Aug. 1, 2019

Related U.S. Application Data

(60) Provisional application No. 62/397,810, filed on Sep. 21, 2016.

(51) Int. Cl.
A61K 39/00 (2006.01)
A61P 35/02 (2006.01)
C07K 14/725 (2006.01)
C07K 14/705 (2006.01)
C07K 16/28 (2006.01)
A61P 35/00 (2006.01)
A61K 31/7076 (2006.01)
A61K 35/17 (2015.01)
A61K 31/675 (2006.01)

(52) U.S. Cl.
CPC ........ *A61K 39/0011* (2013.01); *A61K 31/675* (2013.01); *A61K 31/7076* (2013.01); *A61K 35/17* (2013.01); *A61P 35/00* (2018.01); *A61P 35/02* (2018.01); *C07K 14/7051* (2013.01); *C07K 14/70517* (2013.01); *C07K 14/70578* (2013.01); *C07K 16/2866* (2013.01); *A61K 2039/5156* (2013.01); *A61K 2039/5158* (2013.01); *C07K 2317/24* (2013.01); *C07K 2317/622* (2013.01); *C07K 2319/03* (2013.01); *C07K 2319/33* (2013.01)

(58) Field of Classification Search
CPC ............ C07K 16/2866; C07K 14/7051; C07K 14/70517; C07K 14/70578; C07K 2317/24; C07K 2319/33; C07K 2317/622; C07K 2319/03; A61K 39/0011; A61K 31/675; A61K 31/7076; A61K 35/17; A61K 2039/5156; A61K 2039/5158; A61P 35/00; A61P 35/02
See application file for complete search history.

(56) References Cited

U.S. PATENT DOCUMENTS

| 2004/0043401 A1* | 3/2004 | Sadelain | C07H 21/04 435/6.16 |
| 2012/0213783 A1* | 8/2012 | Rosenberg | C07K 16/42 424/134.1 |
| 2016/0046724 A1* | 2/2016 | Brogdon | C07K 16/2878 424/134.1 |
| 2017/0281766 A1* | 10/2017 | Wiltzius | A61P 35/00 |

FOREIGN PATENT DOCUMENTS

| WO | WO-2008150485 A2 * | 12/2008 | ............. A61P 35/00 |
| WO | WO-2012079000 A1 * | 6/2012 | ....... C07K 14/70578 |
| WO | WO-2013123061 A1 * | 8/2013 | ............... C12N 7/00 |
| WO | WO 2013/166500 A1 | 11/2013 | |
| WO | WO-2013166500 A1 * | 11/2013 | ............. A61P 35/00 |
| WO | WO 2016/100985 A2 | 6/2016 | |

OTHER PUBLICATIONS

Mihara et al. (2016, Blood Cancer J., vol. 6(15), e421) (Year: 2016).*

(Continued)

*Primary Examiner* — Amy E Juedes
*Assistant Examiner* — Brian Hartnett
(74) *Attorney, Agent, or Firm* — Klarquist Sparkman, LLP

(57) ABSTRACT

A chimeric antigen receptor is disclosed that includes: (a) an scFv comprising a light chain variable domain ($V_L$) and a heavy chain variable domain ($V_H$), wherein the scFv specifically binds to CCR4; (b) a hinge and transmembrane domain from CD8; (c) an intracellular 4-1BB signaling domain; and (d) an intracellular CD3 zeta signaling domain, wherein (a)-(d) are in N to C terminal order. Uses of the chimeric antigen receptor, such as for treating a malignancy, are also disclosed.

30 Claims, 14 Drawing Sheets
Specification includes a Sequence Listing.

(56) References Cited

OTHER PUBLICATIONS

Chang et al, Humanization of an Anti-CCR4 Antibody That Kills CutaneousT-Cell Lymphoma Cells and Abrogates Suppression by T-Regulatory Cells,2012 supplemental figure 2, Molecular Cancer Therapeutics (Year: 2012).*
Chang et al, Humanization of an Anti-CCR4 Antibody That Kills CutaneousT-Cell Lymphoma Cells and Abrogates Suppression by T-Regulatory Cells,2012 , Molecular Cancer Therapeutics (Year: 2012).*
International Search Report from the parent PCT Application No. PCT/US2017/052437, 5 pages (dated Dec. 20, 2017).
Mihara et al., "All-trans retinoic acid and interferon-α increase CD38 expression on adult T-cell leukemia cells and sensitize them to T cells bearing anti-CD38 chimeric antigen receptors," *Blood Cancer Journal* 6:e421, 4 pages (May 13, 2016).
Perera et al., "Chimeric antigen receptor modified T cells that target chemokine receptor CCR4 as a therapeutic modality for T-cell malignancies," *Am J Hematol.* 92:892-901 (2017).
Perera et al., "Chimeric antigen receptor modified T cells that target chemokine receptor CCR4 as a therapeutic modality for T-cell malignancies," *3rd World Congress of Cutaneous Lymphomas Meeting* (Oct. 26-28, 2016) (Abstract).
Ratner, "Off-the-shelf CAR-T therapy induces remission in child with ALL," *Nature Biotechnology* 34(1): p. 12 (Jan. 2016).
Savoldo et al., "Epstein Barr virus—specific cytotoxic T lymphocytes expressing the anti-CD30ζ artificial chimeric T-cell receptor for immunotherapy of Hodgkin disease," *Blood* 110(7): 2620-2630 (e-Pub May 16, 2007).
Written Opinion from the parent PCT Application No. PCT/US2017/052437, 7 pages (dated Dec. 20, 2017).
Davila et al., "How do CARs work? Early insights from recent clinical studies targeting CD19," *OncoImmunology* 1(9): 1577-1583 (Dec. 2012).
Liu et al., "Affinity-tuned ErbB2 or EGFR chimeric antigen receptor T cells exhibit an increased therapeutic index against tumors in mice," *Cancer Research* 75(17): 3596-3607 (Sep. 1, 2015).
Sadelain et al., "The basic principles of chimeric antigen receptor design," *Cancer Discovery* 3(4); 388-398 (ePub Apr. 2, 2013).

* cited by examiner

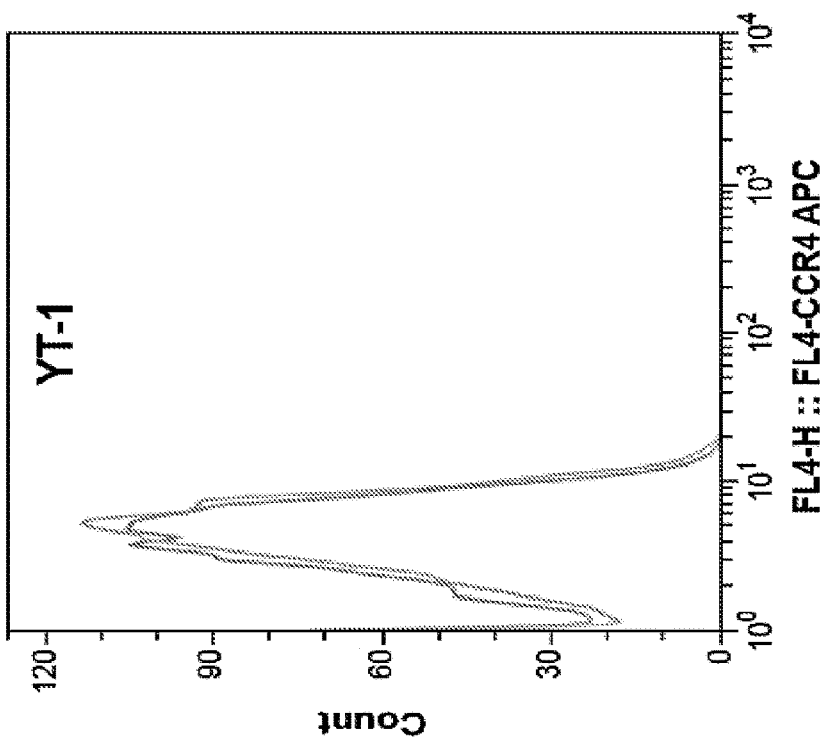
FIG. 2A
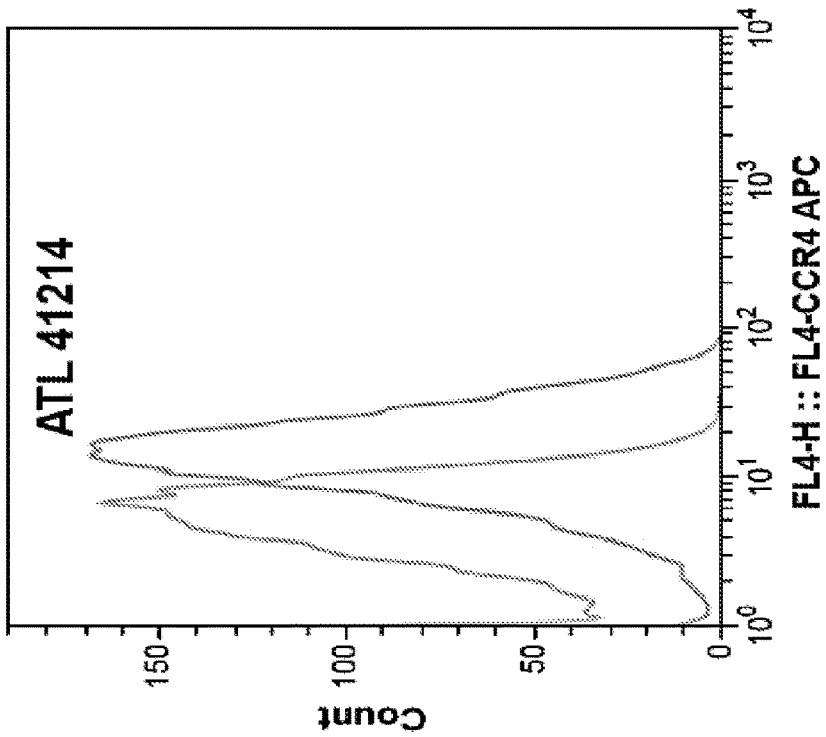

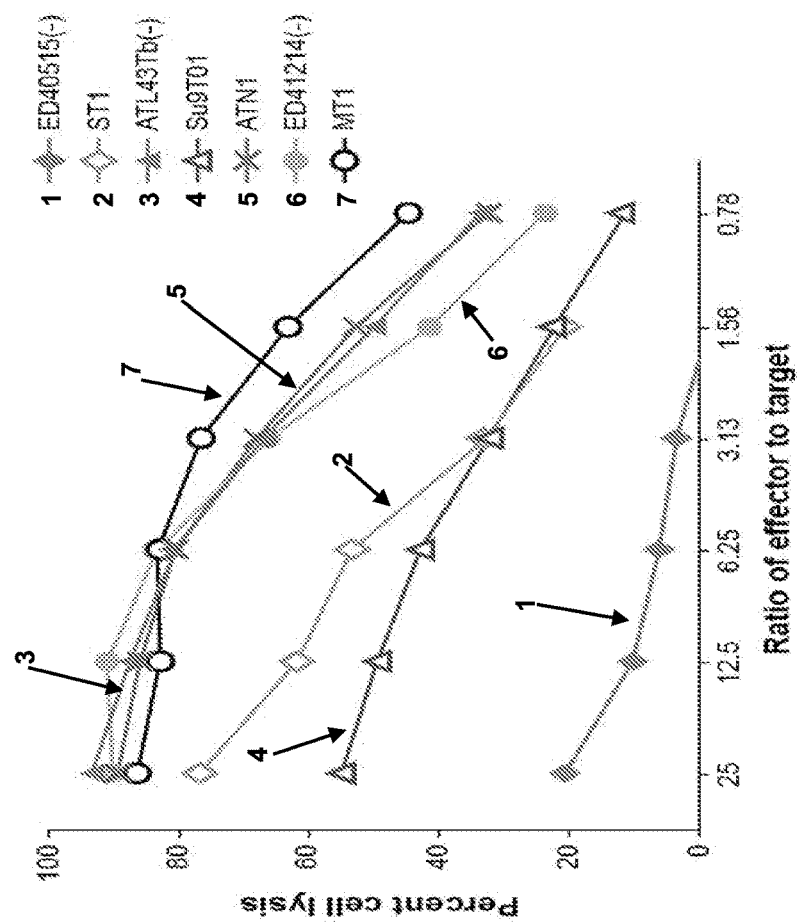
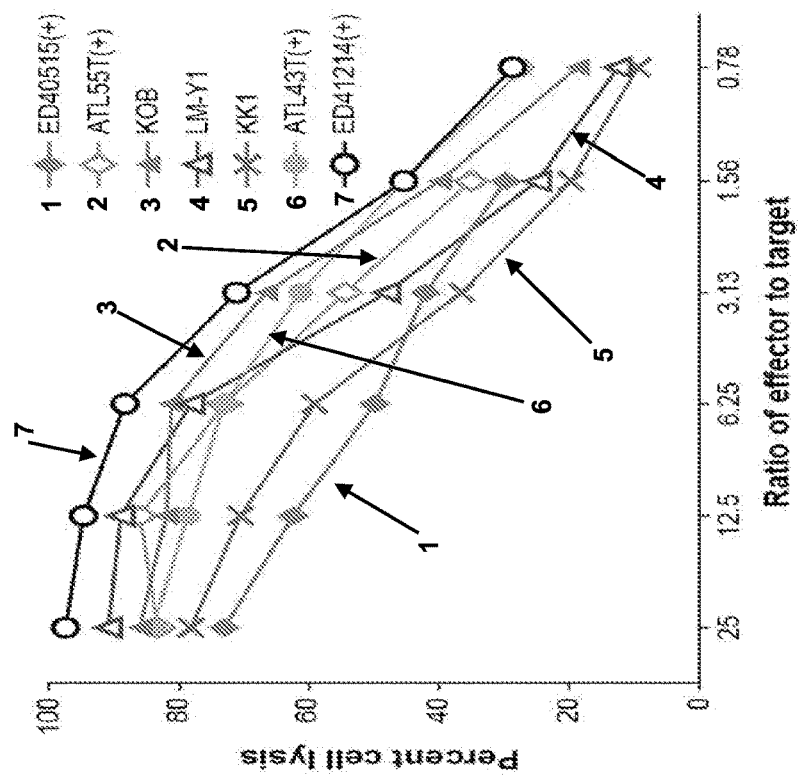
FIG. 3A
FIG. 3B

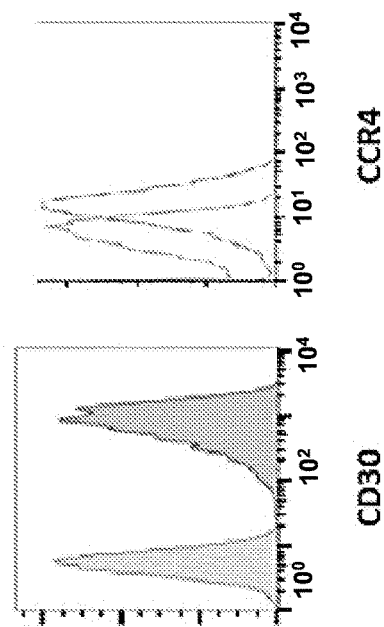
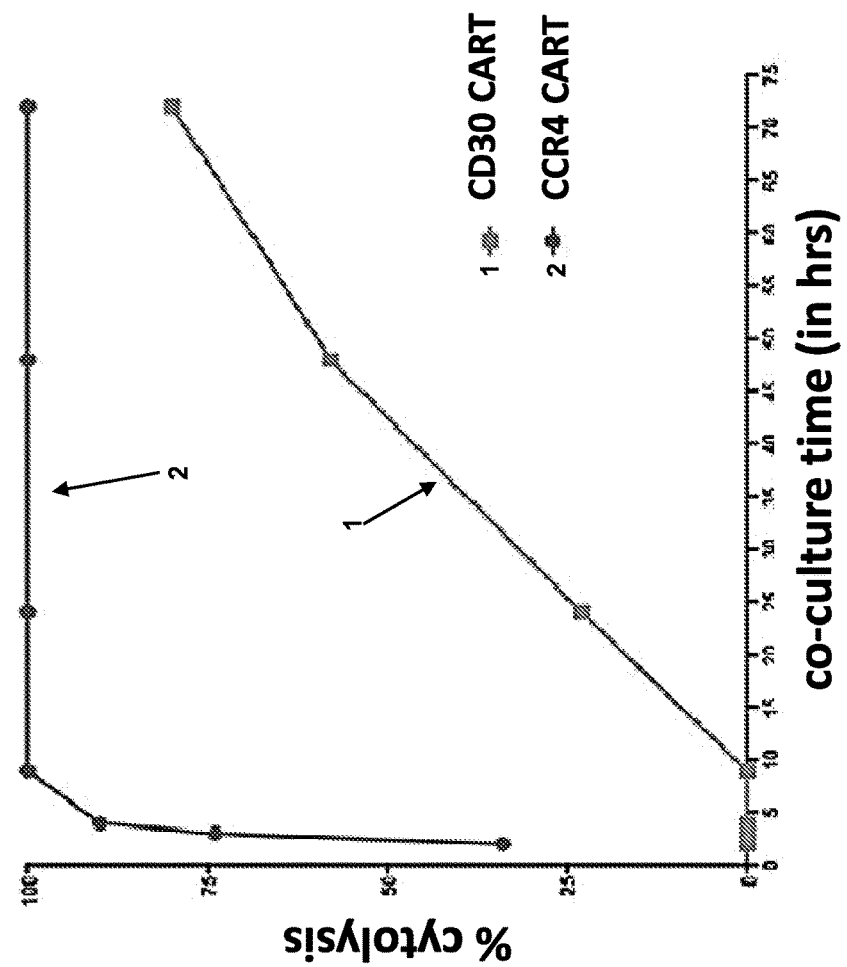
FIG. 7B
FIG. 7A

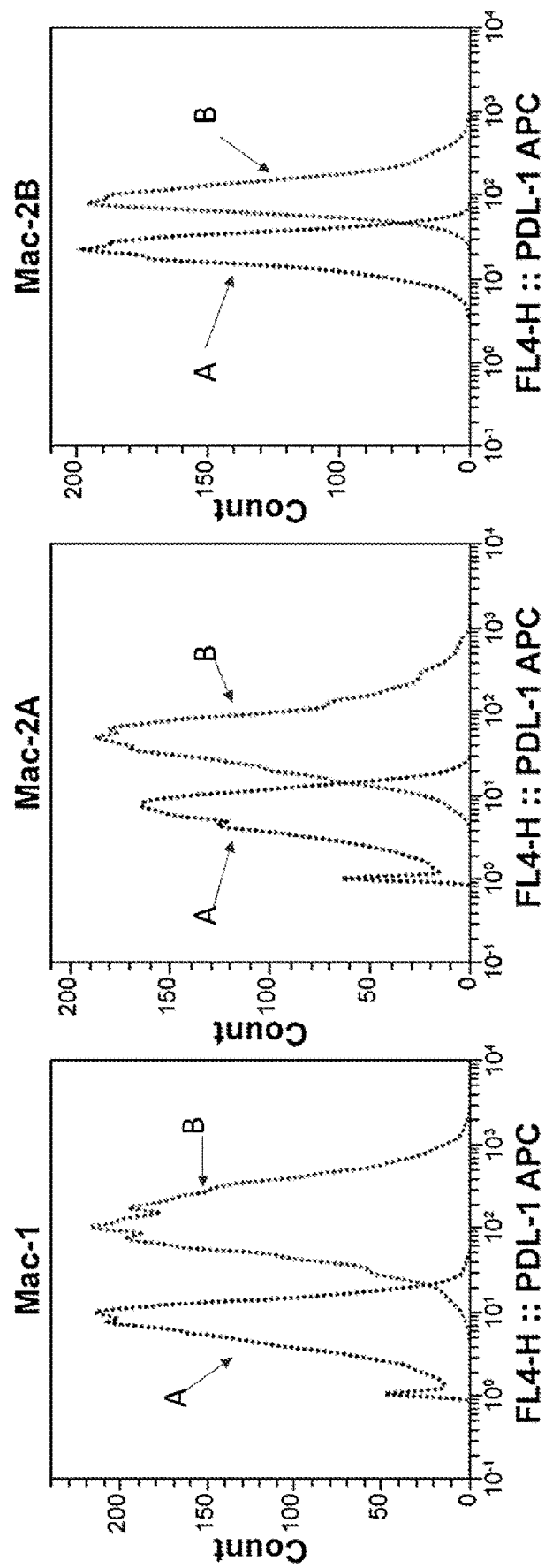

C=isotype control antibody; D=anti CCR4 antibody

```
                         SEQUENCE LISTING

<160> NUMBER OF SEQ ID NOS: 19

<210> SEQ ID NO 1
<211> LENGTH: 118
<212> TYPE: PRT
<213> ORGANISM: Artificial Sequence
<220> FEATURE:
<223> OTHER INFORMATION: VH of humanized affinity matured mAb1567

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Ala
                20                  25                  30

Trp Met His Trp Met Arg Gln Ala Pro Gly Gln Gly Leu Glu Trp Ile
            35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
                100                 105                 110

Leu Val Thr Val Ser Ser
            115

<210> SEQ ID NO 2
<211> LENGTH: 112
<212> TYPE: PRT
<213> ORGANISM: Artificial Sequence
<220> FEATURE:
<223> OTHER INFORMATION: VL of humanized affinity matured mAb1567

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
```

```
                85                  90                  95

Tyr Met Ser Ser Tyr Thr Phe Gly Gln Gly Thr Lys Leu Glu Ile Lys
            100                 105                 110

<210> SEQ ID NO 3
<211> LENGTH: 17
<212> TYPE: PRT
<213> ORGANISM: Artificial Sequence
<220> FEATURE:
<223> OTHER INFORMATION: Linker

<400> SEQUENCE: 3

Ser Ser Gly Gly Gly Gly Ser Gly Gly Gly Gly Ser Gly Gly Gly Gly
1               5                   10                  15

Ser

<210> SEQ ID NO 4
<211> LENGTH: 22
<212> TYPE: PRT
<213> ORGANISM: Artificial Sequence
<220> FEATURE:
<223> OTHER INFORMATION: Signal protein

<400> SEQUENCE: 4

Met Asp Phe Gln Val Gln Ile Phe Ser Phe Leu Leu Ile Ser Ala Ser
1               5                   10                  15

Val Ile Met Ser Arg Gly
            20

<210> SEQ ID NO 5
<211> LENGTH: 22
<212> TYPE: PRT
<213> ORGANISM: Artificial Sequence
<220> FEATURE:
<223> OTHER INFORMATION: Signal Protein

<400> SEQUENCE: 5

Leu Leu Val Thr Ser Leu Leu Leu Cys Glu Leu Pro His Pro Ala Phe
1               5                   10                  15

Leu Leu Ile Pro Asp Thr
            20

<210> SEQ ID NO 6
<211> LENGTH: 236
<212> TYPE: PRT
<213> ORGANISM: Artificial Sequence
<220> FEATURE:
<223> OTHER INFORMATION: Immunoglobulin Domain

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys Lys Asp Pro Lys
225                 230                 235

<210> SEQ ID NO 7
<211> LENGTH: 93
<212> TYPE: PRT
<213> ORGANISM: Artificial Sequence
<220> FEATURE:
<223> OTHER INFORMATION: CD8 Transmembrane Domain

<400> SEQUENCE: 7

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Phe Ala
50                  55                  60

Cys Asp Ile Tyr Ile Trp Ala Pro Leu Ala Gly Thr Cys Gly Val Leu
65                  70                  75                  80

Leu Leu Ser Leu Val Ile Thr Leu Tyr Cys Asn His Arg
                85                  90

<210> SEQ ID NO 8
<211> LENGTH: 42
<212> TYPE: PRT
<213> ORGANISM: Artificial Sequence
<220> FEATURE:
<223> OTHER INFORMATION: 4-1BB Signalling Domain

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 9
<211> LENGTH: 112
<212> TYPE: PRT
```

<213> ORGANISM: Artificial Sequence
<220> FEATURE:
<223> OTHER INFORMATION: CD3 zeta domain

<400> SEQUENCE: 9

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 10
<211> LENGTH: 516
<212> TYPE: PRT
<213> ORGANISM: Artificial Sequence
<220> FEATURE:
<223> OTHER INFORMATION: Chimeric Antigen Receptor

<400> SEQUENCE: 10

```
Met Asp Phe Gln Val Gln Ile Phe Ser Phe Leu Leu Ile Ser Ala Ser
1               5                   10                  15

Val Ile Met Ser Arg Gly Asp Ile Val Met Thr Gln Ser Pro Asp Ser
            20                  25                  30

Leu Ala Val Ser Leu Gly Glu Arg Ala Thr Ile Asn Cys Lys Ser Ser
        35                  40                  45

Gln Ser Ile Leu Tyr Ser Ser Asn Gln Lys Asn Tyr Leu Ala Trp Tyr
50                  55                  60

Gln Gln Lys Pro Gly Gln Ser Pro Lys Leu Leu Ile Tyr Trp Ala Ser
65                  70                  75                  80

Thr Arg Glu Ser Gly Val Pro Asp Arg Phe Ser Gly Ser Gly Ser Gly
                85                  90                  95

Thr Asp Phe Thr Leu Thr Ile Ser Ser Leu Gln Ala Glu Asp Val Ala
            100                 105                 110

Val Tyr Tyr Cys His Gln Tyr Met Ser Ser Tyr Thr Phe Gly Gln Gly
            115                 120                 125

Thr Lys Leu Glu Ile Lys Ser Ser Gly Gly Gly Ser Gly Gly Gly
        130                 135                 140

Gly Ser Gly Gly Gly Gly Ser Gln Val Gln Leu Val Gln Ser Gly Ala
145                 150                 155                 160

Glu Val Lys Lys Pro Gly Ala Ser Val Lys Val Ser Cys Lys Ala Ser
                165                 170                 175

Gly Tyr Thr Phe Ala Ser Ala Trp Met His Trp Met Arg Gln Ala Pro
            180                 185                 190

Gly Gln Gly Leu Glu Trp Ile Gly Trp Ile Asn Pro Gly Asn Val Asn
        195                 200                 205

Thr Lys Tyr Asn Glu Lys Phe Lys Gly Arg Ala Thr Leu Thr Val Asp
    210                 215                 220
```

-continued

```
Thr Ser Thr Asn Thr Ala Tyr Met Glu Leu Ser Ser Leu Arg Ser Glu
225                 230                 235                 240

Asp Thr Ala Val Tyr Tyr Cys Ala Arg Ser Thr Tyr Tyr Arg Pro Leu
            245                 250                 255

Asp Tyr Trp Gly Gln Gly Thr Leu Val Thr Val Ser Ser Ala Leu Ser
        260                 265                 270

Asn Ser Ile Met Tyr Phe Ser His Phe Val Pro Val Phe Leu Pro Ala
    275                 280                 285

Lys Pro Thr Thr Thr Pro Ala Pro Arg Pro Pro Thr Pro Ala Pro Thr
290                 295                 300

Ile Ala Ser Gln Pro Leu Ser Leu Arg Pro Glu Ala Cys Arg Pro Ala
305                 310                 315                 320

Ala Gly Gly Ala Val His Thr Arg Gly Leu Asp Phe Ala Cys Asp Ile
            325                 330                 335

Tyr Ile Trp Ala Pro Leu Ala Gly Thr Cys Gly Val Leu Leu Leu Ser
        340                 345                 350

Leu Val Ile Thr Leu Tyr Cys Asn His Arg Lys Arg Gly Arg Lys Lys
    355                 360                 365

Leu Leu Tyr Ile Phe Lys Gln Pro Phe Met Arg Pro Val Gln Thr Thr
370                 375                 380

Gln Glu Glu Asp Gly Cys Ser Cys Arg Phe Pro Glu Glu Glu Glu Gly
385                 390                 395                 400

Gly Cys Glu Leu Arg Val Lys Phe Ser Arg Ser Ala Asp Ala Pro Ala
            405                 410                 415

Tyr Gln Gln Gly Gln Asn Gln Leu Tyr Asn Glu Leu Asn Leu Gly Arg
        420                 425                 430

Arg Glu Glu Tyr Asp Val Leu Asp Lys Arg Arg Gly Arg Asp Pro Glu
    435                 440                 445

Met Gly Gly Lys Pro Arg Arg Lys Asn Pro Gln Glu Gly Leu Tyr Asn
450                 455                 460

Glu Leu Gln Lys Asp Lys Met Ala Glu Ala Tyr Ser Glu Ile Gly Met
465                 470                 475                 480

Lys Gly Glu Arg Arg Arg Gly Lys Gly His Asp Gly Leu Tyr Gln Gly
            485                 490                 495

Leu Ser Thr Ala Thr Lys Asp Thr Tyr Asp Ala Leu His Met Gln Ala
        500                 505                 510

Leu Pro Pro Arg
        515

<210> SEQ ID NO 11
<211> LENGTH: 66
<212> TYPE: DNA
<213> ORGANISM: Artificial Sequence
<220> FEATURE:
<223> OTHER INFORMATION: DNA encoding signal sequence

<400> SEQUENCE: 11
atggactttc aagtgcagat ctttagtttc ctgctcataa gcgctagtgt gatcatgtcc      60
agagga                                                                66

<210> SEQ ID NO 12
<211> LENGTH: 336
<212> TYPE: DNA
<213> ORGANISM: Artificial Sequence
<220> FEATURE:
<223> OTHER INFORMATION: DNA encoding VL of humanized affinity matured
      mAb1567
```

```
<400> SEQUENCE: 12
gatattgtga tgactcaaag ccccgacagt ctggccgtgt ctttgggcga gagagccaca      60
atcaactgca gtcctcaca gagtatcctt tattcctcta atcagaagaa ttacctcgca     120
tggtatcaac aaaaacccgg acagagccct aagcttttga tctattgggc atctacccga     180
gaatcaggag tgccggaccg cttcagtgga tcaggatcag gcacagactt tacgctgaca     240
atatcctctc ttcaggccga agacgttgcc gtgtactact gccatcaata tatgtcaagc     300
tacacattcg gccagggcac caaactcgag attaag                              336

<210> SEQ ID NO 13
<211> LENGTH: 354
<212> TYPE: DNA
<213> ORGANISM: Artificial Sequence
<220> FEATURE:
<223> OTHER INFORMATION: DNA encoding VH of humanized affinity matured
      mAb1567

<400> SEQUENCE: 13
caggttcagc tcgtgcaatc aggggcagag gtcaagaagc cgggtgcctc tgtgaaggtg      60
tcatgtaagg cctccgggta acttttgcc agcgcctgga tgcattggat gaggcaggcg     120
cccggccagg gtctggagtg gattggttgg attaatcccg aaacgtgaa tactaagtat     180 aacgagaagt ttaagggcag ggccacactc acagtcgaca caagcaccaa taccgcgtac     240
atggaacttt ccagcctccg gtccgaggac actgcggtgt attactgcgc acgctccacc     300
tattacagac cacttgatta ctgggggccaa gggaccctgg tgaccgtgtc tagc         354

<210> SEQ ID NO 14
<211> LENGTH: 51
<212> TYPE: DNA
<213> ORGANISM: Artificial Sequence
<220> FEATURE:
<223> OTHER INFORMATION: DNA encoding a linker

<400> SEQUENCE: 14
tctagtggtg gcggaggcag tggcggagga ggctccgggg gcggagggtc c               51

<210> SEQ ID NO 15
<211> LENGTH: 279
<212> TYPE: DNA
<213> ORGANISM: Artificial Sequence
<220> FEATURE:
<223> OTHER INFORMATION: DNA encoding CD8 domains

<400> SEQUENCE: 15
gcactcagca attccatcat gtacttctct catttcgtgc cagtatttct gcctgccaag      60
ccaactacca cacctgcgcc acgccctccc acgcccgcac ccacaattgc ttcacagcct     120
ctttctctgc ggcctgaggc ttgtcgccca gcagccggag gcgccgtgca tacgcgcggc     180
cttgacttcg catgtgacat ctacatttgg gctcctttgg ctggaacctg cggggtgttg     240
ttgcttagtc tggtgattac cctctactgc aatcataga                           279

<210> SEQ ID NO 16
<211> LENGTH: 126
<212> TYPE: DNA
<213> ORGANISM: Artificial Sequence
<220> FEATURE:
<223> OTHER INFORMATION: DNA encoding 4-1BB signaling molecule

<400> SEQUENCE: 16
```

| aagcgggggc gaaagaaact tctctatatc ttcaaacagc ctttcatgcg accagtgcag | 60 |
| acaacccaag aggaagacgg atgcagctgt cgctttccag aggaggaaga aggggggctgc | 120 |
| gagctg | 126 |

<210> SEQ ID NO 17
<211> LENGTH: 306
<212> TYPE: DNA
<213> ORGANISM: Artificial Sequence
<220> FEATURE:
<223> OTHER INFORMATION: DNA encoding a CD3 zeta domain

<400> SEQUENCE: 17

| agagtgaaat tctctcgctc cgctgacgcc cccgcgtatc aacagggcca gaatcagctc | 60 |
| tacaacgaac ttaaccttgg gcggagagaa gaatacgatg ttctcgacaa gcgcaggggg | 120 |
| agagaccctg agatgggcgg gaaaccgcgc cgcaagaacc cccaagaagg gttgtataac | 180 |
| gagctccaga aggacaaaat ggctgaagcc tactcagaga taggtatgaa gggcgagcgc | 240 |
| cgcagaggga agggacacga tggtctgtac caaggccttt caaccgccac caaggatacc | 300 |
| tatgat | 306 |

<210> SEQ ID NO 18
<211> LENGTH: 1565
<212> TYPE: DNA
<213> ORGANISM: Artificial Sequence
<220> FEATURE:
<223> OTHER INFORMATION: DNA encoding a chimeric antigen receptor

<400> SEQUENCE: 18

| gcggccgcat ggactttcaa gtgcagatct ttagtttcct gctcataagc gctagtgtga | 60 |
| tcatgtccag aggagatatt gtgatgactc aaagccccga cagtctggcc gtgtctttgg | 120 |
| gcgagagagc cacaatcaac tgcaagtcct cacagagtat cctttattcc tctaatcaga | 180 |
| agaattacct cgcatggtat caacaaaaac ccggacagag ccctaagctt ttgatctatt | 240 |
| gggcatctac ccgagaatca ggagtgccgg accgcttcag tggatcagga tcaggcacag | 300 |
| actttacgct gacaatatcc tctcttcagg ccgaagacgt tgccgtgtac tactgccatc | 360 |
| aatatatgtc aagctacaca ttcggccagg caccaaaact cgagattaag tctagtggtg | 420 |
| gcggaggcag tggcggagga ggctccgggg gcggagggtc ccaggttcag ctcgtgcaat | 480 |
| caggggcaga ggtcaagaag ccgggtgcct ctgtgaaggt gtcatgtaag gcctccgggt | 540 |
| atacttttgc cagcgcctgg atgcattgga tgaggcaggc gcccggccag ggtctggagt | 600 |
| ggattggttg gattaatccc ggaaacgtga atactaagta taacgagaag tttaagggca | 660 |
| gggccacact cacagtcgac acaagcacca ataccgcgta catggaactt ccagcctcc | 720 |
| ggtccgagga cactgcggtg tattactgcg cacgctccac ctattacaga ccacttgatt | 780 |
| actgggccca agggaccctg gtgaccgtgt ctagcgcact cagcaattcc atcatgtact | 840 |
| tctctcattt cgtgccagta tttctgcctg ccaagccaac taccacacct gcgccacgcc | 900 |
| ctcccacgcc cgcacccaca attgcttcac agcctctttc tctgcggcct gaggcttgtc | 960 |
| gcccagcagc cggaggcgcc gtgcatacgc gcggccttga cttcgcatgt gacatctaca | 1020 |
| tttgggctcc tttggctgga acctgcgggg tgttgttgct tagtctggtg attaccctct | 1080 |
| actgcaatca tagaaagcgg gggcgaaaga aacttctcta tatcttcaaa cagcctttca | 1140 |
| tgcgaccagt gcagacaacc caagaggaag acggatgcag ctgtcgcttt ccagaggagg | 1200 |

```
aagaaggggg ctgcgagctg agagtgaaat tctctcgctc cgctgacgcc cccgcgtatc    1260
aacagggcca gaatcagctc tacaacgaac ttaaccttgg gcggagagaa gaatacgatg    1320
ttctcgacaa gcgcagggg agagaccctg agatgggcgg gaaaccgcgc cgcaagaacc     1380
cccaagaagg gttgtataac gagctccaga aggacaaaat ggctgaagcc tactcagaga    1440
taggtatgaa gggcgagcgc cgcagaggga agggacacga tggtctgtac caaggccttt    1500
caaccgccac caaggatacc tatgatgcac tgcacatgca agccctgcct cctcgctaag    1560
gatcc                                                                1565

<210> SEQ ID NO 19
<211> LENGTH: 67
<212> TYPE: PRT
<213> ORGANISM: Artificial Sequence
<220> FEATURE:
<223> OTHER INFORMATION: CD28 transmembrane domain

<400> SEQUENCE: 19

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg
65
```

CHIMERIC ANTIGEN RECEPTOR (CAR) THAT TARGETS CHEMOKINE RECEPTOR CCR4 AND ITS USE

CROSS REFERENCE TO RELATED APPLICATION

This is a § 371 U.S. national stage of International Application No. PCT/US2017/052437, filed Sep. 20, 2017, which was published in English under PCT Article 21(2), and which application claims the benefit of U.S. Provisional Application No. 62/397,810, filed Sep. 21, 2016, which is incorporated by reference herein in its entirety.

FIELD OF THE DISCLOSURE

This relates to the field of malignancies, specifically to a chimeric antigen receptor that specifically binds CCR4 and its use for treatment, such as to treat a malignancy in a subject.

BACKGROUND

C—C motif chemokine receptor 4 (CCR4) is a seven trans-membrane G protein-coupled cell surface receptor molecule (alternatively designated CD194) with selective expression on cells of the hematopoietic system (Yoshie and Matsushima, *Int Immunol.* 2015; 27(1):11-20; Solari and Pease, *Eur J Pharmacol.* 2015; pii: S0014-2999(15)30011). In the peripheral blood of healthy individuals, $CD4^+CD25^+$ $Foxp3^+$ T regulatory (Treg) cells, $T_{H2}$ and $T_{H17}$ T cells as well as platelets display a preponderance of CCR4 expression (Hirahara et al., *J Immunol.* 2006; 177(7):4488-4494; D'Ambrosio et al., *J Immunol.* 1998; 161(10):5111-5115; Annunziato et al., *J Exp Med.* 2007; 204(8):1849-1861; Clemetson et al., *Blood.* 2000; 96(13):4046-4054; Abi-Younes et al., *Thromb Res.* 2001; 101(4):279-289). As seen with other chemokine receptors, although CCR4 displays some level of promiscuity in its ligand specificity, the C-C chemokines CCL17 and CCL22 are the primary, high affinity ligands of this receptor, while MCP-1, MIP-1 and RANTES also show significant ligand activity (Andrew et al., *J Immunol.* 1998; 161(9):5027-5035; Imai et al., *J Biol Chem.* 1998; 273(3):1764-1768; Zlotnik et al., *Immunity.* 2000; 12(2):121-127). The aberrant over-expression of CCL17 and CCL22 especially by stromal cells is seen in a variety of neoplasms including, breast, ovarian, gastric, and esophageal cancers and in lymphoid malignancies such as Hodgkin's disease (Gobert et al., *Cancer Res.* 2009; 69(5): 2000-2009; Fialová A et al., *Int J Cancer.* 2013; 132(5): 1070-1079; Curiel et al., *Nat Med.* 2004; 10(9):942-949; Yang et al.; *PLoS One.* 2015; 10(3):e0120059; Maruyama et al., *Dis Esophagus* 2010; 23(5):422-429; Ishida et al., *Cancer Res.* 2006; 66(11):5716-5722). This is the primary driver for the extensive influx of CCR4 bearing Tregs into the tumor micro-environment of such malignancies that not only impede effective anti-tumor immune responses but also promote tumor trafficking and metastasis as well (Tsujikawa et al.; *Int J Cancer.* 2013; 132(12):2755-2766).

In adult T cell leukemia (ATL), an HTLV-1 associated T cell malignancy often considered to be a $CD4^+$ Treg disorder, the cell-surface expression of CCR4 on leukemic cells is near universal (Yoshie et al., *Blood.* 2002; 99(5):1505-1511; Ishida et al; *Clin Cancer Res.* 2003; 9(10 Pt 1):3625-3634). Moreover, in a majority of cutaneous T cell lymphomas [peripheral T-cell lymphoma (PTCL)/cutaneous T-cell lymphoma (CTCL), mycosis fungoides (MF)/Sezary syndrome (SS)], the homing of malignant cells to the skin is primarily dictated by the cell-surface-expressed CCR4 (Hristov et al., *Am J Clin Pathol.* 2011; 136(6):944-953; Kakinuma et al., *J Am Acad Dermatol.* 2003; 48(1):23-30). A significant proportion of anaplastic large cell lymphomas (ALCL), and other peripheral T-cell lymphomas also express CCR4 receptors perhaps as a consequence of the aberrant expression of the $T_H2$ master transcriptional regulator GATA-3 in these tumors. The presence of CCR4 in these tumors has shown to be an independent prognostic factor of poor survival in both peripheral T-cell lymphoma-not otherwise specified (PTCL-NOS) and anaplastic lymphoma kinase (ALK) negative ALCL by a multivariate analysis (Vermeer et al., *Mod Pathol.* 2002 August; 15(8): 838-844; Wang et al., *Blood.* 2014; 123(19):3007-3015; Iqbal et al. *Blood.* 2014; 123(19):2915-2923; Percy et al. International Classification of Diseases for Oncology (ICD-O-3) $3^{rd}$ ed. Geneva, Switzerland: World Health Organization; 2000).

Mogamulizumab is a defucosylated humanized antibody engineered to exert enhanced antibody-dependent cytotoxicity that targets CCR4 and is approved in Japan for the treatment of relapsed or refractory adult T-cell leukemia/lymphoma (Subramaniam et al., *Drugs.* 2012; 72(9):1293-1298) and accumulating evidence reveals considerable efficacy of this modality even in heavily pretreated patients (Oruga et al., *J Clin Oncol.* 2014; 32(11):1157-1163). The observed adverse events are primarily of hematologic nature in addition to pyrexia and skin disorders that are not only manageable but are also reversible (Ogura et al., *J Clin Oncol.* 2014; 32(11):1157-1163; Duvic et al., *Blood.* 2015; 125(12):1883-1889.). Equally important, mogamulizumab therapy also selectively depletes effector type $Foxp3^+CD4^+$ Tregs resulting in the induction of heightened anti-tumor responses in the treated patients (Sugiyarna et al., *Proc Nati Acad Sci USA* 2013; 110(44):17945-17950; Ni et al., *Clin Cancer Res.* 2015; 21(2):274-285). Thus, a need remains for other therapeutic agents that target CCR4, such as for the treatment of adult T cell leukemia, cutaneous T cell lymphoma, anaplastic large cell lymphoma, and other lymphomas that express CCR4.

SUMMARY OF THE DISCLOSURE

In some embodiments, a chimeric antigen receptor is disclosed that includes: (a) an scFv including a light chain variable domain ($V_L$) and a heavy chain variable domain ($V_H$) of the mAB2-3 antibody, wherein the scFv specifically binds to CCR4; (b) a hinge and transmembrane domain from CD8; (c) an intracellular 4-1BB signaling domain; and (d) an intracellular CD3 zeta signaling domain, wherein (a)-(d) are in N-terminal to C-terminal order. In some embodiments, and signal sequence, such as but not limited to the mouse immunoglobulin signal sequence, is included N-terminal to the scFv. In specific non-limiting examples, the heavy chain variable domain comprises a heavy chain complementarity determining region (HCDR)1, an HCDR2 and an HCDR3, wherein the HCDR1 comprises amino acids 26-33 of SEQ ID NO: 1, the HCDR2 comprises amino acids 51-58 of SEQ ID NO: 1, and the HCDR3 comprises amino acids 99-107 of SEQ ID NO: 1, and wherein the light chain variable domain comprises a light chain complementarity determining region (LCDR)1, a LCDR2 and a LCDR3, wherein the LCDR1 comprises amino acids 27-38 of SEQ ID NO: 2, the LCDR2 comprises amino acids 56-61 of SEQ ID NO: 2, and the LCDR3 comprises amino acids 95-102 of SEQ ID NO: 2.

In some embodiments, disclosed are nucleic acid molecules and expression vectors encoding these CARs. In specific non-limiting examples, the expression vectors can be lentiviral vectors or gamma retroviral vectors. Alternatively it can also be a complete mRNA molecule encoding the CAR by RNA transfection. Host cells transformed with these vectors are also disclosed, such as T cells and natural killer (NK) cells.

In additional embodiments, methods are disclosed for treating a subject with a lymphoid that produces CCR4 mRNA. In some non-limiting examples, the methods include transducing CD3+ T cells and/or natural killer (NK) cells with an expression vector encoding the CAR to produce transduced T cells and/or NK cells that express the chimeric antigen receptor. A therapeutically effective amount of the transduced cells that express the chimeric antigen receptor are administered to the subject to treat the malignancy. In specific non-limiting examples, the malignancy is a lymphoid malignancy. In other specific non-limiting examples, the cells are autologous.

The foregoing and other features and advantages of the invention will become more apparent from the following detailed description of several embodiments which proceeds with reference to the accompanying figures.

BRIEF DESCRIPTION OF THE FIGURES

FIGS. 2A-2D: Kinetics, potency and durability of target cell lysis activity of in vitro expanded CCR4 CAR T cells. The cell line ATL41214 has been derived from a patient with HTLV-1 associated chronic adult T cell leukemia and YT-1 cell line that has been derived from a patient with EBV associated NK lymphoma. The surface expression of CCR4 on these two cell lines were determined by flow cytometry using an anti-human CCR4-APC antibody (clone D8SEE from EBIOSCENCE®) depicted in red or an isotype matched control antibody depicted in blue (panel A). CAR T cells that were expanded in vitro for 12 days following lentiviral transduction in the presence of IL-2, and CD3/CD28 microbeads were co-cultured with ATL41214 cells that have been tagged with luciferase (ATL41214/Luc) in triplicate at indicated effector:target ratios for indicated duration of time. The percentage of cell lysis was calculated as indicated in the Methods section after the addition of D-luciferin and measuring bioluminescence using a microplate counter/luminometer. (Panel B) Long term retention of lytic activity was determined by in vitro expansion of CAR T cells for a period of 8 weeks as described in the Methods section and then co-culturing with ATL41214/Luc target cells for a period of 20 hours at indicated effector:target ratios shown on the x-axis (panel C). Experiment in panel B was replicated with YT-1 cells that have been tagged with luciferase in an identical manner in panel D.

FIGS. 3A-3E: CCR4 CAR T cells show potent activity against tumor cells derived from a spectrum of T cell malignancies. In vitro expanded CAR T cells (12-day expansion) were co-cultured with (A) IL-2 dependent ATL cell lines derived from patients with acute ATL. (B) IL-2 independent ATL cell lines derived from patients with chronic/smoldering form of ATL. (C) Cell lines derived from patients with cutaneous T cell lymphoma including Sézary disease and mycosis fungoides. (D) Cell lines derived from patients with anaplastic large cell lymphoma either with ALK-positive (JB-6, Karpas299, SUDHL-1, SR-786, SUP-M2, and DEL) or ALK-negative (Mac-1, Mac2-A, Mac2B) subtype. SUDHL-4 cell line derived from a diffuse large B cell lymphoma was included as well. (E) Cell lines derived from patients with Hodgkin's lymphoma. Percent cell lysis was determined using a standard 4-hour $^{51}Cr$-release assay performed in triplicate (Phillips et al., *Cancer Res.* 2000; 60(24):6977-6984).

FIGS. 7A-7B: CCR4 CAR T cells kill ATL 41214/Luc cells with faster kinetics: The ATL 41214/Luc cell line was used as target cells in a co-culture experiment in which either CCR4 CAR T cells or CD30 CAR T cells were assessed for their ability to kill these cells. Target and effector cells were mixed in a 1:1 ratio and co-cultured for indicated lengths of time. The percent cell killing was calculated as indicated in the Example 1 by a bioluminescence assay (panel A). The surface expression levels of CD30 and CCR4 on ATL 41214/Luc were measured by flow cytometry (panel B) where staining by isotype control antibodies are depicted in blue and CD30 antibody or CCR4 antibody staining is depicted in red.

FIGS. 8A-8B: CCR4 CAR T cells can kill targets that express CCR4, including targets that express high levels of PDL-1 inhibitory molecule, implicated as a mechanism whereby tumors could evade CAR T cell activity by debilitating the functionality of CAR T cells via PDL-1/PD-1 interaction. Anaplastic large cell lymphomas (ALCL) universally express high levels of surface PDL-1 (A) and at the same time ALK negative subtype of ALCL which are more aggressive also express high levels of CCR4(B). ALK negative ALCL lines express high levels of PDL-1 as expected but the same cell lines were highly susceptible to killing by CCR4 CAR T cells as shown in FIG. 3D above.

SEQUENCE LISTING

Figure 1A:
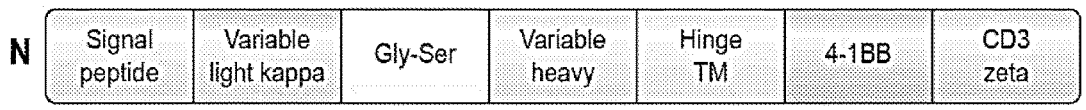
FIGS. 1A-1E: Construction and characterization CCR4 CAR. (A) Schematic representation of the domain configuration of CCR4 CAR polypeptide. (B) Transduction efficiency CCR4 CAR lentiviral vector was assessed by flow cytometry after a single transduction event of donor-derived, in-vitro activated human $CD3^+$ T lymphocytes by measuring the percentage of GFP positive T cells. (C) Cell surface expression of CCR4 CAR on transduced $CD3^+$ T cells was detected by binding of protein L and the concordance with GFP expression by flow cytometry. (D) Percentage of $CD4^+$ and (E) percentage of $CD8^+$ T cells that express CCR4 CAR, 72 hours after lentiviral transduction of in vitro activated, $CD3^+$ donor derived lymphocytes. Percentage is noted in the top-right quadrant.
Figure 1B:
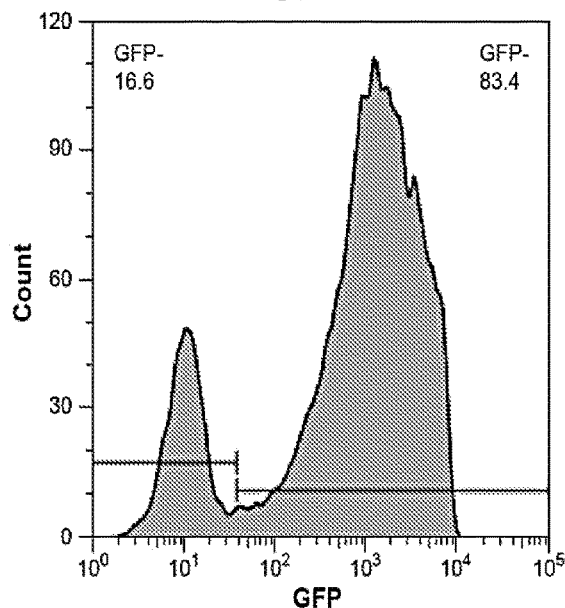
Figure 1C:
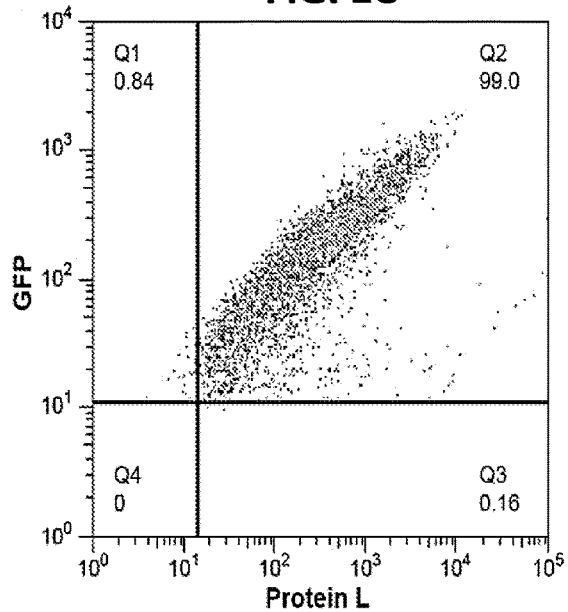
Figure 1D:
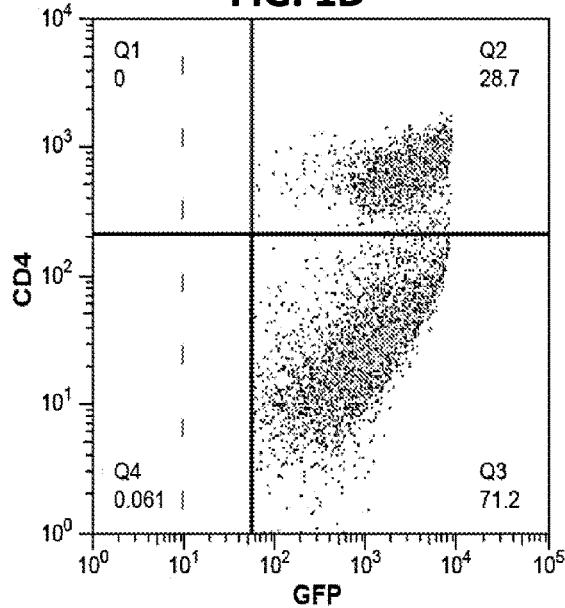
Figure 1E:
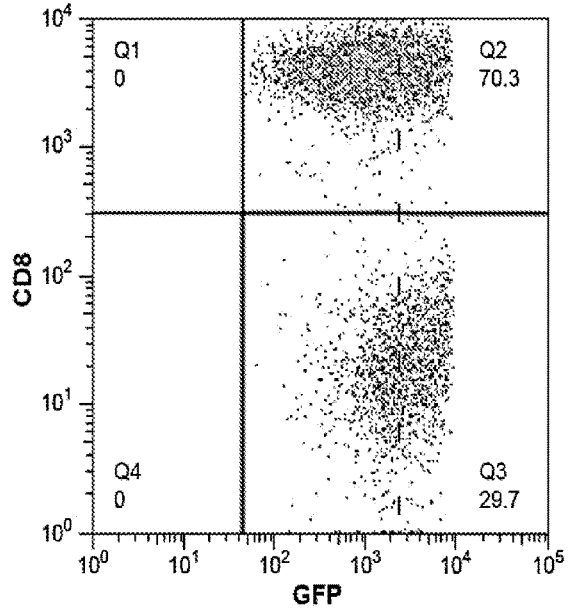

The nucleic and amino acid sequences are shown using standard letter abbreviations for nucleotide bases, and one letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Feb. 12, 2019, 18.3 KB, which is incorporated by reference herein. In the accompanying sequence listing:

SEQ ID NO: 1 is the amino acid sequence of the $V_H$ of humanized affinity matured mAb1567.

SEQ ID NO: 2 is the amino acid sequence of the $V_L$ of humanized affinity matured mAb1567.

SEQ ID NO: 3 is the amino acid sequence of a linker.

SEQ ID NOs: 4-5 are the amino acid sequence of signal sequences.

SEQ ID NO: 6 is the amino acid sequence of an immunoglobulin domain that can be used as a spacer.

SEQ ID NO: 7 is the amino acid sequence of a CD8 transmembrane domain

SEQ ID NO: 8 is the amino acid sequence of a 4-1BB signaling domain.

SEQ ID NO: 9 is the amino acid sequence of a CD3 zeta domain.

SEQ ID NO: 10 is the amino acid sequence of an exemplary CAR.

SEQ ID NO: 11 is a nucleic acid sequence encoding a signal sequence.

SEQ ID NO: 12 is a nucleic acid sequence encoding $V_L$ of humanized affinity matured mAb1567.

SEQ ID NO: 13 is a nucleic acid sequence encoding $V_H$ of humanized affinity matured mAb1567.

SEQ ID NO: 14 is a nucleic acid sequence encoding a linker.

SEQ ID NO: 15 is a nucleic acid sequence encoding a CD8 hinge and transmembrane domain.

SEQ ID NO: 16 is a nucleic acid sequence encoding a 4-1BB signaling molecule.

SEQ ID NO: 17 is a nucleic acid sequence encoding a CD3 zeta domain.

SEQ ID NO: 18 is a nucleic acid sequence encoding a CAR.

SEQ ID NO: 19 is an exemplary CD28 transmembrane domain.

DETAILED DESCRIPTION OF SEVERAL EMBODIMENTS

A gene transfer system was produced and used to genetically engineer autologous T cells to express a chimeric antigen receptor (CAR) that targets CCR4 using humanized variable heavy (VH) and kappa light (VL) chain moieties derived from an anti-CCR4 antibody. The CAR was introduced into T cells, which were documented to target cells of several malignancies, specifically lymphoid malignancies. Donor T cells modified ex-vivo with the CCR4 targeting CAR were shown to efficiently lysed patient-derived tumor cell lines that expressed CCR4 in an antigen-specific manner and in vivo efficacy was demonstrated in a model of adult T cell leukemia.

Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Adult T cell leukemia (ATL): ATL is usually a highly aggressive non-Hodgkin's lymphoma with no characteristic histologic appearance except for a diffuse pattern and a mature T-cell phenotype. Circulating lymphocytes with an irregular nuclear contour (leukemic cells) are frequently seen. Several lines of evidence suggest that HTLV-1 causes ATL. ATL is frequently accompanied by visceral involvement, hypercalcemia, skin lesions, and lytic bone lesions. One of the features of is that the bone lesions are predominantly osteolytic with little associated osteoblastic activity. There are four forms of ATL, chronic, acute, smoldering and lymphomatous.

Amino acid substitution: The replacement of one amino acid in peptide with a different amino acid.

Anaplastic large cell lymphoma: a type of non-Hodgkin lymphoma involving aberrant T-cells. There are four subtypes, all of which include the presence of large pleomorphic cells that express CD30 and T-cell markers. Two types of ALCL present as systemic disease and are considered as aggressive lymphomas, while two types present as localized disease and may progress locally. Cutaneous ALCL is a tumor that presents in the skin as ulcers that may persist, or occasionally may involute spontaneously, and commonly recur. This type of ALCL usually manifest in different regions of the body and may extend to regional lymph nodes, i.e., an axillary lymph node if the ALCL presents in the arm.

Antibody: An immunoglobulin, antigen-binding fragment, or derivative thereof, that specifically binds and recognizes an analyte (antigen) such as IL-7Rα. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used. In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, $3^{rd}$ Ed., W. H. Freeman & Co., New York, 1997.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

An antibody may have one or more binding sites. If there is more than one binding site, the binding sites may be identical to one another or may be different. For instance, a naturally occurring immunoglobulin has two identical binding sites, a single-chain antibody or Fab fragment has one binding site, while a bispecific or bifunctional antibody has two different binding sites.

Typically, a naturally occurring immunoglobulin has heavy chains and light chains interconnected by disulfide bonds Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W. H. Freeman and Co., page 91 (2007).) In several embodiments, the $V_H$ and $V_L$ combine to specifically bind the antigen. In additional embodiments, only the $V_H$ is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are sometimes referred to as LCDR1, LCDR2, and LCDR3. Heavy chain CDRs are sometimes referred to as HCDR1, HCDR2, and HCDR3.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions, which have substantially no effect on antigen binding or other immunoglobulin functions. (See, for example, Harlow & Lane, *Antibodies, A Laboratory Manual*, $2^{nd}$ ed. Cold Spring Harbor Publications, N.Y. (2013).)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, and are typically of different species. In some examples, a chimeric antibody includes one or more CDRs and/or framework regions from one human antibody and CDRs and/or framework regions from another human antibody. In other embodiments, a chimeric antibody can include the VH and VL regions of a mouse monoclonal antibody (such as the 4A10 or 2B8 antibody) and human constant regions, such as human IgG1 regions.

A "fully human antibody" or "human antibody" is an antibody, which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel*. $1^{st}$ Ed. New York: Cold Spring Harbor Laboratory Press, 2004. Print.; Lonberg, *Nat. Biotech.*, 23: 1117-1125, 2005; Lonenberg, *Curr. Opin. Immunol.*, 20:450-459, 2008).

Biological sample: A sample obtained from a subject. Biological samples include all clinical samples useful for detection of disease (for example, a lymphoid malignancy) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a lymphoid malignancy.

CC-chemokine receptor type 4 (CCR4): Also known as CD194, CCR4 is one of the CC-chemokine receptors. An exemplary mRNA nucleic acid sequence and the encoded protein sequence for human CCR4 is GENBANK® Accession No. NM_005508, Mar. 18, 2016, which is incorporated herein by reference. An exemplary mRNA nucleic acid sequence and the encoded protein sequence for mouse CCR4 is GENBANK® Accession No. NM_009916, Jul. 19, 2015, which is incorporated herein by reference.

CD3 (Cluster of differentiation 3 T cell Co-receptor): A specific protein complex including at least four polypeptide chains, which are non-covalently associated with the T cell receptors on the surface of T cells. The four polypeptide chains include two CD3-epsilon chains, a CD3-delta chain and a CD3-gamma chain. CD3 is present on both helper T cells and cytotoxic T cells.

Chemotherapeutic agent: Any chemical agent with therapeutic usefulness in the treatment of diseases characterized by abnormal cell growth. For example, chemotherapeutic agents can be useful for the treatment of cancer, such as T-ALL or B-ALL. Particular examples of chemotherapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993; Chabner and Longo, *Cancer Chemotherapy and Biotherapy: Principles and Practice* (4th ed.). Philadelphia: Lippincott Willians & Wilkins, 2005; Skeel, *Handbook of Cancer Chemotherapy* (6th ed.). Lippincott Williams & Wilkins, 2003). Combination chemotherapy is the administration of more than one agent to treat cancer.

Chimeric Antigen Receptor (CAR): An engineered T cell receptor having an extracellular antibody-derived targeting domain (such as an scFv) joined to one or more intracellular signaling domains of a T cell receptor. A "chimeric antigen receptor T cell" is a T cell expressing a CAR, and has antigen specificity determined by the antibody-derived targeting domain of the CAR. Methods of making CARs are available (see, e.g., Park et al., *Trends Biotechnol.*, 29:550-

557, 2011; Grupp et al., N Engl J Med., 368:1509-1518, 2013; Han et al., J. Hematol Oncol., 6:47, 2013; PCT Publication Nos. WO2012/079000, WO2013/059593; and U.S. Publication No. 2012/0213783, each of which is incorporated by reference herein in its entirety.)

Codon Optimized: A nucleic acid molecule encoding a protein can be codon optimized for expression of the protein in a particular organism by including the codon most likely to encode a particular amino acid with the amino acid sequence. Codon usage bias is the differences in the frequency of occurrence of synonymous codons (encoding the same amino acid) in coding DNA. A codon is a series of three nucleotides (a triplet) that encodes a specific amino acid residue in a polypeptide chain or for the termination of translation. There are 20 different naturally-occurring amino acids, but 64 different codons (61 codons encoding for amino acids plus 3 stop codons). Thus, there is degeneracy because one amino acid can be encoded by more than one codon. A nucleic acid sequence can be optimized for expression in a particular organism (such as a human) by evaluating the codon usage bias in that organism and selecting the codon most likely to encode a particular amino acid. Multivariate statistical methods, such as correspondence analysis and principal component analysis, are widely used to analyze variations in codon usage. Computer programs are available to implement the statistical analyses related to codon usage, such as Codon W, GCUA, and INCA.

Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane (Antibodies, *A Laboratory Manual*, $2^{nd}$ ed. Cold Spring Harbor Publications, N.Y., 2013) for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography Immunological binding properties of selected antibodies may be quantified using methods well known in the art.

Conservative variants: "Conservative" amino acid substitutions are those substitutions that do not substantially affect or decrease a function of a protein, such as the ability of the protein to interact with a target protein. For example, an IL-7Rα-specific antibody can include up to 1, 2, 3, 4, 5, 6, 7, 8, 9, or up to 10 conservative substitutions compared to a reference antibody sequence and retain specific binding activity for IL-7Rα. The term conservative variation also includes the use of a substituted amino acid in place of an unsubstituted parent amino acid.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the IL-7Rα-specific antibody, such as the ability to specifically bind to IL-7Rα. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as sample obtained from a healthy patient that does not have a particular malignancy. In other embodiments, the control is a positive control, such as a tissue sample obtained from a patient diagnosed with the malignancy. In still other embodiments, the control is a historical control or standard reference value or range of values (such as a previously tested control sample, such as a group of patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Cutaneous T cell lymphoma: A class of non-Hodgkin lymphoma caused by T cells. The malignant T cells initially migrate to the skin, causing various lesions to appear. These lesions change shape as the disease progresses, typically beginning as what appears to be a rash and eventually forming plaques and tumors before metastasizing to other parts of the body. Cutaneous T cell lymphoma includes mycosis fungoides, pagetoid reticulosis, Sézary syndrome, granulomatous slack skin, lymphomatoid papulosis, pityriasis lichenoides chronica, pityriasis lichenoides et varioliformis acuta, CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma, angiocentric lymphoma, and blastic NK-cell lymphoma.

Degenerate variant: In the context of the present disclosure, a "degenerate variant" refers to a polynucleotide encoding a protein (for example, an CAR that specifically recognizes CCR4) that includes a sequence that is degenerate as a result of the genetic code. There are twenty natural amino acids, most of which are specified by more than one codon. Therefore, all degenerate nucleotide sequences are included as long as the amino acid sequence of the CAR encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, N.Y., through supplement 104, 2013).

Detecting: To identify the existence, presence, or fact of something, such as the existence of a malignancy, such as a lymphoid malignancy, or an HIV infection. General methods of detecting are known to the skilled artisan and may be supplemented with the protocols and reagents disclosed herein.

Diffuse large B cell lymphoma: The most common type of non-Hodgkin lymphoma among adults. The first sign of this illness is typically the observation of a rapidly growing mass, sometimes associated with fever, weight loss, and night sweats. Within cellular morphology three variants are most commonly seen: centroblastic, immunoblastic, and anaplastic. Most cases of diffuse large B cell lymphoma are centroblastic, having the appearance of medium-to-large-sized lymphocytes with scanty cytoplasm. Oval or round nuclei containing fine chromatin are prominently visible, having two to four nucleoli within each nucleus. Sometimes the tumor may be monomorphic, composed almost entirely of centroblasts. However, most cases are polymorphic, with a mixture of centroblastic and immunoblastic cells Immunoblasts have significant basophilic cytoplasm and a central nucleolus. A tumor can be classified as immunoblastic if greater than 90% of its cells are immunoblasts. Anaplastic lymphoma consists of tumor cells which appear very differently from their normal B cell counterparts. The cells are generally very large with a round, oval, or polygonal shape and pleomorphic nuclei, and may resemble Reed-Sternberg cells.

Drug: Any compound used to treat, ameliorate or prevent a disease or condition in a subject. In some embodiments herein, the drug is a chemotherapeutic agent.

Epitope: An antigenic determinant These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on CCR4.

Expression: Transcription or translation of a nucleic acid sequence. For example, a gene can be expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence, which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc polypeptide: The polypeptide including the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region includes immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to include residues C226 or P230 to its carboxyl-terminus, wherein the numbering is according to the EU index in Kabat. For IgA, the Fc region includes immunoglobulin domains Calpha2 and Calpha3 (Cα2 and Cα3) and the lower part of the hinge between Calpha1 (Cα1) and Cα2.

Hodgkin's lymphoma: A type of B cell lymphoma, about half of which are due to Epstein-Barr virus infection. There are two major types of Hodgkin lymphoma: classical Hodgkin lymphoma and nodular lymphocyte-predominant Hodgkin lymphoma. Diagnosis is by finding Hodgkin's cells such as multinucleated Reed-Sternberg cells (RS cells) in lymph nodes. Classical Hodgkin lymphoma can be subclassified into four pathologic subtypes (nodular sclerosing, mixed cellularity, lymphocyte rich and lymphocyte depleted) based upon Reed-Sternberg cell morphology and the composition of the reactive cell infiltrate seen in the lymph node biopsy specimen (the cell composition around the Reed-Sternberg cell(s)). Nodular lymphocyte-predominant Hodgkin lymphoma expresses CD20, while classical Hodgkin's lymphoma does not express CD20.

Human Immunodeficiency Virus (HIV): A lentivirus that causes HIV infection and over time acquired immunodeficiency syndrome (AIDS). AIDS is a condition in humans in which progressive failure of the immune system allows life-threatening opportunistic infections and cancers to thrive. Without treatment, average survival time after infection with HIV is estimated to be 9 to 11 years, depending on the HIV subtype Two types of HIV have been characterized: HIV-1 and HIV-2. HIV-1 is the virus that was initially discovered and termed both LAV and HTLV-III, and is the more virulent, more infective subtype. HIV is different in structure from other retroviruses. The viral particle is roughly spherical, and has a diameter of about 120 nm. It is composed of two copies of positive single-stranded RNA that codes for the virus's nine genes enclosed by a conical capsid composed of 2,000 copies of the viral protein p24. The single-stranded RNA is tightly bound to nucleocapsid proteins, p7, and enzymes needed for the development of the virion such as reverse transcriptase, protease, ribonuclease and integrase. A matrix composed of the viral protein p17 surrounds the capsid ensuring the integrity of the virion particle. HIV can infect a variety of immune cells such as CD4+ T cells, macrophages, and microglial cells.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Linker: A bi-functional molecule that can be used to link two molecules into one contiguous molecule, for example, to link an effector molecule to an antibody. In some embodiments, the provided conjugates include a linker between the effector molecule or detectable marker and an antibody. In some cases, a linker is a peptide within an antigen binding fragment (such as an Fv fragment) which serves to indirectly bond the $V_H$ and $V_L$.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Lymphoid Malignancy: Lymphoma and leukemia. Hematological malignancies may derive from either of the two major blood cell lineages: myeloid and lymphoid cell lines. The myeloid cell line includes granulocytes, erythrocytes, thrombocytes, macrophages and mast cells; the lymphoid cell line produces B, T, NK and plasma cells. Lymphoma, lymphocytic leukemia, and myeloma are from the lymphoid line.

Natural Killer (NK) cells: NK cells are innate lymphoid cells that are large granular lymphocytes (LGL) and are differentiated from the common lymphoid progenitor-generating B and T lymphocytes. NK cells are known to differentiate and mature in the bone marrow, lymph nodes, spleen, tonsils, and thymus. NK cells do not express T-cell antigen receptors (TCR) or pan T marker CD3 or surface immunoglobulins (Ig) B cell receptors, but they usually express the surface markers CD16 (FcγRIII) and CD56 in humans, NK1.1 or NK1.2 in C57BL/6 mice. NKp46 cell surface marker is expressed in humans, several strains of mice and in monkey species.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The nucleotides can be ribonucleotides, deoxyribonucleotides, or modified forms of either nucleotide. The term includes single- and double-stranded forms of DNA.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as on-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms can include one dosage or multiple dosages (for example, in a vial from which metered dosages of the agents can selectively be dispensed).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Polypeptide modifications: Polypeptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng and Doolittle, *J. Mol. Evol.* 35:351-360, 1987. The method used is similar to the method described by Higgins and Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm nih gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff and Henikoff, *Proc. Natl. Acad. Sci. USA* 89:10915, 1989). An oligonucleotide is a linear polynucleotide sequence of up to about 100 nucleotide bases in length.

Specifically bind: When referring to an antibody or antigen binding fragment, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as CCR4 and does not bind in a significant amount to other proteins or polysaccharides present in the sample or subject. Specific binding can be determined by methods known in the art. With reference to an antibody-antigen complex, specific binding of the antigen and antibody has a $K_D$ of less than about $10^{-7}$ Molar, such as less than about $10^{-8}$ Molar, $10^{-9}$, or even less than about $10^{-10}$ Molar.

$K_D$ refers to the dissociation constant for a given interaction, such as a polypeptide ligand interaction or an antibody antigen interaction. For example, for the bimolecular interaction of an antibody or antigen binding fragment and an antigen it is the concentration of the individual components of the bimolecular interaction divided by the concentration of the complex.

The antibodies disclosed herein specifically bind to a defined target (or multiple targets, in the case of a bispecific antibody). Thus, an antibody that specifically binds to an epitope on CR4 is an antibody that binds substantially to CCR4, including cells or tissue expressing CCR4 substrate to which the CCR4 is attached, or CCR4 in a biological specimen. It is, of course, recognized that a certain degree of non-specific interaction may occur between an antibody or conjugate including an antibody (such as an antibody that specifically binds CCR4 or conjugate including such antibody) and a non-target (such as a cell that does not express CCR4). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, 2$^{nd}$ ed., Cold Spring Harbor Publications, N.Y. (2013), for a description of immunoassay formats and conditions that can be used to determine specific immunoreactivity.

Subject: Living multi-cellular vertebrate organisms, a category that includes human and non-human mammals. In an example, a subject is a human. In a particular example, the subject is a pediatric subject, such as a human child age 2-5 years old. In an additional example, a subject is selected that has a lymphoid malignancy or is at risk of having a lymphoid malignancy. In a further example, a subject is selected that has a solid tumor or is at risk of having a solid tumor.

T cell: A type of lymphocyte that plays a central role in cell-mediated immunity. T cells can be distinguished from other lymphocytes, such as B cells and natural killer cells, by the presence of a T-cell receptor on the cell surface. They are called T cells because they mature in the thymus from thymocytes. Generally, mature T cells express CD3.

Therapeutically effective amount: The amount of an agent (such as a T cells and/or NK cells expressing a CAR) that alone, or together with one or more additional agents, induces the desired response, such as, for example treatment of a CCR4-positive cancer, in a subject. When administered to a subject, a dosage will generally be used that will achieve target tissue concentrations that has been shown to achieve a desired in vitro effect. Ideally, a therapeutically effective amount provides a therapeutic effect without causing a substantial cytotoxic effect in the subject.

In one example, a desired response is to decrease the size, volume, or number (such as metastases) of CCR4-positive cancer cells in a subject, and/or neoplastic lesions or number of leukemia cells in blood in a subject. For example, the agent can decrease the size, volume, or number of CCR4-positive cancer cells, and/or neoplastic lesions or number of leukemia cells in blood by a desired amount, for example by at least 5%, at least 10%, at least 15%, at least 20%, at least 25%, at least 30%, at least 50%, at least 75%, at least 90%, or at least 95% as compared to a response in the absence of the agent.

Several preparations disclosed herein are administered in therapeutically effective amounts. A therapeutically effective amount that is administered to a human or veterinary subject will vary depending upon a number of factors associated with that subject, for example the overall health of the subject. A therapeutically effective amount can be determined by varying the dosage and measuring the resulting therapeutic response, such as the regression of a CCR4-positive lymphoid malignancy. Therapeutically effective amounts also can be determined through various in vitro, in vivo or in situ immunoassays. The disclosed agents can be administered in a single dose, or in several doses, as needed to obtain the desired response. However, the therapeutically effective amount of can be dependent on the source applied, the subject being treated, the severity and type of the condition being treated, and the manner of administration.

A therapeutically effective amount encompasses a fractional dose that contributes in combination with previous or subsequent administrations to attaining a therapeutic response. For example, a therapeutically effective amount of an agent can be administered in a single dose, or in several doses, for example daily, during a course of treatment lasting several days or weeks. However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Transduced and Transformed: A transformed cell is a cell into which a nucleic acid molecule has been introduced by molecular biology techniques. As used herein, the terms transduction and transformation encompass all techniques by which a nucleic acid molecule might be introduced into such a cell, including transfection with viral vectors, the use of plasmid vectors, and introduction of DNA by electroporation, lipofection, and particle gun acceleration.

Treating or Preventing a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as a malignancy.

Tumor: An abnormal growth of cells, which can be benign or malignant (a malignancy). Cancer is a malignant tumor (a malignancy), which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In specific non-limiting examples, the lymphoid malignancy can be adult T cell leukemia, cutaneous T cell lymphoma, anaplastic large cell lymphoma, Hodgkin's lymphoma, or a diffuse large B cell lymphoma.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is breast, ovarian, gastric or esophageal cancer.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function. For example, such that the viral vector does not replicate in typical host cells, especially those in a human patient that could be infected by the viral vector in the course of a therapeutic method.

Chimeric Antigen Receptors

Chimeric antigen receptor (CARs) are disclosed that are artificially constructed chimeric proteins including an extracellular antigen binding domain (e.g., single chain variable fragment (scFv)) that specifically binds to CCR4, linked to a transmembrane domain, and linked to one or more intracellular T cell signaling domains. Characteristics of the disclosed CARs include their ability to redirect T cell specificity and reactivity towards CCR4 expressing cells, such as cells that express CCR4 mRNA, in a non-MHC-restricted manner The non-MHC-restricted CCR4 recognition gives T cells (or NK cells) expressing a disclosed CAR the ability to recognize antigen independent of antigen processing.

The intracellular T cell signaling domains can include, for example, a T cell receptor signaling domain, a T cell costimulatory signaling domain, or both. The T cell receptor signaling domain refers to a portion of the CAR comprising the intracellular domain of a T cell receptor, such as the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen, such as 4-1BB. The CAR are disclosed in further detail below.

In some embodiments, the CAR includes: (a) an extracellular scFv comprising a light chain variable domain ($V_L$) and a heavy chain variable domain ($V_H$) and of the mAB2-3 antibody, wherein the scFv specifically binds to CCR4; (b) a hinge and transmembrane domain from CD8; (c) an intracellular 4-1BB signaling domain; and (d) an intracellular CD3 zeta signaling domain, wherein (a)-(d) are in N terminal to C terminal order. In some embodiments, a signal sequence, such as but not limited to the mouse immunoglobulin signal sequence, is included N-terminal to the scFv.

A. Extracellular Region

The disclosed CARs include an antigen binding domain of a monoclonal antibody that specifically binds bind CCR4. In some embodiments, mAb1567, which specifically binds CCR4, and can be used in the chimeric antigen binding receptors disclosed herein. The affinity matured humanized form on this antibody, called mAb2-3 (see Chang et al., Mol Cancer Ther. 2012; 11(11):2451-2461, incorporated herein by reference) can also be included in the CAR. Other monoclonal antibodies that specifically bind CCR4 are commercially available and are known in the art, see for example, Hagemann et al., PLOS One, 2014, available on-line at the PLOS one website (journals.plos.org_plosone_article?id=10.1371/journal.pone.0103776). Any antibody, or antigen binding fragment thereof, that specifically binds CCR4, can be included in the chimeric antigen receptor.

In some embodiments, the antigen binding domain can include a $V_H$ and a $V_L$ including the HCDR1, HCDR2, HCDR3, LCDR1, LCDR2, and LCDR3 of the $V_H$ and $V_L$, respectively, of the mAb1567 or the mAb2-3 antibody (affinity matured form of the mAb1567). Locations of the HCDRs and LCDRs for these antibodies are provided in FIG. 3 of Chang et al. The amino acid sequence of the $V_H$ of a humanized mAb1567 is:

```
                                      (SEQ ID NO: 1)
QVQLVQSGAE VKKPGASVKV SCKASGYTFA SAWMHWMRQA

PGQGLEWIGW INPGNVNTKY NEKFKGRATL TVDTSTNTAY

MELSSLRSED TAVYYCARST YYRPLDYWGQ GTLVTVSS,
``` wherein the CDR sequences are in bold and underlined.

Thus, in some embodiments, the antigen binding fragment of the monoclonal antibody includes an HCDR1, HCDR2, and HCDR3, wherein the HCDR1 includes amino acids 26-33 of SEQ ID NO: 1, the HCDR2 includes amino acids 51-58 of SEQ ID NO: 1, and the HCDR3 includes amino acids 99-107 of SEQ ID NO: 1.

The amino acid sequence of the $V_L$ of a humanized mAb1567 is:

```
                                      (SEQ ID NO: 2)
DIVMTQSPDSLAVSLGERATINCKSSQSILYSSNQKNYLAWYQQKPGQSP

KLLIYWASTRESGVPDRFSG SGSGTDFTLT ISSLQAEDVA VYYCHQY

MSS YTFGQGTKLE IK,
``` where the LCDR sequences are in bold and underlined.

In some embodiments, the antigen binding domain of the monoclonal antibody includes an LCDR1, LCDR2, and LCDR3, wherein the LCDR1 includes amino acids 27-38 of SEQ ID NO: 2, the LCDR2 includes amino acids 56-61 of SEQ ID NO: 2, and the LCDR3 includes amino acids 95-102 of SEQ ID NO: 2.

In further embodiments, the heavy chain domain of the antigen binding domain includes an HCDR1, HCDR2 and HCDR2, wherein the HCDR1 includes amino acids 26-33 of SEQ ID NO: 1, the HCDR2 includes amino acids 51-58 of SEQ ID NO: 1, and the HCDR3 includes amino acids 99-107 of SEQ ID NO: 1, and the light chain domain of the antigen binding domain of the monoclonal antibody includes an LCDR1, LCDR2, and LCDR3, wherein the LCDR1 includes amino acids 27-38 of SEQ ID NO: 2, the LCDR2 includes amino acids 56-61 of SEQ ID NO: 2, and the LCDR3 includes amino acids 95-102 of SEQ ID NO: 2. In a specific non-limiting example, the antigen binding domain includes the antigen binding domain includes a $V_H$ and a $V_L$ including the amino acid sequences set forth as SEQ ID NOs: 1 and 2.

In several embodiments, the antigen binding domain can be a scFv. To create a scFv the $V_L$- and $V_H$-encoding DNA fragments can be operatively linked to another fragment encoding a flexible linker, e.g., encoding the amino acid sequence $(Gly_4\text{-}Ser)_3$, such that the $V_L$ and $V_H$ sequences can be expressed as a contiguous single-chain protein, with the $V_L$ and $V_H$ domains joined by the flexible linker (see, e.g., Bird et al., *Science* 242:423-426, 1988; Huston et al., *Proc. Natl. Acad. Sci. USA* 85:5879-5883, 1988; McCafferty et al., *Nature* 348:552-554, 1990; Kontermann and Dubel (Ed), Antibody Engineering, Vols. 1-2, $2^{nd}$ Ed., Springer Press, 2010; Harlow and Lane, *Antibodies: A Laboratory Manual*, $2^{nd}$, Cold Spring Harbor Laboratory, N.Y., 2013,). Optionally, a cleavage site can be included in a linker, such as a furin cleavage site. In some embodiments, the scFv includes a $V_H$ and a $V_L$ joined by a peptide linker, such as a linker including the amino acid sequence set forth as SSGGGGSGGGGSGGGGS (SEQ ID NO: 3). The $V_L$ and $V_H$ can ben in any order, such that either the $V_L$ or the $V_H$ is at the N-terminus of the scFv. In one specific non-limiting example, the $V_L$ is at the N-terminus.

The CAR can include a signal peptide sequence, e.g., N-terminal to the antigen binding domain. The signal peptide sequence can include any suitable signal peptide sequence. In an embodiment, the signal peptide sequence is the Mouse immunoglobulin light chain kappa signal sequence, such as an amino acid sequence including of consisting of MDFQVQIFSFLLISASVIMSRG (SEQ ID NO: 4). However, other signal sequences known in the art can be utilized. In another example, the signal peptide sequence is a human granulocyte-macrophage colony-stimulating factor (GM-CSF) receptor sequence, such as an amino acid sequence including or consisting of LLVTSLLL-CELPHPAFLLIPDT (SEQ ID NO: 5). In a further example, the signal peptide sequence is an IL-2 signal peptide. While the signal peptide sequence may facilitate expression of the CAR on the surface of the cell, the presence of the signal peptide sequence in an expressed CAR is not necessary in order for the CAR to function. Upon expression of the CAR on the cell surface, the signal peptide sequence may be cleaved off of the CAR. Accordingly, in some embodiments, the CAR lacks a signal peptide sequence.

Between the antigen binding domain and the transmembrane domain of the CAR, there can be a spacer domain, which includes a polypeptide sequence. The spacer domain may comprise up to 300 amino acids, such as 10 to 100 amino acids, for example 25 to 50 amino acids. In some embodiments, the spacer domain can include an immunoglobulin domain, such as a human immunoglobulin sequence. In an embodiment, the immunoglobulin domain comprises an immunoglobulin CH2 and CH3 immunoglobulin G ($IgG_1$) domain sequence (CH2CH3). In this regard, the spacer domain can include an immunoglobulin domain comprising or consisting of the amino acid sequence set forth as SEQ ID NO: 6:

```
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKDPK
```

Without being bound to a particular theory, it is believed that the CH2CH3 domain extends the antigen binding domain of the CAR away from the membrane of CAR-expressing cells and may more accurately mimic the size and domain structure of a native TCR. However, the CH2CH3 domain may not be necessary. In some embodiments, the spacer is omitted, so that it is not present.

B. Transmembrane Domain

With respect to the transmembrane domain, the CAR can be designed to include a transmembrane domain that is fused to the extracellular domain of the CAR. The transmembrane domain can be derived either from a natural or from a synthetic source. Where the source is natural, the domain can be from any membrane-bound or transmembrane protein. Exemplary transmembrane domains for use in the disclosed CARs can include at least the transmembrane region(s) of) the alpha, beta or zeta chain of the T cell receptor, CD28, CD3 epsilon, CD45, CD4, CD5, CD8, CD9, CD 16, CD22, CD33, CD37, CD64, CD80, CD86, CD 134, CD137, CD154. Alternatively the transmembrane domain can be synthetic, in which case it will comprise predominantly hydrophobic residues such as leucine and valine. In several embodiments, a triplet of phenylalanine, tryptophan and valine will be found at each end of a synthetic transmembrane domain.

Optionally, a short oligo- or polypeptide linker, preferably between 2 and 10 amino acids in length may form the linkage between the transmembrane domain and the intracellular T cell signaling domain and/or T cell costimulatory domain of the CAR. An exemplary linker sequence includes one or more glycine-serine doublets. For example, the linker can include, or consist of:

```
                                           (SEQ ID NO: 3)
SSGGGGSGGGGSGGGGS.
```

In some embodiments, the transmembrane domain comprises the transmembrane domain of a T cell receptor, such as a CD8 transmembrane domain. Thus, the CAR can include a CD8 transmembrane domain including or consisting of

```
                                           (SEQ ID NO: 7)
ALSNSIMYFSHFVPVFLPAKPTTTPAPRPPTPAPTIASQP LSLRPEACR

PAAGGAVHTRGLDFAC DIYIWAPLAGTCGVLLLSLVITLYCNHR.
```

In other embodiments, the transmembrane domain comprises the transmembrane domain of a T cell costimulatory molecule, such as CD137 or CD28. An exemplary CD28 transmembrane domain includes or consists of SEQ ID NO: 19:

```
IEVMYPPPYLDNEKSNGTIIHVKGKHLCPSPLFPGPSKPFWVLVVVGGVL

ACYSLLVTVAFIIFWVR.
```

C. Intracellular Region

The intracellular region of the CAR includes one or more intracellular T cell signaling domains responsible for activation of at least one of the normal effector functions of a T cell in which the CAR is expressed or placed in. Exemplary T cell signaling domains are provided herein, and are known to the person of ordinary skill in the art.

While an entire intracellular T cell signaling domain can be employed in a CAR, in many cases it is not necessary to use the entire chain. To the extent that a truncated portion of the intracellular T cell signaling domain is used, such truncated portion may be used in place of the intact chain as long as it transduces the relevant T cell effector function signal. Examples of intracellular T cell signaling domains for use in the CAR include the cytoplasmic sequences of the T cell receptor (TCR) and co-stimulatory molecules that act in concert to initiate signal transduction following antigen receptor engagement, as well as any derivative or variant of these sequences and any synthetic sequence that has the same functional capability.

Examples of intracellular T cell signaling domains for use in the CAR include the cytoplasmic sequences of the T cell receptor (TCR) and co-stimulatory molecules that act in concert to initiate signal transduction following antigen receptor engagement, as well as any derivative or variant of these sequences and any synthetic sequence that has the same functional capability.

T cell receptor signaling domains regulate primary activation of the T cell receptor complex either in a stimulatory way, or in an inhibitory way. The disclosed CARs can include primary cytoplasmic signaling sequences that act in a stimulatory manner, which may contain signaling motifs that are known as immunoreceptor tyrosine-based activation motifs or ITAMs. Examples of ITAM containing primary cytoplasmic signaling sequences that can be included in a disclosed CAR include those from CD3 zeta, FcR gamma, FcR beta, CD3 gamma, CD3 delta, CD3 epsilon, CDS, CD22, CD79a, CD79b, and CD66d proteins. In several embodiments, the cytoplasmic signaling molecule in the CAR includes an intracellular T cell signaling domain from CD3 zeta.

The intracellular region of the CAR can include the ITAM containing primary cytoplasmic signaling domain (such as CD3-zeta) by itself or combined with any other desired cytoplasmic domain(s) useful in the context of a CAR. For example, the cytoplasmic domain of the CAR can include a CD3 zeta chain portion and an intracellular costimulatory signaling domain, such as, but not limited to, a 4-1BB (CD137) domain. The costimulatory signaling domain refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40 (CD134), CD30, CD40, PD-1, ICOS, lymphocyte function-associated antigen 1 (LFA-1), CD2, CD7, LIGHT, NKG2C, and B7-H3.

Exemplary amino acid sequences for such T cell signaling domains are provided. For example, a 4-1BB signaling domain includes of consists of the amino acid sequence set forth as:

```
                                           (SEQ ID NO: 8)
KRGRKKLLYIFKQPFMRPVQTTQEEDG CSCRFPEEEEGGCEL.
```

In addition, a CD3 zeta signaling domain can include or consist of the amino acid sequence set forth as:

```
                                           (SEQ ID NO: 9)
RVKFSRSADAPAYQQGQNQLYNELN LGRREEYDVLDKRRGRDPEM

GGKPRRKNPQEGLYNELQKD KMAEAYSEIGMKGERRRGKG

HDGLYQGLSTATKDTYDALH MQALPPR.
```

The cytoplasmic signaling sequences within the cytoplasmic signaling portion of the CAR can be linked to each other in a random or specified order. In one non-limiting example, the 4-1BB domain is included at the amino terminus of the CD3 zeta domain. Optionally, a short polypeptide linker, preferably between 2 and 10 amino acids in length can form the linkage between these two domains. A glycine-serine doublet provides a particularly suitable linker. Further, between the signaling domain and the transmembrane domain of the CAR, there may be a spacer domain, which includes a polypeptide sequence. The spacer domain may include up to 300 amino acids, such as 10 to 100 amino acids, for example, 25 to 50 amino acids.

D. Additional Description of CARs

In some embodiments, the order of the domains is N-terminus, signal sequence, VL-linker VH (or VH-linker-VL), hinge, transmembrane domain, human 4-1BB signaling molecule, human CD3 zeta signaling molecule, C-terminus. An exemplary CAR of the present disclosure includes, or consists of, the amino acid sequence set forth as to a similar extent, the same extent, or to a higher extent, as the parent CAR. In reference to the parent CAR, the functional variant can, for instance, be at least about 30%, about 50%, about 75%, about 80%, about 85%, about 90%, about 91%, about 92%, about 93%, about 94%, about 95%, about 96%), about 97%, about 98%, about 99% or more identical in amino acid sequence to the parent CAR.

(SEQ ID NO: 10)
MDFQVQIFSFLLISASVIMSRG<u>DIVMTQSPDSLAVSLGERATINCKSSQSILYSSNQKNYLA</u>

<u>WYQQKPGQSPKLLIYWASTR ESGVPDRFSG SGSGTDFTLTISSLQAEDVA</u>

<u>VYYCHQYMSS YTFGQGTKLE IK</u> *SSGGGGSGGGGSGGGGS* QVQLVQSGAE

VKKPGASVKV SCKASGYTFA SAWMHWMRQA PGQGLEWIGW INPGNVNTKY

NEKFKGRATL TVDTSTNTAY MELSSLRSED TAVYYCARST YYRPLDYWGQ

GTLVTVSS ALSNSIMYFSHFVPVFLPAKPTTTPAPRPPTPAPTIASQP

LSLRPEACRPAAGGAVHTRG LDFAC DIYIWAPLAGTCGVLLLSLVITLYCNHR

*<u>KRGRKKLLYIFKQPFMRPVQTTQEEDG</u>* CSCRFPEEEEGGCEL

RVKFSRSADAPAYQQGQNQLYNELN LGRREEYDVLDKRRGRDPEM

GGKPRRKNPQEGLYNELQKD DMAEAYSEIGMKGERRRGKG

HDGLYQGLSTATKDTYDALH MQALPPR.

In SEQ ID NO: 10, the signal sequence is presented bold, the $V_L$ is shown underlined, the linker is shown in italics, the $V_H$ is shown with a combination of bold/underlined, the human CD8 hinge and transmembrane domain is highlighted, the human 4-1BB signaling molecule is shown in a combination of italics and underlined) and the human CD3 zeta signaling molecule is shown in purple (and plan text).

Also provided are functional portions of any of the CARs described herein. The term "functional portion" when used in reference to a CAR refers to any part or fragment of the CAR, which part or fragment retains the biological activity of the CAR of which it is a part (the parent CAR), and thus can be used to target T cells and/or natural killer cells to CCR4. Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 60%, 70%, 80%, 90%, 95%, or more, of the parent CAR.

The CAR or functional portion thereof, can include additional amino acids at the amino or carboxy terminus, or at both termini, which additional amino acids are not found in the amino acid sequence of the parent CAR. In some examples, the additional amino acids do not interfere with the biological function of the CAR or functional portion, e.g., recognize target cells, detect cancer, treat or prevent cancer, etc. In other examples, the additional amino acids enhance the biological activity, as compared to the biological activity of the parent CAR.

Also provided are functional variants of the CARs described herein, which have substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, the non-conservative amino acid substitution does not interfere with or inhibit the biological activity of the functional variant. The non-conservative amino acid substitution may enhance the biological activity of the functional variant, such that the biological activity of the functional variant is increased as compared to the parent CAR. The CAR can also include up to ten conservative amino acid substitutions, such as 1, 2, 3, 4, 5, 6, 7, 8, 9, or 10 conservative substitutions, provided the activity of the molecule is not changed. Substitutions can be made, for example, in the linker region, spacers, and/or the signal sequence.

The CARs (including functional portions and functional variants of the invention) can include synthetic amino acids in place of one or more naturally-occurring amino acids. Such synthetic amino acids are known in the art, and include, for example, aminocyclohexane carboxylic acid, norleucine, a-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, oc-aminocycloheptane carboxylic acid, −(2-amino-2-norbornane)-carboxylic acid, γ-diaminobutyric acid, α,β-diaminopropionic acid, homophenylalanine, and α-tert-butylglycine. The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

Methods of generating chimeric antigen receptors, immune cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.*, 29:550-557, 2011; Grupp et al., N Engl J Med., 368:1509-1518, 2013; Han et al., J. Hematol Oncol., 6:47, 2013; PCT Publication Nos. WO2012/079000, WO2013/126726; and U.S. Publication No. 2012/0213783, each of which is incorporated by reference herein in its entirety). For example, a nucleic acid molecule encoding a disclosed chimeric antigen binding receptor can be included in an expression vector (such as a lentiviral vector) for expression in a host cell, such as a T cell, to make the disclosed CAR. In some embodiments, methods of using the chimeric antigen receptor include isolating T cells from a subject, transforming the T cells with an expression vector (such as a lentiviral vector or a gamma retroviral vector) encoding the chimeric antigen receptor, and administering the engineered T cells expressing the chimeric antigen receptor to the subject for treatment, for example for treatment of a CCR4-positive cancer in the subject.

Polynucleotides and Expression

Nucleic acid molecules (for example, cDNA molecules) encoding the amino acid sequences of CARs that specifically bind CCR4 are provided herein. Nucleic acids encoding these molecules can readily be produced by one of skill in the art, using the amino acid sequences provided herein (such as the CDR sequences and $V_H$ and $V_L$ sequences), sequences available in the art (such as framework or constant region sequences), and the genetic code. In several embodiments, a nucleic acid molecule can encode a CAR including the $V_H$, the $V_L$, or both the $V_H$ and $V_L$ of a monoclonal antibody that specifically binds CCR4, such as, but not limited to, the mAb2-3 monoclonal antibody, the mAb1567 monoclonal antibody or an antigen binding fragment thereof. In several embodiments, the nucleic acid molecules can be expressed in a host cell (such as a mammalian cell, for example a T cell) to produce the CAR.

In some embodiments, the complete nucleic acid sequence encoding the CAR is codon optimized for expression in human cells, such as human T cells or natural killer (NK) cells. In additional embodiments, a nucleic acid sequence encoding one or more components of the CAR ($V_H$, $V_L$, signal sequence, human CD8 hinge and transmembrane domain, human 4-1BB signaling molecule, human CD3 zeta signaling molecule) can be codon optimized for expression in human cells, but all of the nucleic acid sequences encoding the components of the CAR are codon optimized for expression in human cells. Thus, in some embodiments, the nucleic acid sequence includes one or more codon optimized nucleic acid sequences.

In some embodiments, the nucleic acid sequence encoding the signal sequence, for example the mouse immunoglobulin light chain kappa signal sequence, is codon optimized for expression in human cells. Thus, the nucleic acid molecule encoding the signal sequence can include, or consist of:

(SEQ ID NO: 11)
ATGGACTTTCAAGTGCAGATCTTTAGTTTCCTGCTCATAAGCGCTAGTGT

GATCATGTCCAGAGGA.

In other embodiments, the nucleic acid molecule encoding the signal sequence in the CAR includes a nucleic acid encoding a signal sequence at least 80%, 85%, 90%, 95%, 96%, 97%, 98%, or 99% identical to SEQ ID NO: 11, wherein the sequence functions as a signal sequence in human cells, such as human T cells and/or NK cells.

In further embodiments, the nucleic acid sequence encoding the $V_L$ is codon optimized for expression in human cells. Thus, the nucleic acid encoding the $V_L$ of the CAR can include, or consist of:

(SEQ ID NO: 12)
GATATTGTGATGACTCAAAGCCCCGACAGTCTGGCCGTGTCTTTGGGCGA

GAGAGCCACAATCAACTGCAAGTCCTCACAGAGTATCCTTTATTCCTCTA

ATCAGAAGAATTACCTCGCATGGTATCAACAAAAACCCGGACAGAGCCCT

AAGCTTTTGATCTATTGGGCATCTACCCGAGAATCAGGAGTGCCGGACCG

CTTCAGTGGATCAGGATCAGGCACAGACTTTACGCTGACAATATCCTCTC

TTCAGGCCGAAGACGTTGCCGTGTACTACTGCCATCAATATATGTCAAGC

TACACATTCGGCCAGGGCACCAAACTCGAGATTAAG.

In other embodiments, the nucleic acid molecule encoding the CAR includes a nucleic acid sequence encoding a $V_L$ at least 90%, 95%, 96%, 97%, 98%, or 99% identical to SEQ ID NO: 12, wherein the encoded antigen binding domain specifically binds CCR4. In specific non-limiting examples, the nucleic acid encodes a $V_L$ wherein the LCDR1 includes amino acids 27-38 of SEQ ID NO: 2, the LCDR2 includes amino acids 56-61 of SEQ ID NO: 2, and the LCDR3 includes amino acids 95-102 of SEQ ID NO: 2.

In yet other embodiments, the nucleic acid sequence encoding the $V_H$ is codon optimized for expression in human cells. Thus, the nucleic acid encoding the $V_H$ of the CAR can include, or consist of:

(SEQ ID NO: 13)
CAGGTTCAGCTCGTGCAATCAGGGGCAGAGGTCAAGAAGCCGGGTGCCTC

TGTGAAGGTGTCATGTAAGGCCTCCGGGTATACTTTTGCCAGCGCCTGGA

TGCATTGGATGAGGCAGGCGCCCGGCCAGGGTCTGGAGTGGATTGGTTGG

ATTAATCCCGGAAACGTGAATACTAAGTATAACGAGAAGTTTAAGGGCAG

GGCCACACTCACAGTCGACACAAGCACCAATACCGCGTACATGGAACTTT

CCAGCCTCCGGTCCGAGGACACTGCGGTGTATTACTGCGCACGCTCCACC

TATTACAGACCACTTGATTACTGGGGCCAAGGGACCCTGGTGACCGTGTC

TAGC.

In other embodiments, the nucleic acid molecule encoding the CAR includes a nucleic acid sequence encoding a $V_H$ at least 90%, 95%, 96%, 97%, 98%, or 99% identical to SEQ ID NO: 13, wherein the encoded antigen binding domain specifically binds CCR4. In specific non-limiting examples, nucleic acid sequence encodes a $V_H$ wherein the HCDR1 includes amino acids 26-33 of SEQ ID NO: 1, the HCDR2 includes amino acids 51-58 of SEQ ID NO: 1, and the HCDR3 includes amino acids 99-107 of SEQ ID NO: 1.

In additional embodiments, the nucleic acid sequence encoding a linker sequence (located between the nucleic acid sequences encoding the V$_H$ and the V$_L$) can be codon optimized for expression in human cells. Thus, the nucleic acid encoding the linker in the CAR can include, or consist of:

(SEQ ID NO: 14)
TCTAGTGGTGGCGGAGGCAGTGGCGGAGGAGGCTCCGGGGGCGGAGGGTC
C.

In other embodiments, the nucleic acid molecule encoding the CAR includes a nucleic acid sequence encoding a V$_H$ at least 90%, 95%, 96%, 97%, 98%, or 99% identical to SEQ ID NO: 14.

In more embodiments, the nucleic acid sequence encoding the human CD8 hinge and transmembrane domain can be codon optimized for expression in human cells. Thus, the nucleic acid encoding the CD8 hinge and transmembrane domain in the CAR can include, or consist of:

(SEQ ID NO: 15)
GCACTCAGCAATTCCATCATGTACTTCTCTCATTTCGTGCCAGTATTTCT

GCCTGCCAAGCCAACTACCACACCTGCGCCACGCCCTCCCACGCCCGCAC

CCACAATTGCTTCACAGCCTCTTTCTCTGCGGCCTGAGGCTTGTCGCCCA

GCAGCCGGAGGCGCCGTGCATACGCGCGGCCTTGACTTCGCATGTGACAT

CTACATTTGGGCTCCTTTGGCTGGAACCTGCGGGTGTTGTTGCTTAGTC

TGGTGATTACCCTCTACTGCAATCATAGA.

In other embodiments, the nucleic acid molecule encoding the CAR includes a nucleic acid sequence encoding a CD8 hinge and transmembrane domain is at least 80%, 85%, 90%, 95%, 96%, 97%, 98%, or 99% identical to SEQ ID NO: 15, wherein the encoded protein functions as a transmembrane domain.

In some embodiments, the nucleic acid sequence encoding the human 4-1BB signaling molecule can be codon optimized for expression in human cells. Thus, the nucleic acid encoding the 4-1BB signaling molecule in the CAR can include, or consist of:

(SEQ ID NO: 16)
AAGCGGGGCGAAAGAAACTTCTCTATATCTTCAAACAGCCTTTCATGCG

ACCAGTGCAGACAACCCAAGAGGAAGACGGATGCAGCTGTCGCTTTCCAG

AGGAGGAAGAAGGGGCTGCGAGCTG.

In other embodiments, the nucleic acid molecule encoding the CAR includes a nucleic acid sequence encoding a 4-1BB signaling molecule is at least 85%, 90%, 95%, 96%, 97%, 98%, or 99% identical to SEQ ID NO: 16, wherein the encoding protein functions as a signaling molecule.

In additional embodiments, the nucleic acid sequence encoding the CD3 zeta domain can be codon optimized for expression in human cells. Thus, the nucleic acid encoding the CD3 zeta domain in the CAR can include, or consist of:

(SEQ ID NO: 17)
AGAGTGAAATTCTCTCGCTCCGCTGACGCCCCCGCGTATCAACAGGGCCA

GAATCAGCTCTACAACGAACTTAACCTTGGGCGGAGAGAAGAATACGATG

TTCTCGACAAGCGCAGGGGGAGAGACCCTGAGATGGGCGGGAAACCGCGC

CGCAAGAACCCCCAAGAAGGGTTGTATAACGAGCTCCAGAAGGACAAAAT

GGCTGAAGCCTACTCAGAGATAGGTATGAAGGGCGAGCGCCGCAGAGGGA

AGGGACACGATGGTCTGTACCAAGGCCTTTCAACCGCCACCAAGGATACC

TATGAT.

In other embodiments, the nucleic acid molecule encoding the CAR includes a nucleic acid sequence encoding a CD3 zeta signaling molecule is at least 80%, 85%, 90%, 95%, 96%, 97%, 98%, or 99% identical to SEQ ID NO: 17, wherein the encoded protein functions as a CD3 zeta signaling molecule.

In one specific non-limiting example, the entire nucleic acid sequence encoding the CAR is codon optimized for expression in human cells, and comprises, or consists of:

(SEQ ID NO: 18)
GCGGCCGCATGGACTTTCAAGTGCAGATCTTTAGTTTCCTGCTCATAAGC

GCTAGTGTGATCATGTCCAGAGGAGATATTGTGATGACTCAAAGCCCCGA

CAGTCTGGCCGTGTCTTTGGGCGAGAGAGCCACAATCAACTGCAAGTCCT

CACAGAGTATCCTTTATTCCTCTAATCAGAAGAATTACCTCGCATGGTAT

CAACAAAAACCCGGACAGAGCCCTAAGCTTTTGATCTATTGGGCATCTAC

CCGAGAATCAGGAGTGCCGGACCGCTTCAGTGGATCAGGATCAGGCACAG

ACTTTACGCTGACAATATCCTCTCTTCAGGCCGAAGACGTTGCCGTGTAC

TACTGCCATCAATATATGTCAAGCTACACATTCGGCCAGGGCACCAAACT

CGAGATTAAGTCTAGTGGTGGCGGAGGCAGTGGCGGAGGAGGCTCCGGGG

GCGGAGGGTCCCAGGTTCAGCTCGTGCAATCAGGGGCAGAGGTCAAGAAG

CCGGGTGCCTCTGTGAAGGTGTCATGTAAGGCCTCCGGGTATACTTTTGC

CAGCGCCTGGATGCATTGGATGAGGCAGGCGCCCGGCCAGGGTCTGGAGT

GGATTGGTTGGATTAATCCCGGAAACGTGAATACTAAGTATAACGAGAAG

TTTAAGGGCAGGGCCACACTCACAGTCGACACAAGCACCAATACCGCGTA

CATGGAACTTTCCAGCCTCCGGTCCGAGGACACTGCGGTGTATTACTGCG

CACGCTCCACCTATTACAGACCACTTGATTACTGGGGCCAAGGGACCCTG

GTGACCGTGTCTAGCGCACTCAGCAATTCCATCATGTACTTCTCTCATTT

CGTGCCAGTATTTCTGCCTGCCAAGCCAACTACCACACCTGCGCCACGCC

CTCCCACGCCCGCACCCACAATTGCTTCACAGCCTCTTTCTCTGCGGCCT

GAGGCTTGTCGCCCAGCAGCCGGAGGCGCCGTGCATACGCGCGGCCTTGA

CTTCGCATGTGACATCTACATTTGGGCTCCTTTGGCTGGAACCTGCGGGG

TGTTGTTGCTTAGTCTGGTGATTACCCTCTACTGCAATCATAGAAAGCGG

GGGCGAAAGAAACTTCTCTATATCTTCAAACAGCCTTTCATGCGACCAGT

GCAGACAACCCAAGAGGAAGACGGATGCAGCTGTCGCTTTCCAGAGGAGG

AAGAAGGGGCTGCGAGCTGAGAGTGAAATTCTCTCGCTCCGCTGACGCC

CCCGCGTATCAACAGGGCCAGAATCAGCTCTACAACGAACTTAACCTTGG

GCGGAGAGAAGAATACGATGTTCTCGACAAGCGCAGGGGGAGAGACCCTG

AGATGGGCGGGAAACCGCGCCGCAAGAACCCCCAAGAAGGGTTGTATAAC

```
-continued
GAGCTCCAGAAGGACAAAATGGCTGAAGCCTACTCAGAGATAGGTATGAA

GGGCGAGCGCCGCAGAGGGAAGGGACACGATGGTCTGTACCAAGGCCTTT

CAACCGCCACCAAGGATACCTATGATGCACTGCACATGCAAGCCCTGCCT

CCTCGCTAAGGATCC.
```

Nucleic acid sequences encoding the antibodies, antibody binding fragments, CARs and conjugates that specifically bind CCR4 can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques, and instructions sufficient to direct persons of skill through many cloning exercises are known (see, e.g, Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, N.Y., through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill. Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the CARs of the present disclosure can also be constructed in whole or in part using standard peptide synthesis well known in the art.

The nucleic acid molecule encoding the chimeric antigen binding receptor can operably linked to a promoter. The nucleic acid molecule encoding the CAR can be included in a vector (such as a lentiviral vector or gamma retroviral vector) for expression in a host cell. Exemplary cells are mammalian cells, and include a T cell, such as a cytotoxic T lymphocyte (CTL) or a regulatory T cell, and a NK cell. In specific non-limiting examples, the cell is a T cell, such as a CD3$^+$ T cell. The CD3$^+$ T cell can be a CD4$^+$ or a CD8$^+$ T cell. In other specific non-limiting examples, the cell is a NK cell. Methods of generating nucleic acid molecules encoding chimeric antigen receptors and T cells (or NK cells) including such receptors are known in the art (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.*, 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety).

If of interest, once expressed, a CAR can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin. Additional methods for expression and purification are known in the art, see, e.g., Harlow and Lane, *Antibodies: A Laboratory Manual*, 2$^{nd}$, Cold Spring Harbor Laboratory, N.Y., 2013, Simpson ed., Basic methods in Protein Purification and Analysis: A laboratory Manual, Cold Harbor Press, 2008, and Ward et al., *Nature* 341:544, 1989.

The nucleic acid molecules also can be expressed in a recombinantly engineered cell such as bacteria, plant, yeast, insect and mammalian cells. The CAR can be expressed as a fusion protein. Methods of expressing and purifying antibodies and antigen binding fragments are known and further described herein (see, e.g., Al-Rubeai (ed), *Antibody Expression and Production*, Springer Press, 2011). Those of skill in the art are knowledgeable in the numerous expression systems available for expression of proteins including *E. coli*, other bacterial hosts, yeast, and various higher eukaryotic cells such as the COS, CHO, HeLa and myeloma cell lines. The term "host cell" also includes any progeny of the subject host cell. It is understood that all progeny may not be identical to the parental cell since there may be mutations that occur during replication. Methods of stable transfer, meaning that the foreign DNA is continuously maintained in the host, are known in the art. As disclosed herein, specific embodiments of the present disclosure include T cells, such as human T cells and human NK cells, which express the CAR. These T cells can be CD3$^+$ T cells, such as CD4$^+$ or CD8$^+$ T cells. If of interest, once expressed, a CAR can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin. Additional methods for expression and purification are known in the art, see, e.g., Harlow and Lane, *Antibodies: A Laboratory Manual*, $2^{nd}$, Cold Spring Harbor Laboratory, N.Y., 2013, Simpson ed., Basic methods in Protein Purification and Analysis: A laboratory Manual, Cold Harbor Press, 2008, and Ward et al., *Nature* 341:544, 1989.

The expression of nucleic acids encoding the antibodies and antigen binding fragments described herein can be achieved by operably linking the DNA encoding the CAR to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this can include a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the CAR, and a second foreign DNA molecule encoding a selectable phenotype, such as the herpes simplex thymidine kinase gene. Another method is to use a eukaryotic viral vector, such as simian virus 40 (SV40), a lentivirus or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

In some embodiments, a viral vector is utilized for expression of the CAR. Viral vectors include, but are not limited to simian virus 40, adenoviruses, adeno-associated virus (AAV), lentiviral vectors, and retroviruses, such as gamma retroviruses. Retroviral vectors provide a highly efficient method for gene transfer into eukaryotic cells. Moreover, retroviral integration takes place in a controlled fashion and results in the stable integration of one or a few copies of the new genetic information per cell. Without being hound by theory, lentiviral vectors have the advantage over vectors derived from onco-retroviruses such as murine leukemia viruses in that they can transduce non-proliferating cells, such as hepatocytes. They also have the added advantage of low immunogenicity. The use of lentiviral vectors to express a CAR is known in the art, and is disclosed for example in U.S. Application No. 2014/0050708, which is incorporated herein by reference.

In some embodiments, host cells are produced for introduction into s subject of interest. The host cell can be a peripheral blood lymphocyte (PBL) or a peripheral blood mononuclear cell (PBMC), a purified T cell, or a purified NK cell. The T cell can be any T cell, such as a cultured T cell, e.g., a primary T cell, or a T cell from a cultured T cell line, e.g., Jurkat, SupTl, etc., or a T cell obtained from a mammal (such as a human patient to which the CAR-T cell will later be administered). If obtained from a mammalian subject, such as a human subject, the T cell can be obtained from numerous sources, including but not limited to blood, bone marrow, lymph node, the thymus, or other tissues or fluids. T cells can also be enriched for or purified. The T cell can be any type of T cell and can be of any developmental stage, including but not limited to, $CD3^+$ cells, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naive T cells, and the like. The T cell may be a $CD3^+$ T cell, such as a $CD8^+$ T cell or a $CD4^+$ T cell. In alternative embodiments, the cell can be an NK cells, such as an NK cell obtained from the same subject to which the CAR-NK cell will later be administered.

Also provided is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any recombinant expression vector, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector encoding the CAR. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein. The T cells can be $CD3^+$ T cells, such as $CD8^+$ T cell or a $CD4^+$ T cells. In some embodiments, the T cells are transformed with Epstein Barr virus, see Savoldo et al., Blood 110: 2620-2630, 2007, incorporated herein by reference. In other embodiments, the cells are heterologous to a recipient (see below), and are deleted for a HLA class I and/or T cell receptor, so they do not provoke a graft versus host disease (GVHD) or host versus graft reaction. The cells can also be NK cells. The cells can be autologous to a recipient or allogeneic. These populations are of use in any of the methods disclosed herein.

Methods of Treatment and Pharmaceutical Compositions

Disclosed herein are methods for treating a tumor, wherein the cells of the tumor express CCR4, specifically they produce the mRNA that encodes CCR4 and/or CCR4 protein. In some embodiments, the tumor is a malignancy, such as a lymphoid malignancy. The lymphoid malignancy can be adult T cell leukemia, cutaneous T cell lymphoma, anaplastic large cell lymphoma, Hodgkin's lymphoma, or a diffuse large B cell lymphoma. The adult T cell leukemia can be chronic, acute, smoldering or lymphomatous type. The cutaneous T cell lymphoma can be mycosis fungoides, pagetoid reticulosis, Sézary syndrome, granulomatous slack skin, lymphomatoid papulosis, pityriasis lichenoides chronica, pityriasis lichenoides et varioliformis acuta, CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma, angiocentric lymphoma, or blastic NK-cell lymphoma. In specific non-limiting examples, the cutaneous T cell lymphoma is peripheral T-cell lymphoma (PTCL)/cutaneous T-cell lymphoma (CTCL), or mycosis fungoides (MF)/Sezary syndrome (SS). In other embodiments, the tumor is a solid tumor, wherein the cells of the tumor express CCR4, specifically they produce the mRNA that encodes CCR4 and/or CCR4 protein. Specific non-limiting examples of a solid tumor, such as a solid malignancy, are breast, ovarian, gastric or esophageal cancer. Without being bound by theory, Tregs in the microenvironment can be targeted using the CARs disclosed herein.

The method includes administering to the subject a therapeutically effective amount of the pharmaceutical composition including a vector, such as a lentiviral vector encoding the CAR, and/or administering a therapeutically effective amount of a pharmaceutical composition comprising cells, such as T cells and/or NK cells, that express the CAR.

Human Immunodeficiency Virus (HIV) infection, and the resulting Acquired Immunodeficiency Syndrome (AIDS), remain threats to global public health, despite extensive efforts to develop anti-HIV therapeutic agents. Virus that persists despite suppressive combination antiretroviral treatment (cART) remains an obstacle to definitive treatment of HIV infection. Infected T follicular helper cells (Tfh), sheltered in the immune privileged site of B cell follicles of secondary lymphoid tissues, represent an important source of such residual virus, at least in part because effector CD8+ T cells able to clear infected cells from other sites are unable to efficiently access B cell follicles. Methods are disclosed herein for treating a subject, such as a subject with an HIV infection. The methods include administering to the subject a therapeutically effective amount of T cells and/or NK cells that express a CAR.

In some embodiments, disclosed is a method of treating an HIV infection, by administering to the subject a therapeutically effective amount of the pharmaceutical composition including a vector, such as a lentiviral vector encoding the CAR, and/or administering a therapeutically effective amount of a pharmaceutical composition comprising cells, such as T cells and/or NK cells, that express the CAR. Subjects in need thereof may subsequently undergo standard treatment with chemotherapy or surgery (for cancer) or anti-viral agents (for an HIV infection). Methods are disclosed herein for increasing the immune response, such as enhancing the immune system in a subject to HIV. Administration of the T cells that express the CAR, as disclosed herein, will increase the ability of a subject to eliminate residual HIV, such as to in the B cell follicles, to reduce or eliminate residual virus.

Pharmaceutical compositions can include a CAR-expressing cell, e.g., a plurality of CAR-expressing cells, as described herein, in combination with one or more pharmaceutically or physiologically acceptable carriers, diluents or excipients. The CAR-expressing cells can be T cells, such as CD3+ T cells, such as CD4+ and/or CD8+ T cells, and/or NK cells. Such compositions may include buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

The cells can be autologous to the recipient. However, the cells can also be heterologous (allogeneic). In some embodiments, the cells are T cells, such as T cells transformed with Epstein Barr virus, see Savoldo et al., Blood 110: 2620-2630, 2007, incorporated herein by reference. In other embodiments, the cells are heterologous (allogeneic) to a recipient (see below), and are deleted for a HLA class I and/or T cell receptor, so they do not provoke a graft versus host disease (GVHD) or host versus graft reaction.

With regard to the cells, a variety of aqueous carriers can be used, for example, buffered saline and the like, for introducing the cells. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration in these formulations can vary widely, and will be selected primarily based on fluid volumes, viscosities, body weight and the like in accordance with the particular mode of administration selected and the subject's needs.

In one embodiment, the pharmaceutical composition is substantially free of, e.g., there are no detectable levels of a contaminant, such as endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus.

The precise amount of the composition to be administered can be determined by a physician with consideration of individual differences in age, weight, tumor size, extent of metastasis, and condition of the patient (subject). It can generally be stated that a pharmaceutical composition comprising the T cells (and/or NK cells) described herein may be administered at a dosage of $10^4$ to $10^9$ cells/kg body weight, such as $10^5$ to $10^6$ cells/kg body weight, including all integer values within those ranges. Exemplary doses are $10^6$ cells/kg to about 1×10⁸ cells/kg, such as from about 5×10⁶ cells/kg to about 7.5×10⁷ cells/kg, such as at about 2.5×10⁷ cells/kg, or at about 5.0×10⁷ cells/kg.

A composition can be administered once or multiple times, such as 2, 3,4, 5, 6, 7, 8, 9, or 10 times at these dosages. The composition can be administered by using infusion techniques that are commonly known in immunotherapy (see, e.g., Rosenberg et al., New Eng. J. of Med. 319:1676, 1988). The compositions can be administered daily, weekly, bimonthly or monthly. In some non-limiting examples, the composition is formulated for intravenous administration and is administered multiple times. The quantity and frequency of administration will be determined by such factors as the condition of the subject, and the type and severity of the subject's disease, although appropriate dosages may be determined by clinical trials.

In one embodiment, the CAR is introduced into cells, such T cells or NK cells, and the subject receives an initial administration of cells, and one or more subsequent administrations of the cells, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR cells are administered to the subject (e.g., human) per week, e.g., 2, 3, or 4 administrations of the CAR cells of the invention are administered per week. In one embodiment, the subject receives more than one administration of the CAR T cells per week (e.g., 2, 3 or 4 administrations per week) (also referred to as a cycle), followed by a week of no CAR cells administrations, and then one or more additional administration of the CAR cells (e.g., more than one administration of the CAR T cells per week) is administered to the subject. In another embodiment, the subject (e.g., human subject) receives more than one cycle of CAR cells, and the time between each cycle is less than 10, 9, 8, 7, 6, 5, 4, or 3 days. In one embodiment, the CAR cells are administered every other day for 3 administrations per week. In another embodiment, the CAR cells are administered for at least two, three, four, five, six, seven, eight or more weeks. The dosage of the above treatments to be administered to a patient will vary with the precise nature of the condition being treated and the recipient of the treatment. The scaling of dosages for human administration can be performed according to art-accepted practices.

In some embodiments, CAR-modified T cells are able to replicate in vivo resulting in long-term persistence that can lead to sustained tumor control. In various aspects, the T cells administered to the subject, or the progeny of these cells, persist in the subject for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, or for years after administration of the T cell to the subject. In other embodiments, the cells and their progeny are present for less than six months, five month, four months, three months two months, or one month, e.g., three weeks, two weeks, one week, after administration of the T cell to the subject.

The administration of the subject compositions may be carried out in any convenient manner, including by injection, ingestion, transfusion, implantation or transplantation. The disclosed compositions can be administered to a patient trans arterially, subcutaneously, intradermally, intratumorally, intranodally, intramedullary, intramuscularly, by intravenous (i.v.) injection, or intraperitoneally. In some embodiments, the compositions are administered to a patient by intradermal or subcutaneous injection. In other embodiments, the compositions of the present invention are administered by i.v. injection. The compositions can also be injected directly into a tumor or lymph node.

In some embodiments, subjects can undergo leukapheresis, wherein leukocytes are collected, enriched, or depleted ex vivo to select and/or isolate the cells of interest, e.g., T cells and or NK cells. These cell isolates may be expanded by methods known in the art and treated such that one or more CAR constructs can be introduced, thereby creating an autologous cell that express the CAR. In one aspect, CAR expressing cells are generated using lentiviral viral vectors.

In some embodiments, the T and/or NK cells are autologous. In other embodiments, the T cells and/or NK cells are allogeneic. The T calls and/or NK cells are then introduced into the subject, as disclosed above. In one embodiment, the cells transiently express the vector for 4, 5, 6, 7, 8, 9, 10, 11, 12, 13, 14, 15 days after transduction. In one non-limiting example, the vector is transduced into the T cell by electroporation.

In some embodiments, a subject is administered a therapeutically effective amount of T cells and/or NK cells expressing the disclosed CAR. In particular embodiments (see U.S. Published Application No. US20140271635 A1, incorporated herein by reference), prior to expansion and genetic modification, a source of T cells is obtained from a subject.

The term "subject" is intended to include living organisms in which an immune response can be elicited (e.g., mammals). Examples of subjects include humans, dogs, cats, mice, rats, pigs (and other veterinary subjects) and non-human primates. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In other embodiments, any number of T cell lines available in the art, may be used. In some non-limiting examples, T cells and/or NK cells can be obtained from a unit of blood collected from a subject using any number of techniques known to the skilled artisan, such as FICOLL™ separation, or the cells can be obtained by apheresis. The apheresis product typically contains lymphocytes, including T cells, monocytes, granulocytes, B cells, NK cells, other nucleated white blood cells, red blood cells, and platelets. In some specific non-limiting examples, the cells are autologous.

Cells collected by apheresis can be washed to remove the plasma fraction and to place the cells in an appropriate buffer or media for subsequent processing steps. In some non-limiting examples, the cells are washed with phosphate buffered saline (PBS). In an alternative examples, the wash solution lacks calcium and may lack magnesium or may lack many if not all divalent cations. Initial activation steps in the absence of calcium can lead to magnified activation. The washing step can be accomplished by methods known in the art, such as by using a semi-automated "flow-through" centrifuge (for example, the Cobe 2991 cell processor, the Baxter CYTOMATE®, or the HAEMONETICS CELL SAVER 5®) according to the manufacturer's instructions. After washing, the cells can be resuspended in a variety of biocompatible buffers, such as a saline solution with or without buffer. Alternatively, the undesirable components of the apheresis sample can be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, T cells can isolated by incubation with anti-CD3/anti-CD28 (e.g., 3×28)-conjugated beads, such as DYNABEADS® M-450 CD3/CD28 T, for a time period sufficient for positive selection of the desired T cells, see U.S. Published Application No. US20140271635 A1. In a non-limiting example the time period is about 30 minutes. In other non-limiting examples, the time period ranges from 30 minutes to 36 hours or longer and all integer values there between. In further non-limiting examples, the time period is at least 1, 2, 3, 4, 5, 6 hours, 10 to 24 hours, 24 hours or longer. Longer incubation times can be used to isolate T cells in any situation where there are few T cells as compared to other cell types, such in isolation from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. Multiple rounds of selection can also be used.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. A T cell population can be selected that expresses one or more cytokines. Methods for screening for cell expression are disclosed in PCT Publication No. WO 2013/126712.

For isolation of a desired population of cells by positive or negative selection, the concentration of cells and surface (e.g., particles such as beads) can be varied. Into ensure maximum contact of cells and heads. In some embodiments, a concentration of 1 billion cells/nil is used. In further embodiments, greater than 100 million cells/ml is used. In other embodiments, a concentration of cells of 10, 15, 20, 25, 30, 35, 40, 45, 50, 65, 70, 75, 80, 85, 90, 95, or 100 million cells/nil is used. Without being bound by theory, using high concentrations can result in increased cell yield, cell activation, and cell expansion. Lower concentrations of cells can also be used. Without being bound by theory, significantly diluting the mixture of T cells and surface (e.g., particles such as beads), interactions between the particles and cells is minimized. This selects for cells that express high amounts of desired antigens to be hound to the particles. For example, CD4+ T cells express higher levels of CD28 and are more efficiently captured than CD8+ T cells in dilute concentrations. In some embodiments, the concentration of cells used is $5\times10^6$/ml. In other embodiments, the concentration used can be from about $1\times10^5$/ml to $1\times10^6$/ml, and any integer value in between.

Cells can be incubated on a rotator for varying lengths of time at varying speeds at either 2-10° C. or at room temperature. T cells for stimulation can also be frozen after a washing step. Without being hound by theory, the freeze and subsequent thaw step provides a more uniform product by removing granulocytes and to some extent monocytes in the cell population. After the washing step that removes plasma and platelets, the cells can be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 3 L25% Dextrose 5%, 0.45% NaCl, 10% Dextran 40 and 5% Dextrose, 20% Human Serum Albumin, and 7.5% DMSO or other suitable cell freezing media containing for example, Hespan and Plasmalyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen, see U.S. Publication No. US-2014-0271635 A1.

Blood samples or apheresis product can be collected from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. In certain aspects, cryopreserved cells are thawed and washed as described herein and allowed to rest for one hour at room temperature prior to use. Blood samples or apheresis product can be collected from a subject when needed, and not frozen.

T cells can be activated and expanded generally using methods as described, for example, in U.S. Pat. Nos. 6,352, 694; 6,534,055; 6,905,680; 6,692,964; 5,858,358; 6,887, 466; 6,905,681; 7,144,575; 7,067,318; 7,172,869; 7,232, 566; 7,175,843; 5,883,223; 6,905,874; 6,797,514; 6,867, 041; and U.S. Patent Application Publication No. 20060121005.

T cells can be expanded by contact with a surface having attached thereto an agent that stimulates a CD3/TCR complex associated signal and a ligand that stimulates a costimulatory molecule on the surface of the T cells. In some non-limiting examples, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3. XR-CD28 (Diacione, Besancon, France) can be used as can other methods commonly known in the art (Berg et al., Transplant Proc. 30(8)975-3977, 1998; Haanen et al., J. Exp. Med. 190(9): 13191328, 1999; Garland et A, J. Immunol. Meth. 227(1-2):53-63, 1999).

Once a CCR4 CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models.

Isolated immune cells expressing a CAR, such as T cells, for example CD3+ T cells such as CD4+ and/or CD8+ T cells, and/or NK cells, can be administered in a pharmaceutically acceptable carrier, such as buffered saline or another medium suitable for administration to a subject. The cells can be administered in conjunction with other cells, or in the absence of other cells. In one embodiment, compositions containing isolated populations of cells can also contain one or more additional pharmaceutical agents, such as one or more anti-microbial agents (for example, antibiotics, anti-viral agents and anti-fungal agents), anti-tumor agents (for example, fluorouracil, methotrexate, paclitaxel, fludarabine, etoposide, doxorubicin, or vincristine), depleting agents (for example, fludarabine, etoposide, doxorubicin, or vincristine), or non-steroidal anti-inflammatory agents such as acetylsalicylic acid, ibuprofen or naproxen sodium), cytokines (for example, interleukin-2), or a vaccine. Many chemotherapeutic agents are presently known in the art. In one embodiment, the chemotherapeutic agent is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

In other embodiments, a subject is administered the DNA encoding the CAR, to provide in vivo production Immunization by nucleic acid constructs is well known in the art and taught, for example, in U.S. Pat. Nos. 5,643,578, and 5,593,972 and 5,817,637. U.S. Pat. No. 5,880,103 describes several methods of delivery of nucleic acids encoding to an organism. The methods include liposomal delivery of the nucleic acids. Such methods can be applied to the production of an antibody, or antibody binding fragments thereof, by one of ordinary skill in the art.

One approach to administration of nucleic acids is direct administration with plasmid DNA, such as with a mammalian expression plasmid. The nucleotide sequence encoding the disclosed antibody, or antibody binding fragments thereof, can be placed under the control of a promoter to increase expression.

In another approach to using nucleic acids, a disclosed CAR can also be expressed by attenuated viral hosts or vectors or bacterial vectors. Recombinant vaccinia virus, adeno-associated virus (AAV), herpes virus, retrovirus, cytomegalovirus or other viral vectors can be used to express the antibody. For example, vaccinia vectors and methods useful protocols are described in U.S. Pat. No. 4,722,848. BCG (Bacillus Calmette Guerin) provides another vector for expression of the disclosed antibodies (see Stover, *Nature* 351:456-460, 1991). In a specific non-limiting example, the vector is a lentiviral vector.

In one embodiment, a nucleic acid encoding a disclosed CAR, is introduced directly into cells. For example, the nucleic acid can be loaded onto gold microspheres by standard methods and introduced by a device such as Bio-Rad's HELIOS™ Gene Gun. The nucleic acids can be "naked," consisting of plasmids under control of a strong promoter. The nucleic acid can be RNA; RNA encoding the CAR can be directly administered to the cells. In some embodiments, the cells are NK cells or T cells.

For the treatment of malignancy, the method can also include administering to the subject a therapeutically effective amount of an additional chemotherapeutic agent, surgery or radiation. In some embodiments, the malignancy is a lymphoid malignancy, such as adult T cell leukemia, cutaneous T cell lymphoma, anaplastic large cell lymphoma, Hodgkin's lymphoma, or a diffuse large B cell lymphoma. The subject can also have a solid tumor, such as, but not limited to, breast cancer, ovarian cancer, gastric cancer or esophageal cancer.

The chemotherapeutic agent can be an antibody. Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. The antibody can specifically bind programmed death (PD)-1 or programmed death ligand (PD-L1) (see below). Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

In further embodiments for the treatment of malignancies, a CAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Itzumoto et al. 2008 J Neurosurg 108:963-971. Exemplary chemotherapeutic agents include an anthracycline (e.g., doxorubicin (e.g., liposomal doxorubicin)). a vinca alkaloid (e.g., vinblastine, vincristine, vindesine, vinorelbine), an alkylating agent (e.g., cyclophosphamide, decatbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (ARIMIDEX®), bicalutamide (CASODEX®), bleomycin sulfate (BLENOXANE®), busulfan (MYLERAN®), busulfan injection (BUSULFEX®), capecitabine (XELODA®), N4-pentoxycarbonyl-5-deoxy-5-fluorocytidine, carboplatin (PARAPLATIN®), carmustine (BICNU®), chlorambucil (LEUKERAN®), cisplatin (PLATINOL®), cladribine (LEUSTATIN®), cyclophosphamide (CYTOXAN® or NEOSAR®), cytarabine, cytosine arabinoside (CYTOSAR-U®), cytarabine liposome injection (DEPOCYT®), dacarbazine (DTIC-DOME®), dactinomycin (Actinomycin D, Cosmegan), daunorubicin hydrochloride (CERUBIDINE®), daunorubicin citrate liposome injection (DAUNOXOME®), dexamethasone, docetaxel (TAXOTERE®), doxorubicin hydrochloride (ADRIAMYCIN®, RUBEX®), etoposide (VEPESID®), fludarabine phosphate (FLUDARA®), 5-fluorouracil (ADRUCIL®, EFUDEX®), flutamide (EULEXIN®), tezacitibine, Gemcitabine (difluorodeoxycitidine), hydroxyurea (HYDREA®), Idarubicin (IDAMYCIN®), ifosfamide (IFEX®), trinotecan (CAMPTOSAR®), L-asparaginase (ELSPAR®), leucovorin calcium, melphalan (ALKERAN®), 6-mercaptopurine (PURINETHOL®), methotrexate (FOLEX®), mitoxantrone (NOVANTRONE®), mylotarg, paclitaxel (TAXOL®), phoenix (Yttrium90/MX-D'IPA), pentostatin, polifeprosan 20 with carmustine implant (GLIADEL®), tamoxifen citrate (NOLVADEX®), teniposide (VUMON®), 6-thioguanine, thiotepa, tirapazamine (TIRAZONE®), topotecan hydrochloride for injection (HYCAMPTIN®), vinblastine (VELBAN®), vincristine (ONCOVIN®), and vinoreibine (NAVELRINE®). Exemplary alkylating agents include, without limitation, nitrogen mustards, ethylenimine derivatives, alkyl sulfonates, nitrosoureas and triazenes): uracil mustard (AMINOURACIL MUSTARD®, CHLORETHAMINACIL®, DEMETHYLDOPAN®, DESMETHYLDOPAN®, HAEMANTHAMINE®, NORDOPAN®, URACIL NITROGEN MUSTARD®, URACILLOST®, URACIL-MOSTAZA®, URAMUSTIN®, URAMUSTINE®), chlormethine (MUSTARGEN®), cyclophosphamide (CYTOXAN®, NEOSAR®, CLAFEN®, ENDOXAN®, PROCYTOX®, REVIMMUNE™), ifosfamide (MITOXANA®), melphalan (ALKERAN®), Chlorambucil (LEUKERAN®), pipobroman (AMEDEL®, VERCYTE®), triethylenemelamine (HEMEL®, HEXYLEN®, HEXASTAT®), triethylenethiophosphoramine, Temozolomide (TEMODAR®), thiotepa (THIOPLEX®), busulfan (BUSILVEX®, MYLERAN®), carrnustine (BiCNU®), lomustine (CEENU®), streptozocin (ZANOSAR®), and Dacarbazine (DTIC-DOME®). Additional exemplary alkylating agents include, without limitation, Oxaliplatin (ELOXATIN®); Temozolomide (TEMODAR® and TEMODAL®); Dactinomycin (also known as actinomycin-D, COSMEGEN®); Melphalan (also known as L-PAM, L-sarcolysin, and phenylalanine mustard, ALKERAN®); Altretamine (also known as hexamethylmelamine (HMM), HEXYLEN®); Carmustine (BICNUM; Bendamustine (TREANDAM; Busulfan (BUSULFEX® and MYLERAN®); Carboplatin (PARAPLATIN®); Lomustine (also known as CCNU, CEENU®); Cisplatin (also known as CDDP, PLATINOL® and PLATINOL®-AQ); Chlorambucil (LEUKERAN®); Cyclophosphamide (CYTOXAN® and NEOSAR®) Dacarbazine (also known as DTIC, DIC and imidazole carboxamide, DTIC-DOME®); Altretamine (also known as hexamethylmelamine (HMM), HEXYL EN®); Ifosfamide (IFEX®); Prednumustine; Procarbazine (MATULANE®); Mechlorethamine (also known as nitrogen mustard, mustine and mechloroethamine hydrochloride, MUSTARGEN®); Streptozocin (ZANOSAR®); Thiotepa (also known as thiophosphoamide, TESPA and TSPA, THIOPLEX®); Cyclophosphamide (ENDOXAN®, CYTOXAN®, NEOSAR®, PROCYTOX®, REVIMMUNE®); and Bendamustine HCl (TREANDA®). Exemplary mTOR inhibitors include, e.g., temsirolimus; ridaforolimus (formally known as deforolimus, (1R,2R,4S)-4-[(2R)-2[(1R,9S,12S,15R,16E,18R,19R, 21R, 23S,24E,26E,28Z,30S,32S,35R)-1,18-dihydroxy-19, 30-dimethoxy-15,17,21,23, 29,35-hexamethyl-2,3,10,14, 20-pentaoxo-11,36-dioxa-4-azatricyclo[30.3.1.0$^{4.9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (AFINITOR® or RAD001); rapamycin (AY22989, SIROLIMUS®); simapimod (CAS164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl] methoxy]butyl]-L- arginylglycyl-L-α-aspartylL-serine-, inner salt (SF1126, CAS 936487-67-1), and XL765. Exemplary immunomodulators include, e.g., afutuzumab (available from ROCHE®); pegfilgrastim (NEULASTA®); lenalidomide (CC-5013, REVLIMID®); thalidomide (THALOMID®), actimid (CC4047); and IRX-2 (mixture of human cytokines including interleukin 1, interleukin 2, and interferon γ, GAS 951209-71-5, available from IRX Therapeutics). Exemplary anthracyclines include, e.g., doxorubicin (Adriamycin® and RUBEX®); bleomycin (LENOXANE®); daunorubicin (dauorubicin hydrochloride, daunomycin, and rubidomycin hydrochloride, CERUBIDINE®); daunorubicin liposomal (daunorubicin citrate liposome, DAUNOXOME®); mitoxantrone (DHAD, NOVANTRONE®); epirubicin (ELLENCE™); idarubicin (IDAMYCIN®, IDAMYCIN PFS®); mitomycin C (MUTAMYCLN®); geldanamycin; herbimycin; ravidomycin; and desacetylravidomycin. Exemplary vinca alkaloids include, e.g., vinorelbine tartrate (NAVELBINE®), Vincristine (ONCOYIN®), and Vindesine (ELDISINE®)); vinblastine (also known as vinblastine sulfate, vincaleukoblastine and VLB, ALKABAN-AQ® and VELBAN®); and vinorelbine (NAVELBINE®). Exemplary proteosome inhibitors include bortezomib (VELCADE®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-serinamide (ONX-0912). Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B1, U.S. Pat. Nos. 7,812,135, 8,388,967, 8,591,886, European Patent No. EP 1866339, PCT Publication No. WO 2011/028683, PCT Publication No. WO 2013/039954, PCI Publication No. WO2005/007190, PCT Publication No. WO 2007/133822, PCT Publication No. WO2005/055808, PCT Publication No. WO 1999/40196, PCT Publication No. WO 2001/03720, PCT Publication No. WO 1999/20758, PCT Publication No. WO2006/083289, PCT Publication No. WO 2005/115451, U.S. Pat. No. 7,618,632, and PCT Publication No. WO 2011/051726.

For the treatment of an HIV infection, the subject can be administered an antiretroviral agent. Antiretroviral drugs are broadly classified by the phase of the retrovirus life-cycle that the drug inhibits. The disclosed antibodies can be administered in conjunction with Nucleoside and nucleotide reverse transcriptase inhibitors (nRTI), Non-nucleoside reverse transcriptase inhibitors (NNRTI), Protease inhibitors, Entry inhibitors (or fusion inhibitors), Maturation inhibitors, or a Broad spectrum inhibitors, such as natural antivirals. Exemplary agents include lopinavir, ritonavir, zidovudine, lamivudine, tenofovir, emtricitabine and efavirenz.

In some embodiments, the subject can be administered an agent which enhances the activity of a CAR-expressing cell. For example, in one embodiment, the agent can be an agent which inhibits an inhibitory molecule. Inhibitory molecules, e.g., Programmed Death 1 (PI)-1), can, in some embodiments, decrease the ability of a CAR-expressing cell to mount an immune effector response. Examples of inhibitory molecules include PD-1, PD-L1, CTLA4, TIM3, LAW, VISTA, BTLA, TIGIT, LAIR1, CD160, 2B4 and TGFR-beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., a siRNA or shRNA, can be used to inhibit expression of an inhibitory molecule in the CAR-expressing cell. In an embodiment the inhibitor is a shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR. In one embodiment, the inhibitor of an inhibitory signal can be, e.g., an antibody or antibody fragment that binds to an inhibitory molecule. For example, the agent can be an antibody or antibody fragment that binds to PD-1, PD-L1, PD-L2 or CTLA4 (e.g., ipilim.umab (also referred to as MDX-010 and MDX-101, and marketed as YERVOY®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3.

Programmed Death (PD)-1 is an inhibitory member of the family of receptors that also includes CD28, CTLA-4, ICOS, and BILA. PD-1 is expressed on activated B cells, T cells and myeloid cells (Agata et al. 1996 Int. Immunol 8:765-75). Two ligands for PD-1, PD-L1 and PD-L2 have been shown to downregulate T cell activation upon binding to PD-1 (Freeman et al. 2000 J Exp Med 192:1027-34; Latchman et al. 2001 Nat Immunol 2:261-8; Carter et al. 2002 Eur Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD-1 with PD-L1. Antibodies, antibody fragments, and other inhibitors of PD-1, PD-LI and PD-L2 are available in the art and may be used combination with a CCR4 CAR described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and PCT Publication No. WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in PCT Publication No. WO02009/101611. Lambrolizumab (also referred to as MK03475; Merck) is a humanized IgG4 monoclonal antibody that binds to PD-1. Lambrolizumab and other humanized anti-PD-1 antibodies are disclosed in U.S. Pat. No. 8,354,509 and PCT Publication No. WO2009/114335. MDPL3280A (Genentech/ Roche) is a human Fc optimized $IgG_1$ monoclonal antibody that binds to PD-L1. MDPL3280A and other human monoclonal antibodies to PD-L1 are disclosed in U.S. Pat. No. 7,943,743 and U.S. Publication No. 2012/0039906. Other anti-PD-L1 binding agents include YW243.55.570 (heavy and light chain variable regions are shown in SEQ ID NOs: 20 and 21 in PCT Publication No. WO2010/077634) and MDX-1 105 (also referred to as BMS-936559, and, e.g., anti-PD-L1 binding agents disclosed in PCT Publication No. WO2007/005874). AMP-224 (B7-DCIg: Amplimmune; e.g., disclosed in PCI Publication No. WO2010/027827 and PCT Publication No. WO2011/066342), is a PD-L2 Fc fusion soluble receptor that blocks the interaction between PD-1 and Other anti-PD-1 antibodies include AMP 514 (Amplimmune), among others, e.g., anti-PD-1 antibodies disclosed in U.S. Pat. No. 8,609,089, U.S. Publication No. 2010/028330, and/or U.S. Publication No. 2012/0114649.

Kits

Kits are also provided. For example, kits for treating a subject with a cancer that expresses CCR4, or for HIV. The kits will typically include a disclosed nucleic acid encoding a CAR, T cell expressing a CA or compositions including such molecules.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, or compositions. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of the antibodies, antigen binding fragments, conjugates, nucleic acid molecules, or compositions included in the kit. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

There has been emerging success of treating CD19 expressing B cell malignancies with ex vivo modified, autologous T cells that express CD19-directed chimeric antigen receptors (CAR). This technology can be expanded to develop effective modalities to treat other malignancies including solid tumors. A lentivirus-based CAR gene transfer system was generated to target the chemokine receptor CCR4 that is over-expressed in a spectrum of T cell malignancies as well as in CD4$^+$CD25$^+$Foxp3$^+$ T regulatory cells that accumulate in the tumor microenvironment constituting a barrier against anti-tumor immunity. It is disclosed herein that ex vivo modified, donor-derived T cells that expressed CCR4 directed CAR displayed antigen-dependent potent cytotoxicity against patient-derived cell lines representing ATL, CTCL, ALCL and a subset of HDL. Furthermore, these CAR T cells also eradicated leukemia in a mouse xenograft model of ATL illustrating the potential utility of this modality in the treatment of a wide spectrum of T cell malignancies.

Example 1

Materials and Methods

Construction of CCR4 Chimeric Antigen Receptor and Lentiviral Stock Preparation

Humanization of anti-human CCR4 monoclonal antibody 1567 and its affinity matured variant mAb2-3 has been reported (Chang et al., *Mol Cancer Ther.* 2012; 11(11):2451-2461, incorporated herein by reference) along with the amino acid sequence of the variable heavy (VH) and variable light (VL) kappa domains of mAb2-3 and these sequences were utilized in the construction of our CCR4 CAR construct and its molecular configuration is depicted in FIG. 1A. The amino acid sequences of CD8 hinge and transmembrane domain, 4-1BB (CD137) signaling module, and CD3ξ signaling module were derived from GENBANK® Accession Nos. NM_001768, U03397.1, and NM_00734, respectively, which are incorporated herein by reference. The individual domain sequences were assembled into one transcriptional/translational unit and a codon-optimized DNA sequence of the functional unit was synthesized de novo. The synthetic DNA fragment was then cloned into the CSII-EF-MCS-IRES-Venus plasmid. The resultant expression plasmid was then co-transfected with lentiviral packaging helper plasmids pCAG-H1Vgp (CAG promoter, HIV-1 gag and pol expression plasmid) and pCMV-VSV-G into human embryonic kidney cells HEK 293T to generate stocks of CCR4 CAR-encoding lentiviral particles (second generation non-replicative). Following transfection of HEK 293T cells, the culture supernatant was harvested 48 hrs later and clarified by centrifugation at 2500 rpm for 10 min and passing through a 0.45 micron filter. The clarified supernatant was then subjected to ultracentrifugation at 24000 rpm for 2 hours at 4° C. The CCR4 CAR lentiviral pellet was then dissolved in a volume of PBS to achieve a 1000-fold concentration, and stored at −80° C. until used.

Cells and culture conditions: The growth of ATL cell lines ED-40515(+), ATL55T(+), KOB, LM-Y1, KK1, ATL-43T (+) and ED-41214(+) are IL-2 dependent, while ED-40515 (−), ST1, ATL-43Tb(−), Su9T01, ATN1, ED-41214C(−) and MT1 are IL-2 independent and have been described (Nakagawa et al., *J Exp Med.* 2014; 211(13):2497-2505). Cutaneous T cell lymphoma cell lines HH, HuT78, MJ, HuT102 were obtained from the American Type Culture Collection. Mac-1, Mac-2A, and Mac2-B cell lines are derived from ALK-negative ALCL whereas Karpas299, SUDHL-1, SR-786, SUP-M2 and DEL are derived from ALK-positive ALCL. Hodgkin's cell lines L428, HDLM-2, KM-H2, and L1236 and SUDHL-4 derived from a diffuse large B cell lymphoma devoid of detectable CCR4 mRNA were also used. The cell line ATL41214 is a derivative of ED-41214C (−) with an integrated luciferase gene driven from the CMV promoter. The above cell lines were cultured in RPMI with 10% fetal calf serum. Peripheral blood mononuclear cells from healthy volunteer donors were obtained under an approved protocol with informed consent. For culturing human lymphocytes, AIM-V (Invitrogen) medium supplemented with 10% human AB serum (Invitrogen) and 300 IU/ml recombinant human IL-2 (Peprotec) was used.

T cell transduction: A Pan-T cell isolation kit (Miltenyi Biotec) was used to purify untouched T cells from human peripheral blood mononuclear cells and the cells were then activated in the presence of 30 IU/ml IL-2 by adding Dynabeads T activator CD3/CD28 beads (Life Technologies) at 3 beads per 1 cell ratio for 48 hours. A retronectin-coated dish (Takara Bio) was first pre-centrifuged for 2 hours at 2000 g after adding CCR4 CAR lentiviral particles to adsorb lentiviral particles to the plate surface at 32-35° C. and the activated T cells (1×10$^6$) were then added into the dish. The IL-2 concentration in the culture medium was then increased to 300 IU/ml and the cells were expanded at 37° C. by feeding with fresh medium every 2 days while maintaining a cell density around 1-3×10$^6$ cells/ml.

Flow cytometry: For immunophenotyping CCR4 CAR transduced T cells, one million cells were stained with CD4-PerCP, CD8-APC or Protein L-Biotin (Thermo Scientific) (Zheng et al., *J Transl Med.* 2012; 10:29). The presence of cell surface-bound Protein L was detected with SA-PerCP.

Cellular cytotoxicity: The cytotoxic effector activity of CCR4 CAR T cells was determined either using a standard 4-hour $^{51}$Cr release assay (Phillips et al., *Cancer Res.* 2000; 60(24):6977-6984) or a biophotonic cytotoxicity assay (Brown et al., *J Immunol Methods.* 2005; 297(1-2):39-52) using the ATL41214 cell line and measuring bioluminescence with the addition of D-luciferin (0.14 mg/ml final centration per well from Xenogen) at the indicated time points using a microplate counter/luminometer (PerkinElmer). Percent specific lysis calculated using the following formula:

$$\% \text{ lysis} = \frac{[1 - (CPS_{experimental} - CPS_{min})]}{(CPS_{max} - CPS_{min})} \times 100$$

Cell proliferation assay: CCR4 CAR-modified T cells ($0.5 \times 10^5$) were co-cultured with either $1 \times 10^4$ ATL55T(+) (CCR4 positive) or SUDHL-4 cells (CCR4 negative) that were irradiated with a dose of 3000 rads for 72 hours in triplicate. Controls included were CAR-modified T cells cultured alone, ATL55T(+) cells cultured alone, and SUDHL-4 cells cultured alone. During the last 6 hours of co-culture period, the cells were pulsed with 1 µCi of [$^3$H]thymidine. The incorporation of [$^3$H]thymidine was measured in a β-counter (PerkinElmer).

Cytokine measurement: CCR4 CAR-modified T cells ($0.5 \times 10^5$) were co-cultured with either ATL55T(+) or SUDHL-4 cells ($1 \times 10^4$) that were irradiated with a dose of 3000 rads for 24 hours in triplicate. Controls included were CAR-modified T cells cultured alone, ATL55T(+) cells cultured alone and SUDHL-4 cells cultured alone. The culture supernatants were harvested and the cytokines were measured using a V-PLEX human cytokine 30-Plex kit according to instructions provided by the manufacturer and the fold-change was calculated based on values obtained for CAR-modified cells cultured alone versus those co-cultured with ATL55T cells.

Detection of CCR4 mRNA transcripts by Taqman real-time quantitative PCR: Total cellular RNA was isolated using a commercial kit (RNEASY® mini kit from Qiagen). Reverse transcription (RT) reactions were carried out for each sample (60 ng) using the Superscript IIII First-Strand Synthesis System (Invitrogen). The TAQMAN® Gene Expression Master Mix, the human CCR4 primer/probe (Assay ID: Hs00747615_s1) and the HPRT1 primer/probe (Cat. #4333768F) were purchased from Life Technologies (Foster City, Calif.). Relative quantitation of human CCR4 and HPRT1 were performed using an ABI7500 Real Time Sequence Detection System (Life Technologies) according to the manufacturer's instructions. Target gene expression was calculated using the comparative method for relative quantity upon normalization to housekeeping HPRT1 gene expression.

In vivo studies: Ten million ATL41214 ATL cells were inoculated intraperitonealy in a volume of 100 microliters into groups of NSG mice (NOD scid gamma, NOD.Cg-Prkdc$^{rm1 Wj1}$/SzJ JAX, Jackson Laboratories). After a three-day period of engraftment, the treatment group of mice was injected intraperitoneally with CAR-modified T cells ($1 \times 10^7$ cells/animal) and received daily intraperitoneal injections of human IL-2 (600 IU) for 7 days thereafter. Tumor burdens were measured using a Xenogen IVIS imaging system (Caliper Life Science) weekly after injecting 3 mg of D-luciferin/mouse intraperitoneally. The software Living Image version 4.1 was used to analyze bioluminescent signals as photon/s/cm2/sr.

Example 2

Production and Use of the Chimeric Antigen Receptor Modified T Cells

Figure 2C:
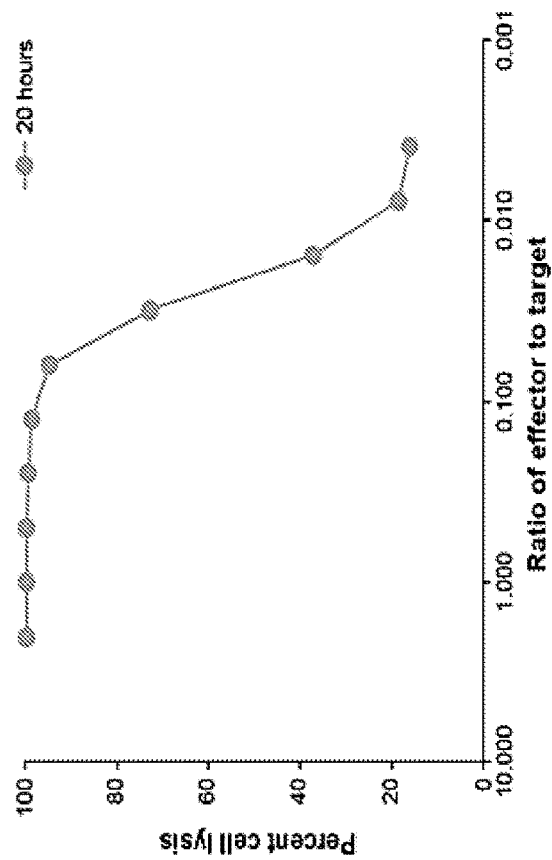
Figure 2B:
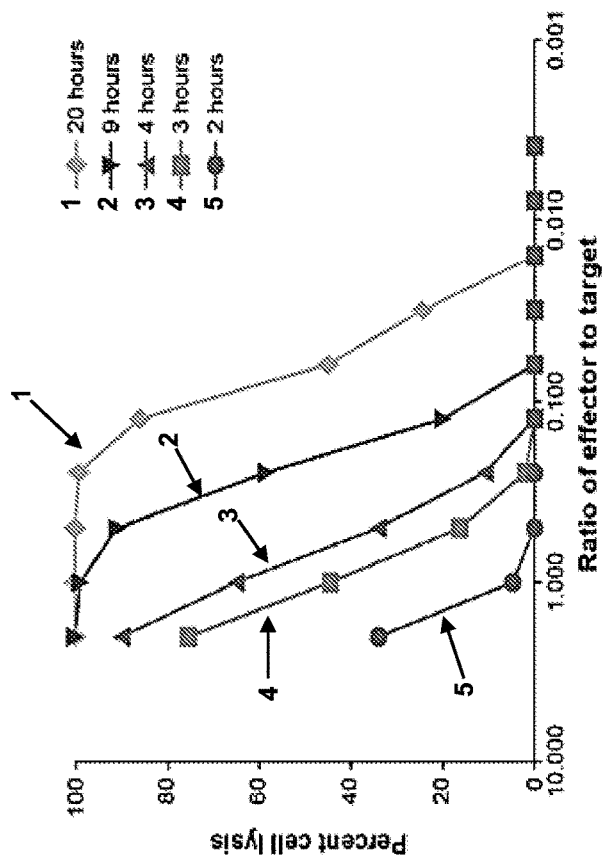

The structural configuration of a CAR molecule is depicted in FIG. 1A which includes a transmembrane module derived from the human CD8 molecule along with two intracellular signaling modules derived from 4-1BB (CD137) and CD3ζ in addition to the extracellular CCR4-binding domains derived from a humanized anti-CCR4 antibody. Donor derived, activated CD3$^+$ T cells were transduced once and over 80% transduction efficiency was routinely achieved as determined by GFP positivity and Protein L binding activity by flow cytometry (FIG. 1, panels B and C). The representation of CD4$^+$ and CD8$^+$ subsets in the transduced cell population is depicted in panels D and E of FIG. 1, after a period of 72 hours post transduction in culture. Having confirmed the robust expression of CCR4 targeting CAR in the transduced T cells, the functional activity of these CCR4-directed CAR transduced CD3+ T cells was then evaluated. The cell line ATL 41214 has been derived from a patient with HTLV-1 associated chronic adult T cell leukemia and expresses cell-surface CCR4 whereas YT-1 cell line that has been derived from a patient with EBV associated NK lymphoma does not express CCR4 (see FIG. 2, panel A). Previously, stable derivatives of these two cell lines were created that express luciferase reporter gene and the availability of these luciferase-tagged cell lines enabled their use a sensitive bioluminescence-based cytolytic assay. As shown in FIG. 2B, cytolytic activity was evident by 120 minutes of co-culture of target and effector cells that continued to increase throughout the observation period of 20 hours. Moreover, the ability of these CAR T cells to engage in multiple rounds of killing was evident by the data, especially when one considers the percentage of killing activity at low effector:target ratios that continued to increase over time thus validating the robust functionality of this CAR.

Figure 2D:
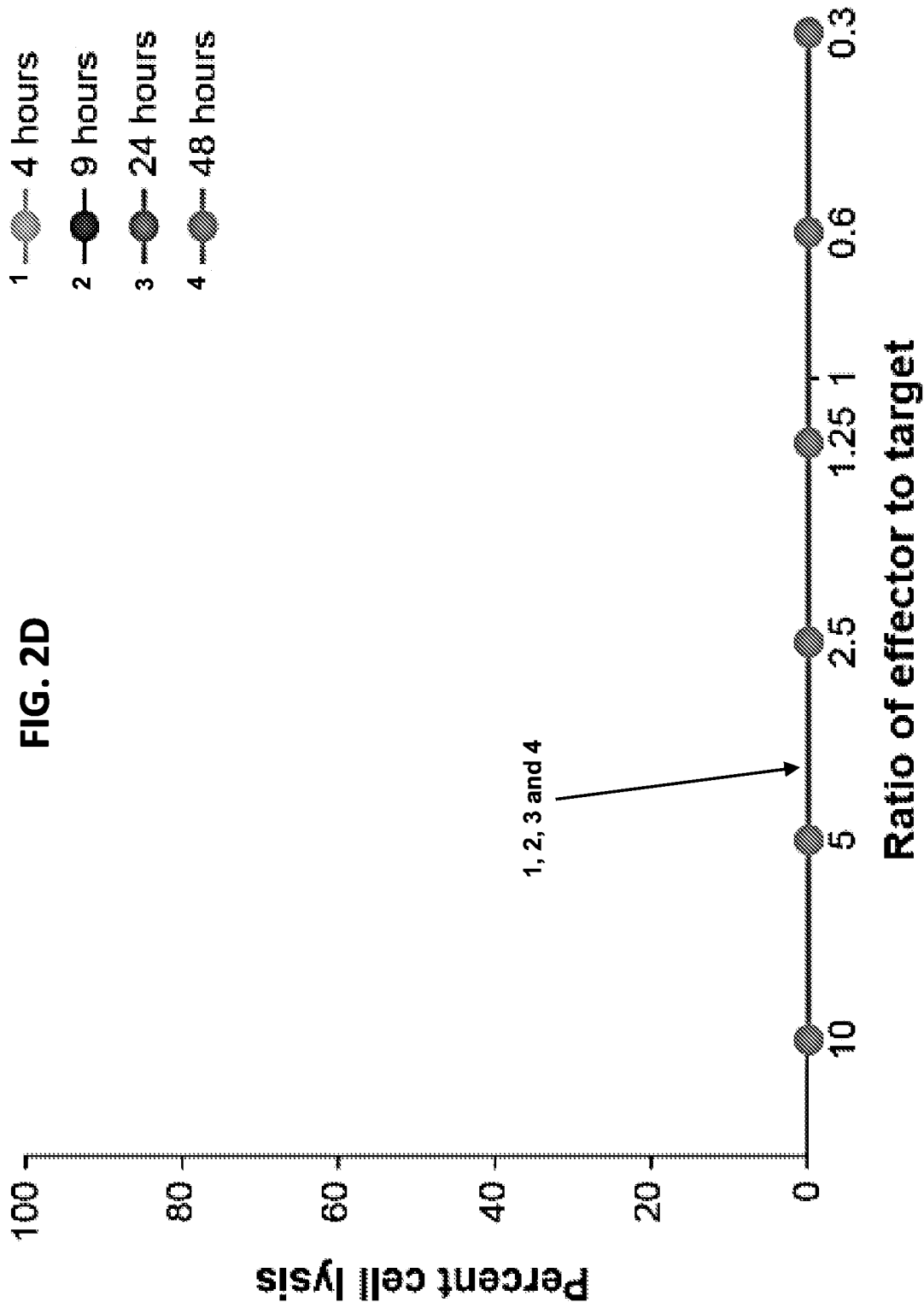

In most if not all clinical trials reported to date, the emphasis has been to limit the ex vivo CD28-based expansion phase to a period of 10-12 days to ensure an optimal state of differentiation with minimal telomere degradation and the avoidance of possible senescence or exhaustion of the cells that are being transfused. In exploring this issue further, after the initial 12-day, CD28-based expansion, expansion of CAR T cells was continued with irradiated ED-41214C(−) cells in the presence of IL-2 (300 IU/ml). Surprisingly, the CAR T cells continued to expand robustly even up to 8 weeks and still retained equal potency in lysing target cells bearing CCR4 (FIG. 2C). In contrast, no cytolytic activity was observed when CCR4 CAR T cells were co-cultured with YT-1 cells thus validating the robust functionality and specificity of this CCR4 CAR (FIG. 2D).

Figure 3D:
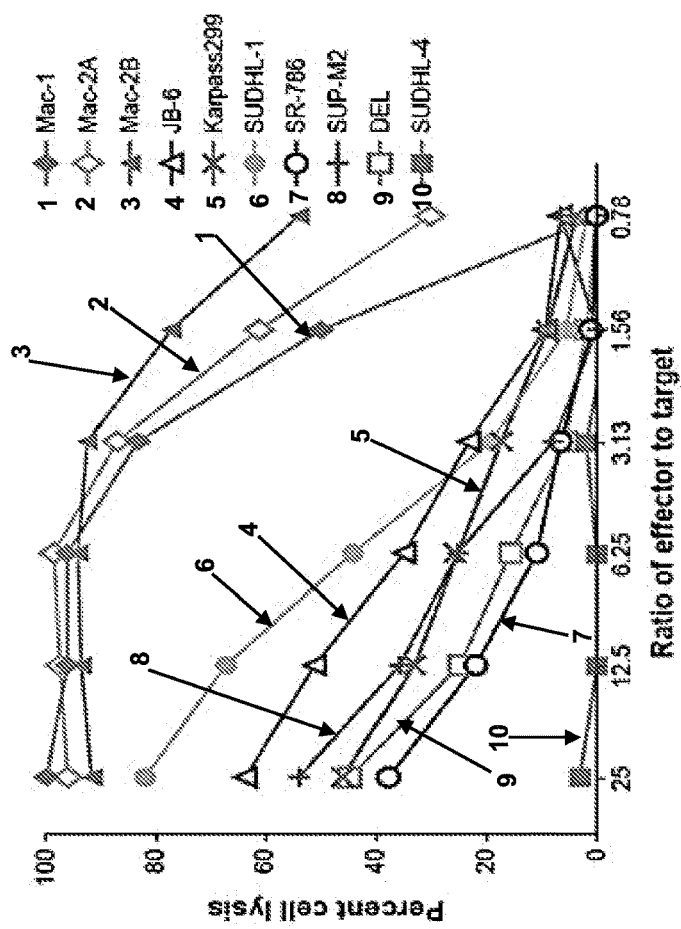
Figure 3C:
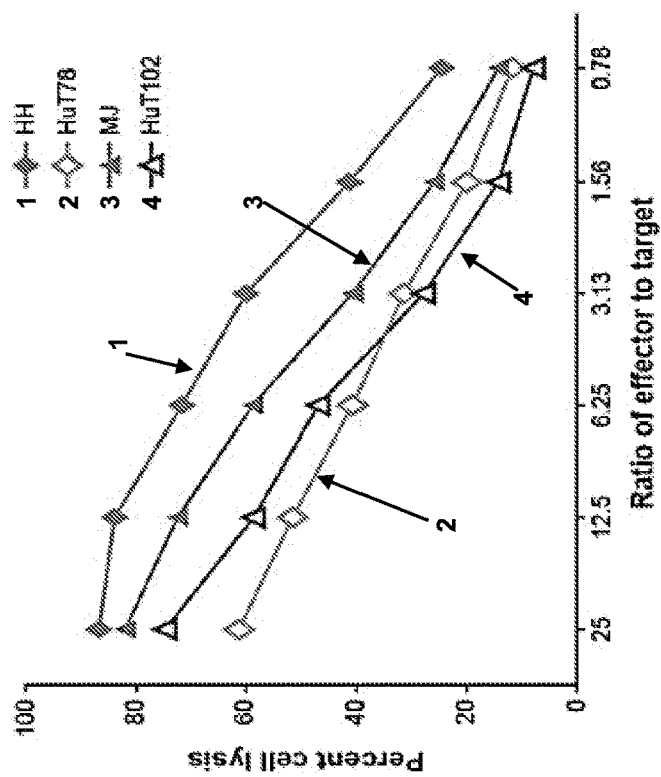
Figure 3E:
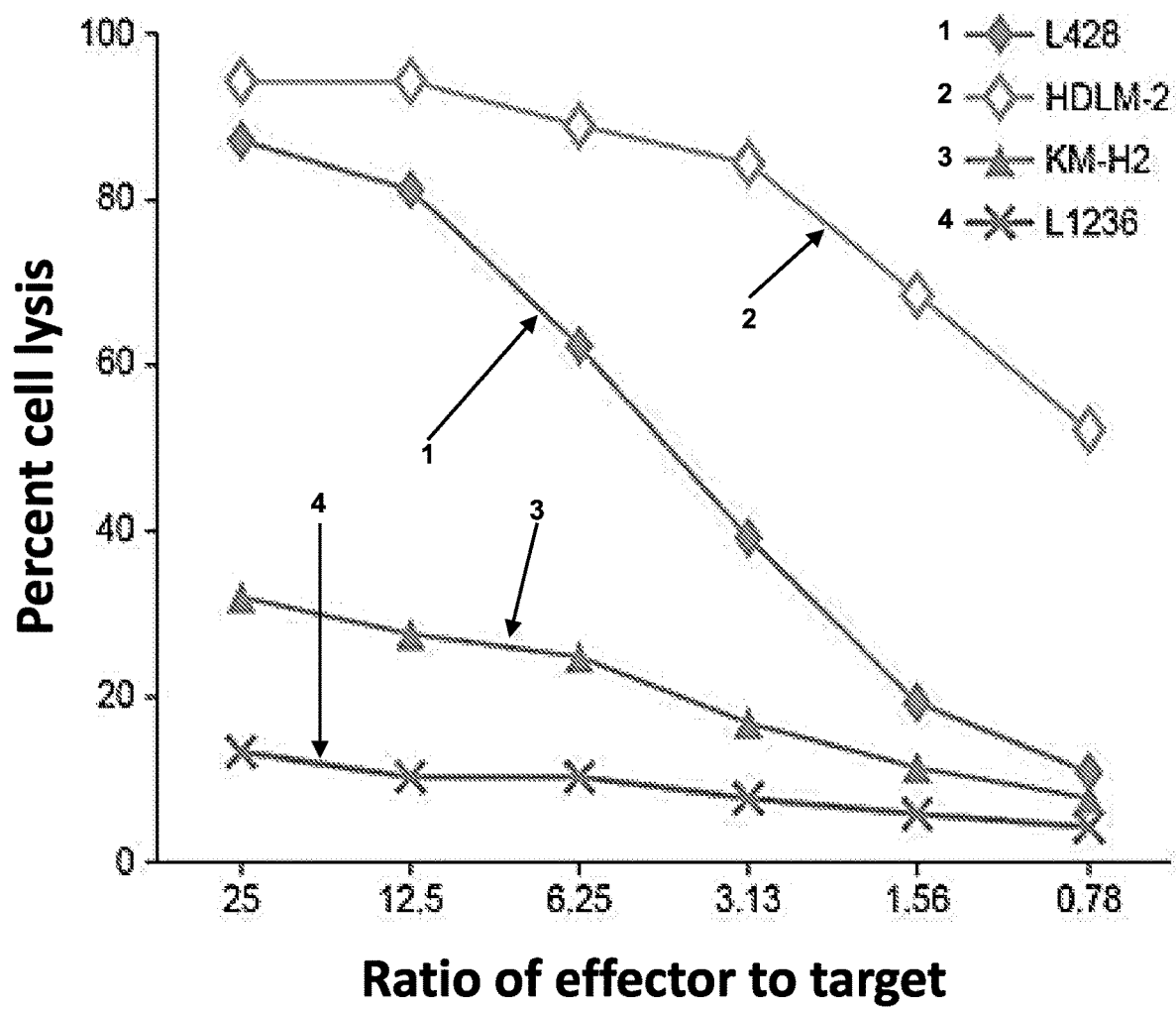

To assess the broader utility of CCR4-directed CAR approach, a panel of patient derived malignant cell lines representing a spectrum of lymphoid malignancies was used to assess their sensitivity to CCR4 CAR transduced donor derived CD3+ T cells (FIG. 3). The cell lines ED-40515(+), ATL55T(+), KOB, LM-Y1, KK1, ATL-43T(+) and ED-41214(+) represent chronic/smoldering adult T cell leukemia and are IL-2 dependent for their growth (panel A), while ED-40515(−), ST1, ATL-43Tb(−), Su9T01, ATN1, ED-41214C(−) and MT1 are from acute adult T cell leukemia patients and are not dependent on IL-2 for growth (panel B). The cell lines HH, HuT78, MJ, HuT102 represent cutaneous T cell lymphomas (panel C). The cell lines Mac-1, Mac-2A, and Mac2-B cell lines were derived from anaplastic large cell lymphoma without chromosome t(2;5) translocations and are thus ALK (anaplastic lymphoma kinase) negative whereas Karpas299, SUDHL-1, SR-786, SUP-M2 and DEL have been derived from ALK-positive ALCL (panel D). Hodgkin cell lines L428, HDLM-2, KM-H2, and L1236 were also included in the analysis as well SUDHL-4 derived from a diffuse large B cell lymphoma (panel E).

Almost all cell lines derived from T-cell malignancies were susceptible to lysis by CCR4 CAR T cells although the level of sensitivity varied somewhat among the cell lines tested. In the panel of ALCL cell lines tested, there was clear separation of ALK negative cell lines (Mac-1, Mac-2A, and Mac-2B) as a group being more sensitive than the ALK positive cell lines. With HDL cell lines, HDLM-2 which is of T-cell origin and L428 of B-cell origin both displayed significant sensitivity while the other HDL cell lines were refractory as was SUDHL-4, a DLBCL-derived cell line.

Figure 4:
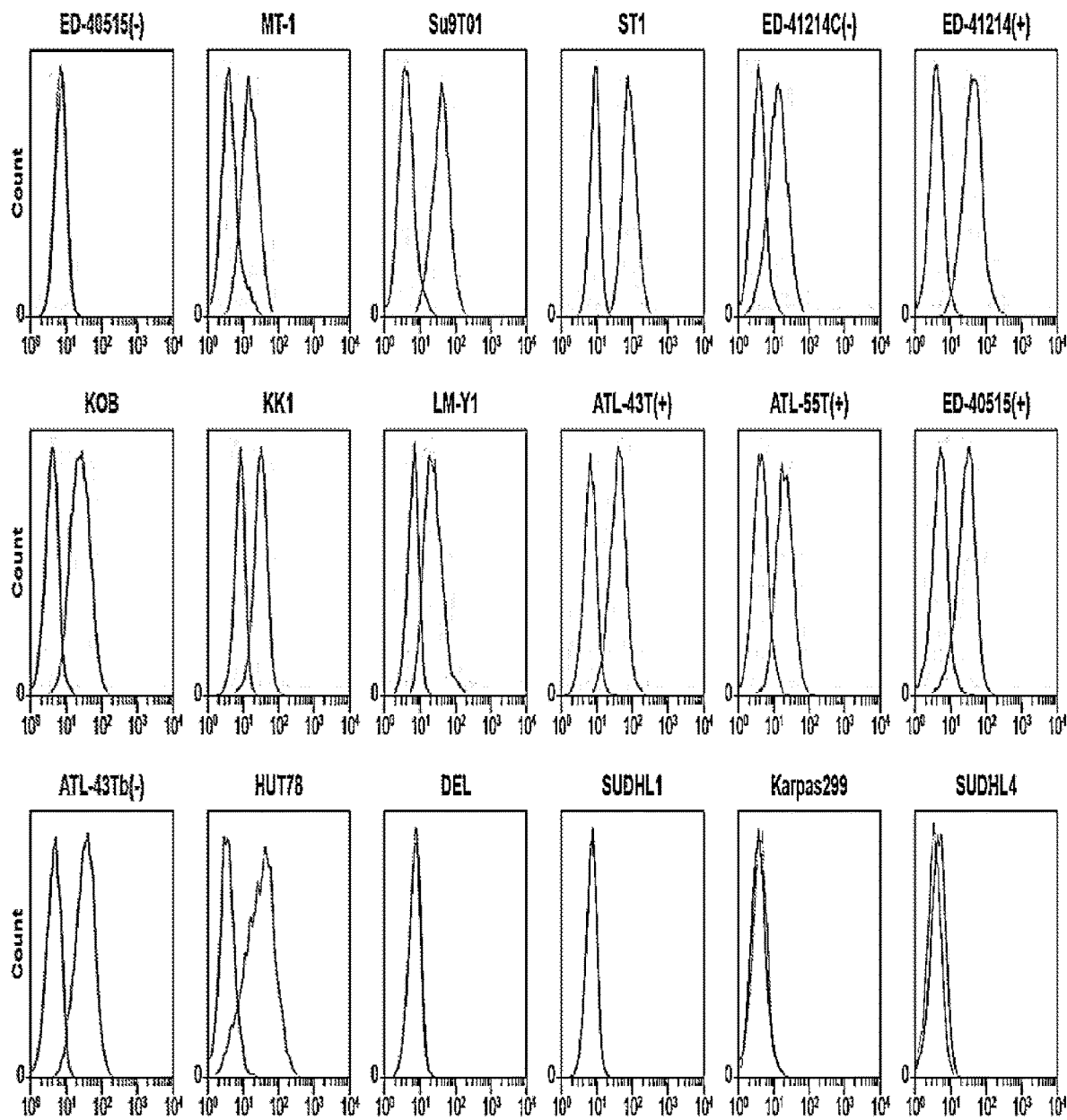
FIG. 4: Cell surface expression of CCR4 in a panel of patient derived neoplastic cell lines by flow cytometry. Each cell line was surface-stained with an anti-human CCR4-APC antibody (clone D8SEE from EBIOSCENCE®) depicted in blue or an isotype matched control antibody conjugated APC depicted in red. Stained cells were analyzed on a FACSCALIBUR® (BD).
Figure 5A:
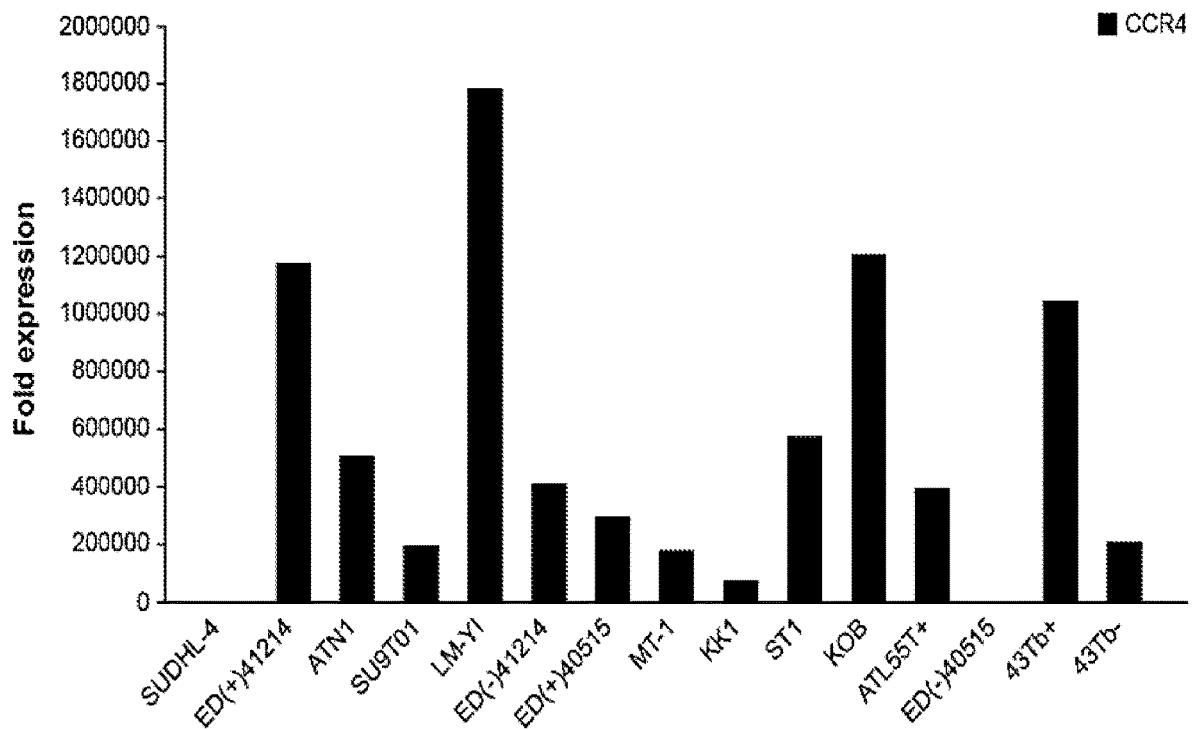
FIGS. 5A-5B: CCR4 CAR T cell cytotoxicity and proliferative activities correlate with CCR4 expression in target tumor cells. (A) mRNA transcript levels of CCR4 were determined by TAQMAN® real time quantitative PCR after isolating total cellular RNA from a select set of tumor cell lines used in FIG. 3, including the two cell lines SUDHL-4 and ED-40515(−) that were refractory to CCR4 CAR T cell mediated killing. Fold expression was calculated upon normalization to housekeeping HPRT1 gene expression. (B) As a measure of functional capacity of the CCR4 CAR in transducing a proliferative signal, CCR4 CAR T cells were co-cultured with either ATL55T(+) cells that express CCR4 or SUDHL-4 cells that are devoid of CCR4 after irradiating them. After a 24-hour period of co-culture, the incorporation of [$^3$H]thymidine was measured.
Figure 5B:
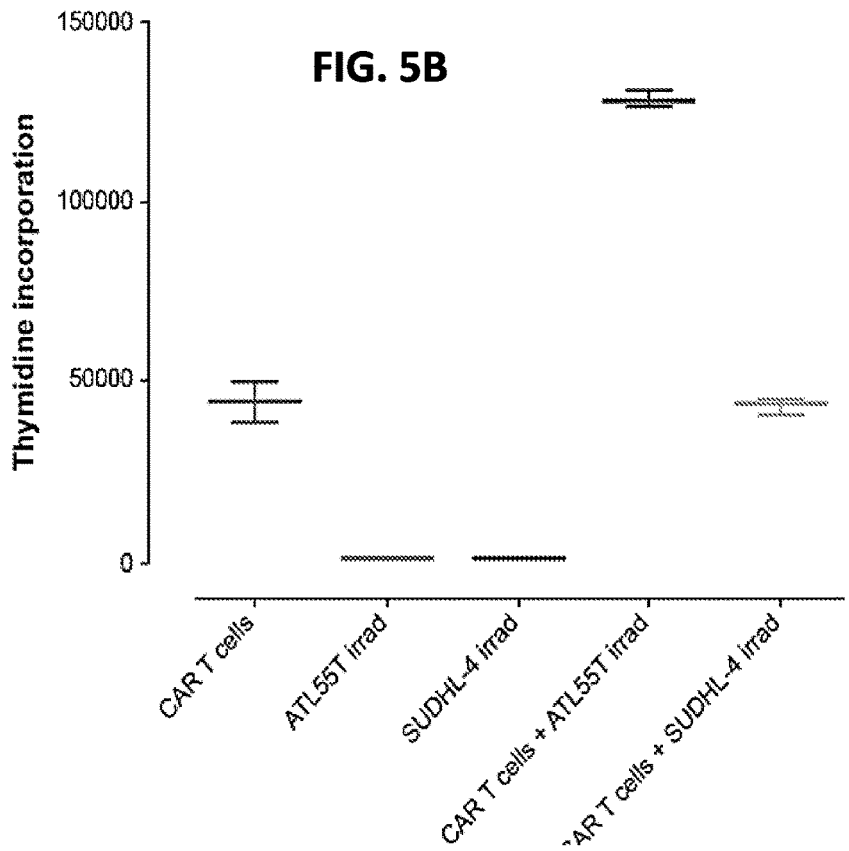

While all CTCL and ATL cell lines were quite sensitive, the exception was ED(–) 40515 that was refractory, prompting exploration of the cell surface CCR4 levels in ATL cell lines as a way of explaining the differences in sensitivity. The surface expression of CCR4 was determined on these cell lines by flow cytometry and most of them were found to have detectable levels of CCR4 on their cell surface (see FIG. 4). The cell surface expression of CCR4 as detected by flow cytometry did not appear to be a very sensitive measure for quantitative analysis although the trend of cell surface CCR4 levels generally paralleled their sensitivity to CCR4 CAR mediated cytolysis. However, certain cell lines such as SUDHL-1, Karpas299, and DEL, despite being negative for CCR4 expression by flow cytometry, were not totally refractory to CCR4 CAR T cells. Therefore, the CCR4 mRNA levels was measured in these cell line by quantitative PCR (TAQMAN®) (see FIG. 5A, and Table 2 below) and a better co-relation between CCR4 mRNA levels was observed than the cell surface CCR4 expression by flow cytometry with the lytic susceptibility (see FIG. 5). For example, SUDHL-4 and ED-40515 that were devoid of CCR4 mRNA were also refractory to CCR4 CAR T cell mediated cytolysis in addition to YT-1 cells, see FIG. 2D. Further delineating the functionality of CCR4 CAR, the strength of the proliferative signal was measured by co-culture of CAR T cells with irradiated CCR4-bearing target cells. An increase over 3-fold in $H^3$thymidine incorporation was found within a period of 72 hours (FIG. 5B).

In a parallel experiment, the cytokines/chemokines that were elicited by co-culture of target cells with CCR4 CAR T cells were measured for a period of 24 hours (Table 1).

TABLE 1

| Cytokine/chemokine | *Fold-induction |
|---|---|
| GM-CSF | 5 |
| IL-5 | 4 |
| TNF-alpha | 8 |
| TNF-beta | 5 |
| IFN-gamma | 2 |
| IL-13 | 3 |
| IL-4 | 9 |
| IL-8 | 4 |
| MDC | 2 |

*CCR4 CAR T cells were co-cultured with irradiated ATL55T cells (5:1 ratio) for 24 hours as described in Example 1 and the cytokine/chemokine levels in the supernatants measured using a V-PLEX multiplex kit.

TABLE 2

Quantitative assessment of CCR4 mRNA levels in neoplastic T cell lines studied.

| cell line | CCR4 | STDEV | HPRT1 | STDEV | Fold expression [2 (– Ct)] |
|---|---|---|---|---|---|
| SUDHL-4 | 38.5 | 0.7 | 20.8 | 0.2 | 1.0 |
| ED41214 (+) | 19.9 | 0.2 | 22.3 | 0.2 | 1185173.4 |
| ATN1 | 21.0 | 0.1 | 22.2 | 0.1 | 520546.2 |
| SU9T01 | 23.1 | 0.1 | 23.0 | 0.1 | 206531.2 |
| LM-Y1 | 19.1 | 0.1 | 22.2 | 0.1 | 1793898.3 |
| ED41214 (–) | 21.3 | 0.1 | 22.3 | 0.2 | 423303.6 |
| ED40515 (+) | 22.6 | 0.4 | 23.1 | 0.1 | 306246.4 |
| MT-1 | 21.7 | 0.1 | 21.5 | 0.1 | 189302.4 |
| KK1 | 23.3 | 0.1 | 22.0 | 0.2 | 85462.3 |
| ST1 | 19.9 | 0.2 | 21.3 | 0.0 | 589582.2 |
| KOB | 19.3 | 0.2 | 21.8 | 0.1 | 1215400.2 |
| ATL55T+ | 20.3 | 0.2 | 21.1 | 0.1 | 401952.8 |
| ATL43T (+) | 19.1 | 0.1 | 21.4 | 0.1 | 1058311.8 |
| ATL43Tb (–) | 21.3 | 0.0 | 21.4 | 0.1 | 218610.0 |
| MAC-1 | 21.5 | 0.0 | 24.0 | 0.0 | 227985.6 |
| MAC-2A | 22.1 | 0.0 | 24.2 | 0.1 | 179196.5 |
| MAC-2B | 19.6 | 0.1 | 24.5 | 0.0 | 1227776.6 |
| ED40515 (–) | 38.4 | 0.6 | 24.3 | 0.0 | 2.4 |
| DEL | 36.1 | 0.3 | 25.1 | 0.0 | 20.1 |
| Karpass299 | 31.7 | 0.2 | 23.5 | 0.1 | 148.6 |
| SUDHL-1 | 36.0 | 0.4 | 23.4 | 0.1 | 7.0 |

Transcript levels of CCR4 were determined by TaqMan real time quantitative PCR after isolating total cellular RNA from a select set of tumor cell lines used in FIG. 3, The values in CCR4 and HPRT1 columns represent the means of experiments done in triplicate. Fold expression was calculated (2^–ΔΔCt) upon normalization to housekeeping HPRT1 gene expression using vendor provided software.

Figure 6A:
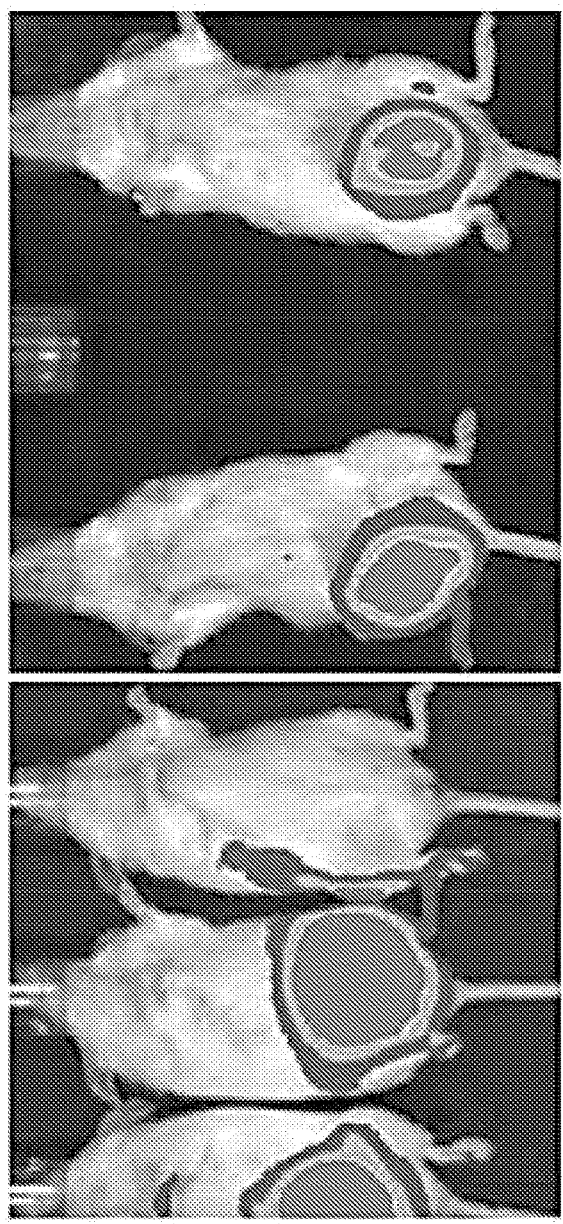
FIGS. 6A-6B: CCR4 CAR T cells show in vivo efficacy. A cohort of NSG mice were administered with 10 million ATL41214/Luc cells intraperitoneally. Three days later, one half of the cohort (n=5) were administered with 10 million donor T cells transduced with a lentivector expressing GFP intraperitoneally (A) while the other half received donor T cells modified ex vivo with the CCR4 CAR lentivector intraperitoneally (B). Following the administration of donor T cells, mice were injected daily with 600 IU human IL-2 for a period of 7 days intraperitoneally. The efficacy of CCR4 CAR T cells was assessed by bioluminescent imaging to measure the extent of tumor growth 4 weeks after the administration of donor T cells.
Figure 6B:
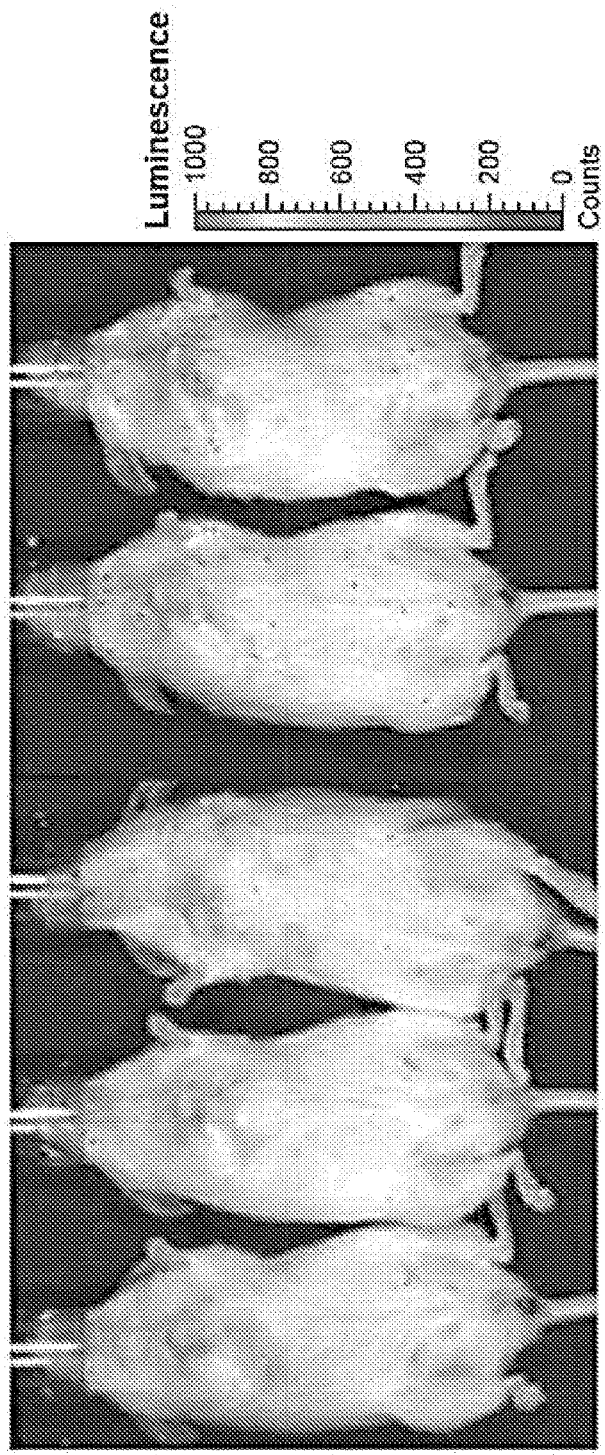
Figure 9:
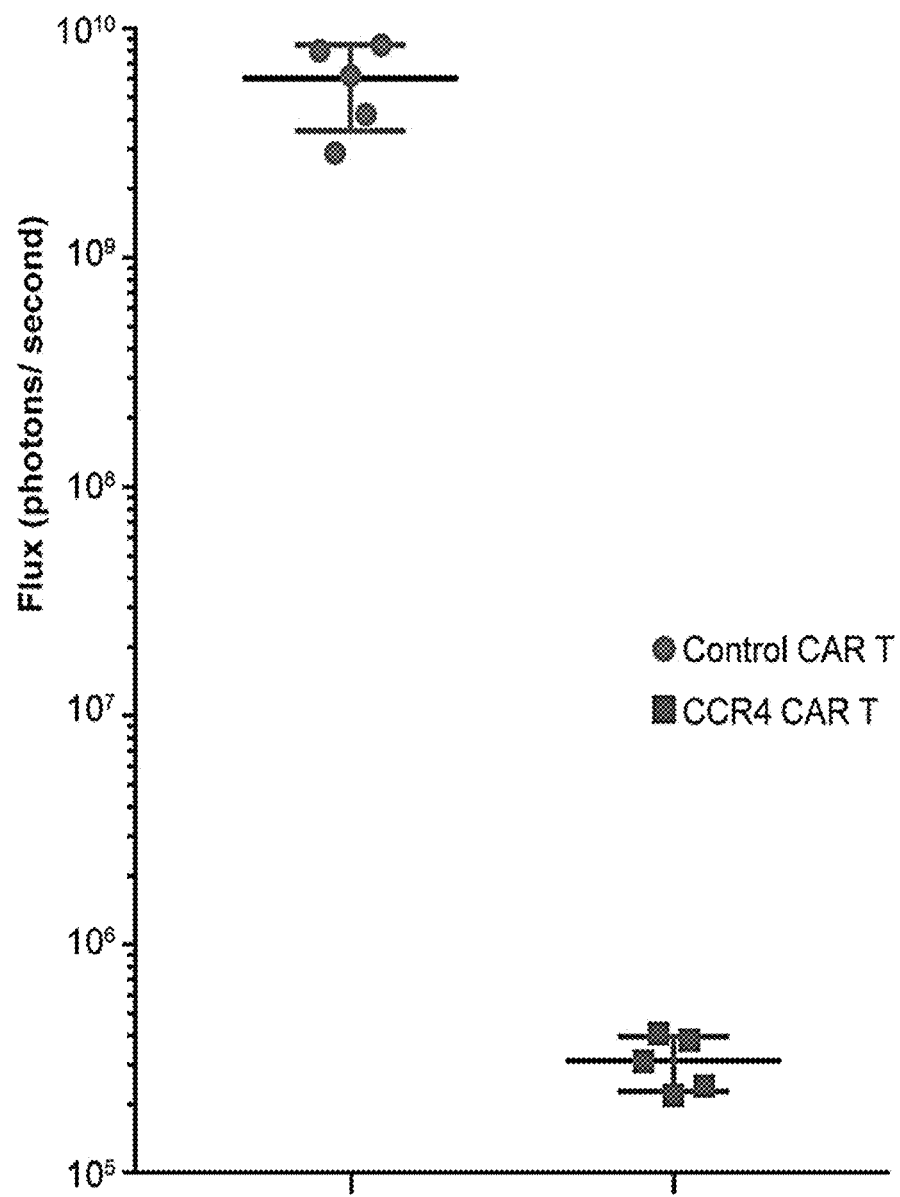
FIG. 9: Quantitative demonstration of the luminescence in tumor bearing mice. This is another representation of the data shown in FIGS. 6A-6B.

Despite the induction of several inflammatory cytokines such as TNF-alpha, TNF-beta, and IFN-gamma, a cytokine that is a principal driver of cytokine release syndrome often associated with CAR T cell therapy, IL-6 was not induced implying that the source of IL-6 seen in cytokine release syndrome is not the CAR T cells. The basal levels of MIP-1α and MP-10 expression in CCR4 CAR T cells were quite high (19 ng/ml and 31 ng/ml respectively) and these levels were further increased upon co-culture with target cells somewhat (36% and 25% respectively). Furthermore, no meaningful induction of the following cytokines was detected: IL-12/23p40, IL-12p70, IL-15, IL-16, IL-1a, IL-7, VEGF, IL-10, Eotaxin, Eotaxin-3, IP-10, MCP-1, MCP-4, TARC and IL-17. Finally, in vivo efficacy of the CCR4 CAR was tested in a murine xenograft model of adult T cell leukemia. Mice that were transfused with CCR4 CAR T cells completely eradicated tumor cells and remained tumor free (panel B of FIG. 6) at the conclusion of the study, while all of the control mice displayed continuing growth of tumor cells 12 weeks after transplanting ATL cells (FIG. 6A). Tumor growth was quantitated using bioluminescence imaging flux (photons/second) as a surrogate measurement of leukemic tumor burden (FIG. 9).

T-cell malignancies represent a heterogeneous group of lymphoid neoplasms often with a poor clinical outcome (Foss et al., Blood. 2011; 117(25):6756-6767.). Their relative lack of well-defined genetic aberrations perhaps with the exception of ALK(+) ALCL with t(2;5), along with the lack of definitive diagnostic markers have been a major impediment in unraveling the pathogenesis as well as devising novel efficacious therapeutic strategies for most T-cell malignancies (Foss et al., 2011, supra). With gene expression profiling, it has been recently established that nearly half of PTCL-NOS, a diverse group that accounts for about 50% of PTCL, lack any classifiable markers but overexpress the $T_H2$ master transcriptional regulator GATA-3 and often carry a poor prognosis (Wang et al., Blood. 2014; 123(19):3007-3015; Iqbal et al., Blood. 2014; 123(19):2915-2923). As in normal $T_H2$ CD4$^+$ T lymphocytes, GATA-3 drives the transcription of CCR4 in these PTCL-NOS and consequently they over-express cell surface CCR4 (Sundrud et al., J Immunol. 2003; 171(7):3542-3549). As almost all CTCL and ATL also overexpress CCR4, as well as a large percentage of ALCL especially the more aggressive ALK(–) subtype, the overexpression of surface CCR4 appears to be a target that can be exploited to develop therapeutic strategies with a broader applicability in the treatment of T-cell malignancies. Without being bound by theory, because Treg cells express CCR4 in abundance (Hirahara et al., *J Immunol.* 2006; 177(7):4488-4494), the CCR4-directed therapy is likely to eliminate Tregs that in the tumor microenvironment constitute a formidable barrier against tumor-eradicating host immune responses.

Figure 8B:
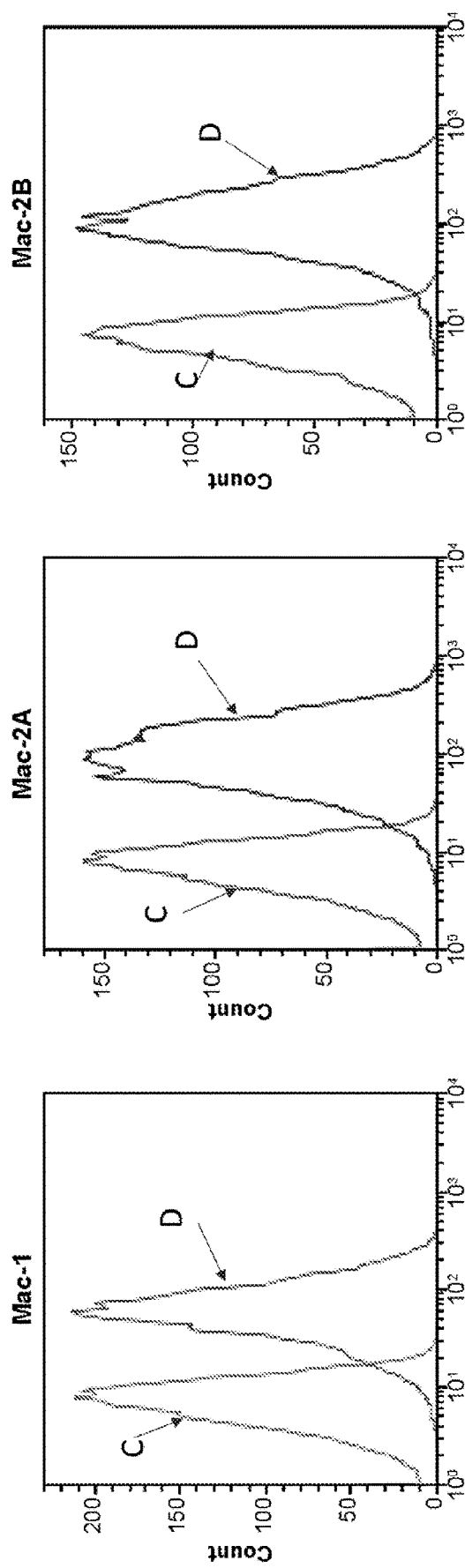

The expression of co-inhibitory ligands on target cells could also impact CAR T cell cytolytic activities. When the expression of PDL-1 was assessed in the panel of ATL cell lines, only ST1 displayed appreciable amount of PDL-1. In contrast, all ALCL cell lines displayed abundant cell surface expression of PDL-1 including the ALK negative Mac-1, Mac-2A and Mac-2B cell lines that were highly susceptible to CCR4 CAR T cell mediated cytolysis (see FIGS. 8A and 8B). Therefore, the expression of PDL-1 by itself likely does not explain any discrepancies between CCR4 expression and the effectiveness of cytolysis.

Therefore, the CCR4 CAR disclosed herein represents a novel adoptive cellular therapy approach for T cell malignancies in which ex-vivo engineered T cells are utilized to ablate a spectrum of neoplastic T-cell diseases in patients. The accumulating clinical experience with mogamulizumab and the documented unremarkable phenotypic features of CCR4 gene disrupted mice are reassuring (Ogura et al., *J Clin Oncol.* 2014; 32(11):1157-1163; Duvic et al., *Blood.* 2015; 125(12):1883-1889; Chvatchko et al., *J Exp Med.* 2000; 191(10):1755-1764), and a toxicity profile of a CCR4-targeted CAR T cell therapy can be generated. Unlike CD19 directed CAR therapies that result in long-term or permanent aplasia of B cells (Karlos et al., *Sci Transl Med.* 2011; 3(95):95ra73), the CCR4 directed CAR therapy is unlikely to cause major perturbation of T cell subsets in the treated individuals. As seen in data from FIG. 1A, it is clear that both $CD4^+$ and $CD8^+$ T cells can express the disclosed CAR and remain viable long term without undergoing self-ablation or fratricidal death in culture. The extracellular domain of rhesus macaque CCR4 is 100% identical to that of human CCR4 (GENBANK® Accession Nos. NP_001252949 and P51679 respectively, which are incorporated herein by reference) and the antibody from which the CCR4 CAR was derived reacts with rhesus macaque CCR4. Thus, an evaluative safety study can be conducted in rhesus macaques with ex-vivo engineering of monkey $CD3^+$ T cells with the CCR4 CAR and reinfusion of the autologous modified T cells back into the animals.

Thus, a chemokine receptor CCR4 directed CAR is disclosed herein that can be used to treat a spectrum of T-cell malignancies for which the existing treatment regimens are largely inadequate and do not confer long-term survival.

Example 3

Macaque Study

The following is an exemplary protocol for a toxicity study. Rhesus macaques are a suitable non-human primate species to assess anti-CCR4 CAR T-cells. Human and rhesus CCR4 are almost completely homologous in the region targeted by the CAR T receptor to be used in the clinical trial. Human and rhesus 4-1BB and CD3ξ signaling molecules are highly conserved (95%) and there is 100% identity of the immunoreceptor tyrosine activation motifs of CD3ξ. Thus, safety of any protocol can be confirmed in rhesus macacques.

Isolated T-cells are stimulated with CD3/CD28 Dynabeads in media supplemented with rhIL-2 (100 IU/mL) and transduced by exposing them to replication incompetent lentivirus vector encoding the CCR4 CAR T-cell receptor. Cells are stored at −80° C. CCR4 CAR T-cells are defined as cells that stain for both CD3 and protein L. Cells are expanded in culture for at least 7 days until a sufficient number of cells have been produced. (initial infusion and 1 complete backup for potential use.

Cytoxan (40 mg/kg over 2 hours) and fludarabine (40 mg/m² over 2 hours) is given IV daily×2 (days −7 and −6) as a preconditioning regimen. Intravenous hydration with normal saline (NS) and Mesna (10 mg/kg) is given 30 minutes before, 4, 6 and 8 hours after the Cytoxan to prevent urinary collecting system toxicities. In an exemplary protocol, leukaphoresis is performed at day −28 to −8, and CCR4 CAR T cells are produces as described above. On days −7 and =6, the animals are lymphodepeleted. On day 1, CCR4 CAR T cells are administered. There are two treatment groups (3 macaques each) one with preconditioning regimen alone and the second with CCR4 CAR T-cells administered @1×10⁷ transduced cell/kg on day 1. $CD4^+$ and $CD8^+$ CAR T-cells are selected and given at a 1:1 ratio.

| Dose Groups | | |
|---|---|---|
| Groups | Number of Test Subjects | Treatment |
| 1 | 3 | conditioning chemotherapy |
| 2* | 3* | conditioning chemotherapy plus 1 × 107 CAR T-cells/kg |

*may elect to reuse group 1 NHPs

Test animals are monitored clinically with vital signs (at least q12 hours and more frequently if there are signs of CRS), urinalyses and observed for signs of CRS or neurotoxicity. Routine laboratories including complete chemistry panel plus amylase and lipase, CBC and coagulation tests are assessed on a regular basis.

Example 4

Clinical Trial

An exemplary clinical trial is disclosed below. The goal of this study is to establish an effective adoptive cellular therapy by using subject's own transduced T-cells that target an antigen broadly expressed on T-cell leukemia/lymphomas.

Inclusion Criteria: Adult subjects with pathologically confirmed relapsed/refractory $CCR4^+$ lymphoid malignancies including cutaneous T-cell lymphoma (CTCL), Sezary Syndrome (SS) or chronic, lymphomatous or acute subtypes adult T-cell leukemia. Subjects must have measurable or evaluable disease. ATL subjects with >10% of the PBMCs having the characteristic abnormal (i.e., $CD3^{dim}$, $CD4^+$ $CD25^+$ expressing) FACS profile for circulating ATL cells are considered to have evaluable disease. Subjects must have adequate physiologic parameters:

a) Absolute granulocyte count 1000 K/uL, platelet count 75,000 K/uL and hemoglobin 9 g/dL.
   b) Bilirubin and creatinine ≤1.5×institutional ULN.
   c) AST, ALT 3.0×institutional ULN.
   d) Normal cardiac ejection fraction as determined by echocardiogram
   e) Karnofsky Performance Score≥70% or ECOG≤1; and
   f) FEV1 and DLco>60% of predicted.

Exclusion Criteria

1. Subjects with symptomatic leukemic meningitis, central nervous system (CNS) metastases, leukemic involvement with >100, 000 cells/mm³, GI tract involvement, serum calcium or LDH>1.5×the upper limit of normal are excluded. However, subjects that have both ATL and another HTLV-1 associated disease such as tropical spastic paraparesis (HAM/TSP) may be entered into the protocol depending on the severity of their symptoms.

2. Subjects who have received a prior allogeneic stem cell transplant

3. Subjects who have received high doses of systemic corticosteroids for the treatment of their ATL within 4 weeks prior to the start of therapy.

4. Subjects who have received any cytotoxic therapy, immunotherapy, antitumor vaccines or monoclonal antibodies in the 4 weeks prior to the start of the study.

5. Life expectancy of less than 3 months.

6. Documented active bacterial infections, active or chronic hepatitis B, hepatitis C or HTLV-II infection.

7. Subjects with a known history of hepatitis (Hep) B or C are not eligible due to the risk of reactivation of hepatitis associated with preparative chemotherapy. Subject must be seronegative for Hep B and C unless antigen negative. If hepatitis B or C antibody test is positive subjects must be tested for the presence of these viruses by quantitative HBV DNA or HCV RNA.

8. Subjects with human immunodeficiency virus (HIV) are not eligible for this study because by definition their immune response is defective putting them at much higher risk for opportunistic infections.

9. Pregnant and breast-feeding subjects are not eligible for the study because the effects of CCR4 CAR T-cells on the developing fetus are unknown.

10. Inability or refusal to practice effective contraception during therapy. Men and women of childbearing potential must use an effective method of birth control or abstinence during treatment and for 4 months after completion of the treatment.

11. Subject has significant and/or uncontrolled cardiac, renal, hepatic or other systemic disorders or significant psychological conditions at baseline visit that in the investigator's judgment would jeopardize subject enrollment or compliance with the study procedures.

Overview: After their eligibility is established, subjects undergo a leukapheresis to obtain a sufficient number of peripheral blood mononuclear cells (PBMCs) and selected for CD8$^+$ peripheral blood lymphocytes to transduce to express a chimeric antigen receptor specific for CCR4 by exposing the activated lymphocytes to the supernatant containing the lentivirus CCR4-CAR.Bξ vector. The transduced cells are expanded for 7 to 10 days, tested for anti-tumor activity and sterility prior to administration to the subjects. These effector cells can be used immediately after production or cryopreserved and thawed prior to use at a later date. Five days prior the planned reinfusion of these effector cells, the subjects begin a standard 3-day preparative regimen of Cyclophosphamide and Fludarabine, followed by the infusion of the CCR4-CAR-T cells and post-treatment Dose Limiting Toxicity: Dose-limiting toxicity is defined as follows:
Grade 4 neutropenia lasts longer than 21 days from the day of cell transfer
Grade 4 thrombocytopenia lasts longer than 35 days from the day of cell transfer
All grade 3 and 4 toxicities with the exception of:
Grade 3 cytokine release syndrome (CRS) that responds to appropriate medical interventions within 3 days and recovers to ≤grade 2.
Grade 4 neutropenia (ANC<500/mm$^3$) or grade 4 thrombocytopenia (platelet count<25,000/mm$^3$) lasting less than 7 days in the absence of sepsis grade 4 infection or bleeding.
Uncomplicated grade 3 infections
Toxicities occurring within 24 hours' post cell infusion (related to cell infusion) that are reversible to a ≤grade 2 within 8 hours with appropriate medical therapies.
Hypotension requiring treatment with vasopressors (norepinephrine dose of >2 mcg/minute or equivalent, doses less than or equal to 2 mcg/minute are not a DLT) for 72 hours or less. The 72 hours is measured from the first institution of vasopressors even if vasopressors are temporarily discontinued and then re-started.
Grade 4 elevation in alanine aminotransferase, aspartate aminotransferase, or bilirubin that resolves baseline or grade 1 within 7 days.
Grade 3 nausea, vomiting or diarrhea lasting less than 3 days.

Dose Escalation: Dose escalation proceeds in cohorts of 3-6 subjects with number of CCR4 CAR T-CELLS-T-cells [IS THIS CORRECT? T CELLS IS REPEATED?] administered based on the subject's actual weight. The maximum tolerated dose (MTD) is the dose level at which no more than 1 of up to 6 subjects experience dose limiting toxicities (DLT) during treatment, and the dose below that at which at least 2 (of ≤6) subjects have DLT because of the drug. A total of 21 to 33 subjects that includes up to 3 replacements for unevaluable subjects are enrolled. If a subject did not experience DLT, but did not receive their CCR4 CAR T-cell infusion, he or she is not be evaluable for toxicity and is replaced at that dose level.

TABLE 3

Dose Escalation Cohorts

| Subject Cohort | Number of Subjects | CCR4 CAR T-CELLS cells/kg |
| --- | --- | --- |
| 1 | 3 to 6 | 0.3 × 10$^6$ |
| 2 | 3 to 6 | 1 × 10$^6$ |
| 3 | 3 to 6 | 3 × 10$^6$ |
| Expansion | 9 to 12 | |

Each dose level contains a minimum of 3 subjects and the cell doses aredetermined by the count of freshly cultured or thawed cryopreserved CAR T-cells just prior to their infusion. There is an at least 14-day delay in the CAR T-cell infusion between subjects treated sequentially at the same dose level.

Dose escalation follows the rules outlined in the Table 4 below.

TABLE 4

DLT and Dose Escalation Decision

| Number of Subjects with DLT at a Given Dose Level | Escalation Decision Rule |
| --- | --- |
| 0 out of 3 | Enter up to 3 subjects at the next dose level |
| ≥2 | Dose escalation is stopped. This dose level is declared the maximally administered dose (highest dose administered). Up to three (3) additional subjects are entered at the next lowest dose level if only 3 subjects were treated previously at that dose. |
| 1 out of 3 | Enter up to 3 more subjects at this dose level. If 0 of these 3 subjects experience DLT, proceed to the next dose level. If 1 or more of this group suffer DLT, then dose escalation is stopped, and this dose is declared the maximally administered dose. Up to three (3) additional subjects are entered at the next lowest dose level |

TABLE 4-continued

DLT and Dose Escalation Decision

| Number of Subjects with DLT at a Given Dose Level | Escalation Decision Rule |
|---|---|
| | if only 3 subjects were treated previously at that dose. |
| ≤1 out of 6 at highest dose level below the maximally administered dose | This is the MTD and is generally the recommended phase 2 dose. At least 6 subjects must be entered at the recommended phase 2 dose. |

Treatment Administration:

Leukapheresis: The subject undergoes a 15 liter leukapheresis to obtain a target yield of approximately 6–10× $10^9$ mononuclear cells. The procedure requires dual venous access, and takes approximately 3-4 hours to complete. A central line is placed if peripheral venous access is not sufficient.

Preparation of Cellular Product: Peripheral blood CD8 lymphocytes are isolated using CD8 microbeads. The isolated T-cells are stimulated with CD3/CD28 beads in media supplemented with rhIL-2 (100 IU/ml) and transduced by exposing them to the replication-incompetent lentivirus vector encoding the anti-CCR4 CAR T-cells. The cells are maintained in culture for at least 7 days until a sufficient number of effector cells have been produced. CCR4 CAR T-cells are defined as cells staining for both CD3 and protein L (Zheng et al., Transl Med 2012; 10: 29-35) in flow cytometry assays and are quantitated by flow cytometry and assessed for lytic capacity against a CCR4 expressing ED (−) 41214 cell line target. Sufficient cells are produced for the initial cellular infusion for administration to the subject and one complete back-up cellular product for potential later use.

Verification of Cellular Product: The cellular product is assessed for viability and contamination with infectious agents by performing the procedures listed below in Table 5

TABLE 5

Decision Criteria for Verifying Cellular Product

| Test | Method | Criteria |
|---|---|---|
| Identity[1] | PCR | # copies of CCR4-BBζ per $CD3^+$ cell |
| Cell viability[2] | Trypan blue exclusion | ≥70% |
| Cell number[2] | cell counter | within 20% of planned dose level |
| % CAR+ cells[2] | Protein L | ≥10% |
| Endotoxin[3] | Gel Clot | ≤5 EU/mL |
| Mycoplasma[3] | Mycoplasma test | Negative |
| VSV-G[3] | q-PCR | Negative |
| Replication Competent Lentivirus[4] | p24 antigen + PERT Assay | Negative |
| Sterility testing[5] | gram stain[6], culture | Negative |

[1]Performed on a sample obtained between days −4 and −1 with the results not available by the time of infusion
[2]Performed on a sample obtained from final cellular product immediately prior to infusion with the results available at the time of infusion
[3]Performed on a sample obtained between days −4 and −1 with the results available by the time of infusion.
[4]Cultures are obtained on day −2 and sent to IU Vector Production Facility for analysis. Results are pending at the time of infusion not be available for several weeks after the cellular infusion.
[5]Sample is obtained from the final cellular product prior to the infusion and the results are not available prior to the cellular infusion.
[6]Gram stain is performed on the final cellular product with results available by the time of the infusion.

Conditioning chemotherapy and anti-CCR 4 CAR T-cell administration:
Overall Summary of the Treatment Plan

TABLE 6

Treatment Summary

| Drug | Dose | Days |
|---|---|---|
| Cyclophosphamide | 300 mg/m² IV infusion over 30 minutes | Daily × 3 doses on days −4, −,3 −2 |
| Fludarabine | 30 mg/m² IV infusion over 30 minutes administered immediately following the cyclophosphamide | Daily × 3 doses on days −4, −3, −2 |
| Anti-CCR CAR T cells | Variable. | Infuse on day 1 |

Detailed chemotherapy treatment days −4, −3, −2 and −1. Subjects begin allopurinol 200 or 300 mg orally daily. Subjects receive pre-hydration with 1000 mL 0.9% sodium chloride IV over 1 to 3 hours. Subjects receive ondansetron 16 to 24 mg orally on days −4, −3, and −2 beginning 1 hour before chemotherapy (IV ondansetron can be substituted). Additional anti-emetics such as lorazepam and prochlorperazine can also be given to for break-through nausea. Cyclophosphamide at a dose of 300 mg/m²IV is diluted in 100 ml 5% dextrose solution and infused over 30 minutes. After the cyclophosphamide infusion is completed, subjects receive Fludarabine 30 mg/m² IV in 100 mL 0.9% sodium chloride over 30 minutes. In subjects with a creatinine clearance calculated by the CKD-EPI equation less than 80 ml/minute, the daily dose of Fludarabine is reduced by 20%. Following completion of the Fludarabine infusion, subjects receive 1000 mL 0.9% sodium chloride IV over 1-2 hours. Furosemide is given if needed.

Day-1: No interventions except as needed for general supportive care such as anti-emetics. To minimize bladder toxicity, subjects should increase normal oral fluid intake to at least 2 L/day.

Detailed treatment plan day 1:

1. It is confirmed that the subject is hemodynamically stable, has not developed respiratory insufficiency, significant biochemical laboratory abnormalities or has signs of a new infectious process and can tolerate administration of the CAR T-cells. If the subject has developed significant problems that would complicate the administration of the cellular product, administration of CAR T-cells may be delayed up to 72 hours. Approximately 30 to 45 minutes prior to the CCR4 CAR T-cell infusion, the subject is premedicated with acetaminophen 650 mg orally and diphenhydramine 25 to 50 mg orally or 25 mg IV.

2. If the CAR T-cells have been cryopreserved, the cellular product is thawed and brought to room temperature (≈25° C.). After confirmation that the anti-CCR4 CAR T cells have met their release criteria, the cell product is delivered.

3. The CCR4 CAR T cells are infused intravenously over 20 minutes through a free flowing central venous catheter via non-filtered tubing while the infusion bag is gently agitated to prevent clumping of the CAR T-cells.

4. The subjects' vital signs (heart rate, respiratory rate, temperature, blood pressure and oxygen saturation) are assessed immediately prior to beginning the cell infusion, every 15 minutes (±5 min) for the first hour, every 30 minutes (±10 min) for the second hour and hourly for 2 additional hours (±10 min) after initiating the cellular infusion. Vital signs are performed more frequently if the subject has acute toxicities related to the cellular infusion as clinically indicated until stabilized. Infusion of the cellular product may be slowed or interrupted if needed.

5. Appropriate respiratory therapy, additional IVFs, diuretics, additional antihistamines, anti-arrhythmic, vasopressors, diuretics and oxygen therapy are administered as required to address acute or subacute infusional toxicities.

6. Subjects with systolic blood pressure (BP) <80% of their baseline BP or <100 mmHg receive 1 L of NS over 2 to 3 minutes. Subjects that do not respond to this initial 1 L of normal saline (NS) should receive an additional 1 L of NS over 10 minutes and be transferred to the ICU. Subjects with a systolic BP of <85 mmHg should be transferred to the ICU. Subjects with tachycardia >125 beats per minute on 2 occasions separated by 3 hours should be transferred to the ICU. Subjects requiring 4 L or more of supplemental oxygen by nasal cannula should be transferred to the ICU.

Detailed treatment plan days 2 to 7:

1. Mandatory hospitalization for observation and treatment as necessary. Subjects have routine vital signs obtained every 4 hours and more frequently if clinically indicated. Routine chemistry and hematology panels are assessed daily in the immediate post CAR T-cell infusion period while the subject is hospitalized. Subjects who experience hypotension, tachycardia, hypoxia or significant (>grade 2) neurologic dysfunction should be similarly transferred to the ICU.

2. Filgrastim (≈5 mcg/kg/day) SC is administered beginning on day 2 and continued until the subject's absolute neutrophil count (ANC) has reached 500 cells/mm$^3$.

3. Subjects who are febrile while neutropenic (ANC<500/mm$^3$) or have a fever with localizing symptoms or finding suspicious for infection are treated with appropriate empiric antibiotics and have appropriate microbiologic cultures obtained. Clinical findings and/or culture results dictate additional radiographic procedures or changes in antimicrobial therapy.

4. Subjects with Cytokine Release Syndrome (CRS) that commonly occurs within the first few days after the CAR T-cell infusion are treated Response Criteria:

1. Criteria of Response for Malignant Lymphoma a. Complete response: The designation of a complete response (CR) requires all of the following: (1) Complete disappearance of all detectable clinical evidence of disease and disease-related symptoms if present before therapy; (2) a post-treatment residual mass is permitted as long as it is PET negative. If a pretreatment PET scan was negative, all lymph nodes and nodal masses must have regressed on CT to normal size (<1.5 cm in their greatest transverse diameter for nodes >1.5 cm before therapy); (3) Previously involved nodes that were 1.1 to 1.5 cm in their long axis and more than 1.0 cm in their short axis before treatment must have decreased to <1.0 cm in their short axis after treatment; (4) The spleen and/or liver if considered enlarged before therapy based on a physical examination or CT scan, should not be palpable on physical examination and should be considered normal size by imaging studies, and (5) If the bone marrow was involved by lymphoma before treatment the infiltrate must have cleared on repeat bone marrow biopsy.

b. Partial response: The designation of a partial response (PR) requires all of the following: (1) At least a 50% reduction in the sum of the product of the diameters of up to six of the largest dominant nodes or nodal masses. These nodes or masses should be selected according to all of the following: they should be clearly measurable in at least two perpendicular dimensions; if possible they should be from disparate regions of the body; and they should include mediastinal and retroperitoneal areas of disease whenever these sites are involved; (2) No increase in the size of other nodes, liver, or spleen; (3) Splenic and hepatic nodules must regress by >50% in their SPD or for single nodules in the greatest transverse diameter; (4) With the exception of splenic and hepatic nodules, involvement of other organs is usually assessable and no measurable disease should be present. Bone marrow assessment is irrelevant for determination of a PR if the sample was positive before treatment. Subjects who achieve a CR by the above criteria but who have persistent morphologic bone marrow involvement are considered partial responders; (5) No new sites of disease; (6) If the pretreatment PET scan was positive, the post-treatment PET should be positive in at least one previously involved site; and (7) If a pretreatment PET was negative, CT criteria should be used.

c. Stable disease: A subject is considered to have stable disease (SD) when he or she fails to attain the criteria needed for a CR or PR, but does not fulfill those for progressive disease. The PET should be positive at prior sites of disease with no new areas of involvement on the post treatment CT or PET. If the pretreatment PET was negative, there must be no change in the size of the previous lesions on the post treatment CT scan.

d. Progressive disease: Lymph nodes are considered abnormal if the long axis is more than 1.5 cm regardless of the short axis. If a lymph node has a long axis of 1.1 to 1.5 cm, it is only be considered abnormal if its short axis is more than 1.0 cm. Lymph nodes <1.0×<1.0 cm are not be considered as abnormal for relapse or progressive disease. Other criteria for progressive disease include the following: (1) Appearance of any new lesion more than 1.5 cm in any axis during or at the end of therapy, even if other lesions are decreasing in size. Increased FDG uptake in a previously unaffected site is only considered relapsed or progressive disease after confirmation with other modalities. (2) At least a 50% increase from nadir in the sum of the products of the diameters of any previously involved nodes, or in a single involved node, or the size of other lesions. A lymph node with a diameter of the short axis of less than 1.0 cm must increase by >50% and to a size of 1.5×1.5 cm or more than 1.5 cm in the long axis. (3) At least a 50% increase in the longest diameter of any single previously identified node more than 1 cm in its short axis; (4) Lesions should be PET positive if the lesion was PET positive before therapy unless the lesion is too small to be detected by PET; (5) Measurable extranodal disease should be assessed in a manner similar to that for nodal disease. For these recommendations, the spleen is considered nodal disease. Disease that is only assessable is recorded as present or absent only, unless, while an abnormality is still noted by imaging studies or physical exam, it is found to be histologically negative.

2. Criteria of Response for ATL a. Complete response: Complete response (CR) is defined as disappearance of all clinical, microscopic, and radiographic evidence of disease. All nodes must have regressed to normal size (1.5 cm in their greatest transverse diameter) and previously involved nodes that were 1.1 to 1.5 cm must have decreased to 1.0 cm. Because HTLV-1 carriers frequently have a small percentage of abnormal lymphocytes with polylobated nuclei, so called flower cells in peripheral blood, provided that less than 5% of such cells remained and the absolute lymphocyte count, including flower cells, was less than 4×10$^9$/L, CR is attained.

b. Complete response unconfirmed: A designation of unconfirmed complete response (CRu) requires a 75% reduction in tumor size with a residual mass after treatment.

c. Partial response: Partial response (PR) is defined as a 50% reduction in the sum of the products of the greatest diameters of measurable disease without the appearance of new lesions. In addition, a 50% or greater reduction in absolute abnormal lymphocyte counts in peripheral blood is required to attain PR.

d. Progressive disease: Progressive disease (PD) in peripheral blood is defined by a 50% increase from nadir in the count of flower cells and an absolute lymphocyte count, including flower cells, of $4 \times 10^9$/L. PD or relapsed disease in the other lesions is defined as a 50% increase from nadir in the sum of the products of measurable disease or the appearance of new lesions excluding skin.

e. Stable disease: Stable disease is defined as failure to attain CR/PR or PD.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method for treating a subject with a malignancy that produces CCR4 mRNA, comprising:
    transducing CD3+ T cells and/or natural killer cells from the subject with a nucleic acid molecule encoding a chimeric antigen receptor, wherein the nucleic acid molecule comprises the nucleic acid sequence of SEQ ID NO: 11, and wherein the chimeric antigen receptor comprises:
    (a) an extracellular scFv comprising a light chain variable domain ($V_L$) and a heavy chain variable domain ($V_H$), wherein the scFv specifically binds to CCR4, wherein the $V_H$ comprises a heavy chain complementarity determining region (HCDR)1, an HCDR2 and an HCDR3, wherein the HCDR1 comprises amino acids 26-33 of SEQ ID NO: 1, the HCDR2 comprises amino acids 51-58 of SEQ ID NO: 1, and the HCDR3 comprises amino acids 99-107 of SEQ ID NO: 1, and wherein the $V_L$ comprises a light chain complementarity determining region (LCDR)1, a LCDR2 and a LCDR3, wherein the LCDR1 comprises amino acids 27-38 of SEQ ID NO: 2, the LCDR2 comprises amino acids 56-61 of SEQ ID NO: 2, and the LCDR3 comprises amino acids 95-102 of SEQ ID NO: 2;
    (b) a hinge and transmembrane domain from CD8;
    (c) an intracellular 4-1BB signaling domain;
    (d) an intracellular CD3 zeta signaling domain, wherein (a)-(d) are in N-terminal to C-terminal order, and wherein the chimeric antigen receptor further comprises an immunoglobulin signal sequence comprising the amino acid sequence of SEQ ID NO: 4;
    to produce autologous transduced cells that express the chimeric antigen receptor; and
    administering to the subject a therapeutically effective amount of the autologous transduced cells that express the chimeric antigen receptor, thereby treating the malignancy that produces CCR4 mRNA in the subject.

2. The method of claim 1, wherein the malignancy is adult T cell leukemia, cutaneous T cell lymphoma, anaplastic large cell lymphoma, Hodgkin's lymphoma, peripheral T cell lymphoma or a diffuse large B cell lymphoma.

3. The method of claim 2, wherein the adult T cell leukemia is chronic adult T cell leukemia, acute adult T cell leukemia, smoldering T cell leukemia, or lymphomatous T cell leukemia.

4. The method of claim 1, wherein the hinge and the transmembrane domain from CD8 comprise the amino acid sequence set forth as SEQ ID NO: 7.

5. The method of claim 1, wherein the intracellular 4-1BB signaling domain comprises the amino acid sequence set forth as SEQ ID NO: 8.

6. The method of claim 1, wherein the CD3 zeta signaling domain comprises the amino acid sequence set forth as SEQ ID NO: 9.

7. The method of claim 1, comprising a nucleic acid molecule encoding the $V_L$ that is at least 95% identical to SEQ ID NO: 12.

8. The method of claim 1, wherein the nucleic acid molecule encoding the chimeric antigen receptor comprises a nucleic acid sequence encoding the $V_H$ that is at least 95% identical to SEQ ID NO: 13.

9. The method of claim 8, wherein the nucleic acid sequence encoding the VH is SEQ ID NO: 13, and wherein the nucleic acid molecule comprises a nucleic acid sequence encoding the $V_L$, and wherein the nucleic acid sequence encoding the $V_L$ is SEQ ID NO: 12.

10. The method of claim 1, wherein the CD8 transmembrane domain and hinge are encoded by a nucleic acid sequence at least 80% identical to SEQ ID NO: 15, wherein the encoded protein functions as a CD8 transmembrane domain and hinge.

11. The method of claim 10, wherein the nucleic acid molecule encoding the chimeric antigen receptor comprises the nucleic acid sequence of SEQ ID NO: 15.

12. The method of claim 1, wherein the 4-1BB signaling domain is encoded by a nucleic acid sequence at least 80% identical to SEQ ID NO: 16, wherein the encoded protein functions as a 4-1BB signaling domain.

13. The method of claim 1, wherein the CD3 Zeta signaling domain is encoded by nucleic acid sequence at least 80% identical to SEQ ID NO: 17, wherein the encoded protein functions as a CD3 Zeta signaling domain.

14. The method of claim 13, wherein the nucleic acid molecule encoding the chimeric antigen receptor comprises the nucleic acid sequence of SEQ ID NO: 17.

15. The method of claim 1, wherein the nucleic acid molecule encoding the chimeric antigen receptor is codon-optimized for expression in human cells.

16. The method of claim 1, wherein the nucleic acid molecule encoding the chimeric antigen receptor comprises the nucleic acid sequence of SEQ ID NO: 18.

17. The method of claim 1, comprising transducing the CD3+ T cells and/or natural killer cells from the subject with an expression vector comprising the nucleic acid molecule encoding the chimeric antigen receptor, wherein the vector is a viral vector.

18. The method of claim 17, wherein the viral vector is a lentiviral vector or a gamma retroviral vector.

19. The method of claim 1, wherein the CD3+ T cells are autologous to the subject.

20. The method of claim 1, wherein the CD3+ T cells comprise CD3$^+$CD4$^+$ T cells and/or CD3$^+$CD8$^+$ T cells.

21. The method of claim 1, wherein the method reduces the number of Foxp3$^+$CD4$^+$ Treg cells in the subject.

22. The method of claim 1, wherein the subject is human.

23. The method of claim 1, wherein the malignancy is a solid tumor.

24. The method of claim 1, wherein the malignancy is a lymphoid malignancy.

25. The method of claim 1, wherein the method reduces the number of Foxp3$^+$CD$^{4+}$ Treg cells a tumor microenvironment in the subject.

26. The method of claim 1, wherein the nucleic acid molecule encoding the chimeric antigen receptor is RNA.

27. The method of claim 1, wherein the method comprises transducing CD3+ T cells from the subject with the nucleic acid molecule encoding the chimeric antigen receptor, and wherein the method further comprises:

stimulating the CD3+ cells from the subject with an antibody that specifically binds CD3 and an antibody that specifically binds CD28.

28. A method for treating a subject with a malignancy that produces CCR4 mRNA, comprising:
transducing CD3+ T cells and/or natural killer cells from the subject with a nucleic acid molecule encoding a chimeric antigen receptor, wherein the chimeric antigen receptor comprises the amino acid sequence set forth as SEQ ID NO: 10 to produce autologous transduced cells that express the chimeric antigen receptor; and
administering to the subject a therapeutically effective amount of the autologous transduced cells that express the chimeric antigen receptor, thereby treating the malignancy that produces CCR4 mRNA in the subject.

29. The method claim 28, wherein the nucleic acid molecule encoding the chimeric antigen receptor comprises the nucleic acid sequence of SEQ ID NO: 16.

30. A method for treating a subject with a malignancy that produces CCR4 mRNA, comprising:
transducing CD3+ T cells and/or natural killer cells from the subject with a nucleic acid molecule encoding a chimeric antigen receptor, to produce autologous transduced cells that express the chimeric antigen receptor, wherein the nucleic acid molecule comprises the nucleic acid sequence of SEQ ID NO: 14, and
wherein the chimeric antigen receptor comprises:
(a) an extracellular scFv comprising a light chain variable domain ($V_L$) and a heavy chain variable domain ($V_H$), wherein the scFv specifically binds to CCR4, wherein the $V_H$ comprises a heavy chain complementarity determining region (HCDR)1, an HCDR2 and an HCDR3, wherein the HCDR1 comprises amino acids 26-33 of SEQ ID NO: 1, the HCDR2 comprises amino acids 51-58 of SEQ ID NO: 1, and the HCDR3 comprises amino acids 99-107 of SEQ ID NO: 1, and wherein the $V_L$ comprises a light chain complementarity determining region (LCDR)1, a LCDR2 and a LCDR3, wherein the LCDR1 comprises amino acids 27-38 of SEQ ID NO: 2, the LCDR2 comprises amino acids 56-61 of SEQ ID NO: 2, and the LCDR3 comprises amino acids 95-102 of SEQ ID NO: 2, wherein scFv comprises a linker, and
(b) a hinge and transmembrane domain from CD8;
(c) an intracellular 4-1BB signaling domain;
(d) an intracellular CD3 zeta signaling domain, wherein (a)-(d) are in N-terminal to C-terminal order; and
administering to the subject a therapeutically effective amount of the autologous transduced cells that express the chimeric antigen receptor, thereby treating the malignancy that produces CCR4 mRNA in the subject.

\* \* \* \* \*